(12) United States Patent
Mostafavi et al.

(10) Patent No.: US 9,498,167 B2
(45) Date of Patent: Nov. 22, 2016

(54) SYSTEM AND METHODS FOR TREATING PATIENTS USING RADIATION

(75) Inventors: Hassan E. Mostafavi, Los Altos, CA (US); Marcel R. Marc, San Jose, CA (US); Stanley Mansfield, Sunnyvale, CA (US); Raymond D. McIntyre, Los Altos Hills, CA (US); Ross B. Hannibal, Saratoga, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 2361 days.

(21) Appl. No.: 11/415,957

(22) Filed: May 1, 2006

(65) Prior Publication Data
US 2007/0014391 A1  Jan. 18, 2007

Related U.S. Application Data

(60) Provisional application No. 60/676,138, filed on Apr. 29, 2005.

(51) Int. Cl.
*A61B 5/05* (2006.01)
*A61B 6/03* (2006.01)
(Continued)

(52) U.S. Cl.
CPC .............. *A61B 6/032* (2013.01); *A61B 6/037* (2013.01); *A61B 6/0457* (2013.01); *A61B 6/5235* (2013.01); *A61B 6/547* (2013.01); *A61N 5/10* (2013.01); *A61N 5/1049* (2013.01); *A61N 5/1081* (2013.01); *G01N 23/04* (2013.01);
(Continued)

(58) Field of Classification Search
USPC ................... 606/130; 378/65, 205; 250/491; 600/426, 439, 427, 430
See application file for complete search history.

(56) References Cited

U.S. PATENT DOCUMENTS

| | | |
|---|---|---|
| 3,133,227 A | 5/1964 | Brown et al. |
| 3,144,552 A | 8/1964 | Schonberg et al. |

(Continued)

FOREIGN PATENT DOCUMENTS

| | | |
|---|---|---|
| AU | 746987 B2 | 2/2000 |
| AU | 2002215340 B2 | 4/2005 |

(Continued)

OTHER PUBLICATIONS

Final Office Action dated Jan. 11, 2010 for U.S. Appl. No. 11/415,866.
(Continued)

*Primary Examiner* — Joel F Brutus
(74) *Attorney, Agent, or Firm* — Vista IP Law Group, LLP

(57) ABSTRACT

A radiation system includes a radiation source having an accelerator, the radiation source having a magnetic field associated therewith that is resulted from an operation of the accelerator, and a magnetic field source configured to provide a compensating magnetic field to at least partially counteract against the magnetic field that is resulted from the operation of the accelerator. A radiation system includes a radiation device having a radiation source, a patient support, and a protective guard located between the radiation source and the patient support, wherein the protective guard is moveably coupled to the radiation device or the patient support. A radiation system includes a particle generator for generating a particle, an accelerator for accelerating the particle, and a magnetic source for changing a trajectory of the particle, wherein the magnetic source comprises a permanent magnet.

41 Claims, 26 Drawing Sheets

(51) Int. Cl.
*A61N 5/10* (2006.01)
*G01N 23/04* (2006.01)
*G21K 1/093* (2006.01)
*A61B 5/06* (2006.01)
*A61B 5/11* (2006.01)
*A61B 6/04* (2006.01)
*A61B 6/08* (2006.01)
*A61B 6/10* (2006.01)
*A61B 6/00* (2006.01)

(52) U.S. Cl.
CPC ............... *G21K1/093* (2013.01); *A61B 5/06* (2013.01); *A61B 5/1127* (2013.01); *A61B 6/0414* (2013.01); *A61B 6/08* (2013.01); *A61B 6/107* (2013.01); *A61B 6/4085* (2013.01); *A61B 6/4441* (2013.01); *A61B 6/482* (2013.01); *A61B 6/5247* (2013.01); *A61N 5/1064* (2013.01); *A61N 2005/1094* (2013.01)

(56) References Cited

U.S. PATENT DOCUMENTS

| | | |
|---|---|---|
| 3,193,717 A | 7/1965 | Nunan |
| 3,504,179 A | 3/1970 | Hainault |
| 3,751,028 A | 8/1973 | Scheininger et al. |
| 3,837,635 A | 9/1974 | Long et al. |
| 3,843,112 A | 10/1974 | McDonald |
| 3,948,559 A | 4/1976 | Hain et al. |
| 3,987,281 A | 10/1976 | Hodes |
| 4,112,306 A | 9/1978 | Nunan |
| 4,149,247 A | 4/1979 | Pavkovich et al. |
| 4,149,248 A | 4/1979 | Pavkovich |
| 4,208,675 A | 6/1980 | Bajon et al. |
| 4,209,706 A | 6/1980 | Nunan |
| 4,314,158 A | 2/1982 | Lucido |
| 4,521,808 A | 6/1985 | Ong et al. |
| 4,542,547 A | 9/1985 | Sato |
| 4,547,892 A | 10/1985 | Richey et al. |
| 4,593,967 A | 6/1986 | Haugen |
| 4,628,523 A | 12/1986 | Heflin |
| 4,675,731 A | 6/1987 | Takasu et al. |
| 4,679,076 A | 7/1987 | Vikterlof et al. |
| 4,726,046 A | 2/1988 | Nunan |
| 4,741,621 A | 5/1988 | Taft et al. |
| 4,825,393 A | 4/1989 | Nishiya |
| 4,853,777 A | 8/1989 | Hupp |
| 4,868,843 A | 9/1989 | Nunan |
| 4,868,844 A | 9/1989 | Nunan |
| 4,949,408 A | 8/1990 | Trkla |
| 5,001,344 A | 3/1991 | Kato et al. |
| 5,013,018 A | 5/1991 | Sicek et al. |
| 5,014,292 A | 5/1991 | Siczek et al. |
| 5,027,818 A | 7/1991 | Bova et al. |
| 5,039,867 A | 8/1991 | Nishihara et al. |
| 5,080,100 A | 1/1992 | Trotel |
| 5,099,505 A | 3/1992 | Seppi et al. |
| 5,117,445 A | 5/1992 | Seppi et al. |
| 5,117,829 A | 6/1992 | Miller et al. |
| 5,157,707 A | 10/1992 | Ohlson |
| 5,168,532 A | 12/1992 | Seppi et al. |
| 5,247,555 A | 9/1993 | Moore et al. |
| 5,262,649 A | 11/1993 | Antonuk et al. |
| 5,317,616 A | 5/1994 | Swerdloff et al. |
| 5,329,567 A | 7/1994 | Ikebe |
| 5,332,908 A | 7/1994 | Weidlich |
| 5,335,255 A | 8/1994 | Seppi et al. |
| 5,379,468 A | 1/1995 | Cassidy et al. |
| 5,394,452 A | 2/1995 | Swerdloff et al. |
| 5,400,255 A | 3/1995 | Hu |
| 5,410,767 A | 5/1995 | Barud |
| 5,411,026 A | 5/1995 | Carol |
| 5,427,097 A | 6/1995 | Depp |
| 5,438,991 A | 8/1995 | Yu et al. |
| 5,442,675 A | 8/1995 | Swerdloff et al. |
| 5,471,516 A | 11/1995 | Nunan |
| 5,471,546 A | 11/1995 | Meier |
| 5,509,042 A | 4/1996 | Mazess |
| 5,521,957 A | 5/1996 | Hansen |
| 5,525,905 A | 6/1996 | Mohapatra et al. |
| 5,528,650 A | 6/1996 | Swerdloff et al. |
| 5,533,082 A | 7/1996 | Gronemeyer et al. |
| 5,537,452 A | 7/1996 | Shepherd et al. |
| 5,548,627 A | 8/1996 | Swerdloff et al. |
| 5,552,606 A * | 9/1996 | Jones et al. ............ 250/363.04 |
| 5,591,983 A | 1/1997 | Yao |
| 5,615,430 A | 4/1997 | Nambu et al. |
| 5,625,663 A | 4/1997 | Swerdloff et al. |
| 5,647,663 A | 7/1997 | Holmes |
| 5,651,043 A | 7/1997 | Tsuyuki et al. |
| 5,661,773 A | 8/1997 | Swerdloff et al. |
| 5,663,995 A | 9/1997 | Hu |
| 5,663,999 A | 9/1997 | Siochi |
| 5,673,300 A | 9/1997 | Reckwerdt et al. |
| 5,675,625 A | 10/1997 | Rockseisen |
| 5,681,326 A | 10/1997 | Lax |
| 5,692,507 A | 12/1997 | Seppi et al. |
| 5,719,914 A | 2/1998 | Rand et al. |
| 5,724,400 A | 3/1998 | Swerdloff et al. |
| 5,748,700 A | 5/1998 | Shepherd et al. |
| 5,748,703 A | 5/1998 | Cosman |
| 5,748,907 A | 5/1998 | Crane |
| 5,751,781 A | 5/1998 | Brown et al. |
| 5,757,881 A | 5/1998 | Hughes |
| 5,802,136 A | 9/1998 | Carol |
| 5,818,902 A | 10/1998 | Yu |
| 5,835,558 A | 11/1998 | Maschke |
| 5,842,987 A | 12/1998 | Sahadevan |
| 5,848,126 A | 12/1998 | Fujita et al. |
| 5,851,182 A | 12/1998 | Sahadevan |
| 5,859,891 A | 1/1999 | Hibbard |
| 5,877,501 A | 3/1999 | Ivan et al. |
| 5,912,943 A | 6/1999 | Deucher et al. |
| 5,926,521 A | 7/1999 | Tam |
| 5,929,449 A | 7/1999 | Huang |
| 5,949,811 A | 9/1999 | Baba et al. |
| 5,956,382 A | 9/1999 | Wiener-Avnear et al. |
| 5,960,055 A | 9/1999 | Samarasekera et al. |
| 5,999,587 A | 12/1999 | Ning et al. |
| 6,031,888 A | 2/2000 | Ivan et al. |
| 6,038,283 A | 3/2000 | Carol et al. |
| 6,041,097 A | 3/2000 | Roos et al. |
| 6,052,430 A | 4/2000 | Siochi et al. |
| 6,075,836 A | 6/2000 | Ning |
| 6,078,638 A | 6/2000 | Sauer et al. |
| 6,104,778 A | 8/2000 | Murad |
| 6,104,780 A | 8/2000 | Hanover et al. |
| 6,108,400 A | 8/2000 | Siochi |
| 6,113,264 A | 9/2000 | Watanabe |
| 6,134,296 A | 10/2000 | Siochi |
| 6,142,925 A | 11/2000 | Siochi et al. |
| 6,144,875 A | 11/2000 | Schweikard et al. |
| 6,148,058 A | 11/2000 | Dobbs |
| 6,152,598 A | 11/2000 | Tomisaki et al. |
| 6,170,102 B1 | 1/2001 | Kreuzer |
| 6,200,024 B1 | 3/2001 | Negrelli |
| 6,219,403 B1 | 4/2001 | Nishihara |
| 6,219,441 B1 | 4/2001 | Hu |
| 6,222,901 B1 | 4/2001 | Meulenbrugge et al. |
| 6,240,161 B1 | 5/2001 | Siochi |
| 6,260,005 B1 | 7/2001 | Yang et al. |
| 6,269,141 B1 | 7/2001 | Proksa et al. |
| 6,269,143 B1 | 7/2001 | Tachibana |
| 6,278,766 B1 | 8/2001 | Kooy et al. |
| 6,285,739 B1 | 9/2001 | Rudin et al. |
| 6,292,526 B1 | 9/2001 | Patch |
| 6,307,914 B1 | 10/2001 | Kunieda et al. |
| 6,314,159 B1 | 11/2001 | Siochi |
| 6,318,892 B1 | 11/2001 | Suzuki et al. |
| 6,325,537 B1 | 12/2001 | Watanabe |
| 6,325,758 B1 | 12/2001 | Carol et al. |
| 6,330,300 B1 | 12/2001 | Siochi |
| 6,335,961 B1 | 1/2002 | Wofford et al. |
| 6,345,114 B1 | 2/2002 | Mackie et al. |

(56) References Cited

U.S. PATENT DOCUMENTS

| | | |
|---|---|---|
| 6,349,129 B1 | 2/2002 | Siochi |
| 6,353,222 B1 | 3/2002 | Dotan |
| 6,370,421 B1 | 4/2002 | Williams et al. |
| 6,381,302 B1 | 4/2002 | Berestov |
| 6,385,286 B1 * | 5/2002 | Fitchard et al. ............ 378/65 |
| 6,385,288 B1 | 5/2002 | Kanematsu |
| 6,385,477 B1 | 5/2002 | Werner et al. |
| 6,393,096 B1 | 5/2002 | Carol et al. |
| 6,405,072 B1 * | 6/2002 | Cosman ............ 600/426 |
| 6,411,675 B1 | 6/2002 | Llacer |
| 6,429,578 B1 | 8/2002 | Danielsson et al. |
| 6,435,715 B1 | 8/2002 | Betz et al. |
| 6,438,202 B1 | 8/2002 | Olivera et al. |
| 6,445,766 B1 | 9/2002 | Whitham |
| 6,463,122 B1 | 10/2002 | Moore |
| 6,473,490 B1 | 10/2002 | Siochi |
| 6,480,565 B1 | 11/2002 | Ning |
| 6,490,476 B1 | 12/2002 | Townsend et al. |
| 6,502,261 B1 | 1/2003 | Harwood |
| 6,504,892 B1 | 1/2003 | Ning |
| 6,508,586 B2 | 1/2003 | Oota |
| 6,560,311 B1 | 5/2003 | Shepard et al. |
| 6,590,953 B2 | 7/2003 | Suzuki et al. |
| 6,611,700 B1 | 8/2003 | Vilsmeier et al. |
| 6,618,467 B1 | 9/2003 | Ruchala et al. |
| 6,621,889 B1 | 9/2003 | Mostafavi |
| 6,640,364 B1 | 11/2003 | Josephson et al. |
| 6,661,870 B2 | 12/2003 | Kapatoes et al. |
| 6,665,554 B1 * | 12/2003 | Charles et al. ............ 600/427 |
| 6,735,277 B2 | 5/2004 | McNutt et al. |
| 6,744,848 B2 | 6/2004 | Stanton et al. |
| 6,769,806 B2 | 8/2004 | Moyers |
| 6,800,858 B1 | 10/2004 | Seppi |
| 6,841,782 B1 | 1/2005 | Balan et al. |
| 6,842,502 B2 | 1/2005 | Jaffray et al. |
| 6,865,254 B2 | 3/2005 | Nafstadius |
| 6,888,919 B2 | 5/2005 | Graf |
| 6,914,959 B2 | 7/2005 | Bailey et al. |
| 6,959,266 B1 | 10/2005 | Mostafavi |
| 6,973,202 B2 | 12/2005 | Mostafavi |
| 6,980,679 B2 | 12/2005 | Jeung |
| 7,008,105 B2 | 3/2006 | Amann et al. |
| 7,054,410 B2 | 5/2006 | Zentai |
| 7,095,028 B2 | 8/2006 | Mollov |
| 7,251,845 B2 | 8/2007 | Schaller et al. |
| 7,328,055 B2 | 2/2008 | Bonutti |
| 7,640,607 B2 | 1/2010 | Guertin et al. |
| 7,649,981 B2 | 1/2010 | Seppi |
| 7,945,021 B2 | 5/2011 | Shapiro et al. |
| 8,116,430 B1 | 2/2012 | Shapiro et al. |
| 2001/0001807 A1 | 5/2001 | Green |
| 2001/0008271 A1 | 7/2001 | Ikeda et al. |
| 2002/0006182 A1 | 1/2002 | Kim et al. |
| 2002/0066860 A1 | 6/2002 | Possin |
| 2002/0077749 A1 | 6/2002 | Doi |
| 2002/0080912 A1 | 6/2002 | Mackie et al. |
| 2002/0130279 A1 * | 9/2002 | Jain et al. ............ 250/494.1 |
| 2002/0179812 A1 | 12/2002 | Kochi et al. |
| 2002/0191734 A1 | 12/2002 | Kojima et al. |
| 2002/0193685 A1 * | 12/2002 | Mate et al. ............ 600/424 |
| 2003/0007601 A1 | 1/2003 | Jaffray et al. |
| 2003/0048868 A1 | 3/2003 | Bailey et al. |
| 2004/0024300 A1 | 2/2004 | Graf |
| 2004/0030246 A1 | 2/2004 | Townsend et al. |
| 2004/0034438 A1 | 2/2004 | Uematsu |
| 2004/0057557 A1 | 3/2004 | Nafstadius |
| 2004/0167398 A1 | 8/2004 | Flohr et al. |
| 2004/0210126 A1 | 10/2004 | Hajaj et al. |
| 2004/0220467 A1 | 11/2004 | Bonutti |
| 2004/0254773 A1 * | 12/2004 | Zhang et al. ............ 703/11 |
| 2004/0260176 A1 | 12/2004 | Wollenweber et al. |
| 2005/0053267 A1 | 3/2005 | Mostafavi |
| 2005/0054916 A1 | 3/2005 | Mostafavi |
| 2005/0080332 A1 | 4/2005 | Shiu et al. |
| 2005/0082491 A1 | 4/2005 | Seppi |
| 2005/0138732 A1 | 6/2005 | Erbel et al. |
| 2005/0197564 A1 * | 9/2005 | Dempsey ............ 600/411 |
| 2006/0113482 A1 | 6/2006 | Pelizzari et al. |
| 2006/0118736 A1 | 6/2006 | Moriyama et al. |
| 2006/0193435 A1 | 8/2006 | Hara et al. |

FOREIGN PATENT DOCUMENTS

| | | |
|---|---|---|
| DE | 3828639 A1 | 3/1989 |
| DE | 4223488 A1 | 1/1994 |
| DE | 19614643 A1 | 10/1997 |
| DE | 19800946 | 7/1999 |
| EP | 0062941 A1 | 10/1982 |
| EP | 0062941 B1 | 9/1984 |
| EP | 0205720 A1 | 12/1986 |
| EP | 0283083 A1 | 9/1988 |
| EP | 0480035 A1 | 4/1992 |
| EP | 0480035 B1 | 11/1994 |
| EP | 713677 A1 | 5/1996 |
| EP | 656797 B1 | 9/1998 |
| EP | 0922943 A2 | 6/1999 |
| EP | 0948930 A1 | 10/1999 |
| EP | 810006 B1 | 8/2000 |
| EP | 1095628 | 5/2001 |
| EP | 965104 B1 | 9/2001 |
| EP | 471455 B2 | 4/2002 |
| EP | 1389479 A1 | 2/2004 |
| FR | 2269745 A1 | 11/1975 |
| FR | 2551664 A1 | 3/1985 |
| GB | 1290425 A | 9/1972 |
| GB | 1328033 A | 8/1973 |
| GB | 2120060 A | 11/1983 |
| GB | 2393373 A | 3/2004 |
| JP | 58-94835 | 6/1983 |
| JP | S63-294839 A | 12/1988 |
| JP | 1040069 A | 2/1989 |
| JP | 1040069 A | 2/1989 |
| JP | H011-62682 A | 6/1989 |
| JP | HO1 1-62682 A | 6/1989 |
| JP | 50-57028 | 3/1993 |
| JP | 59000076 A | 1/1994 |
| JP | H06-79006 A | 3/1994 |
| JP | H06-339541 A | 12/1994 |
| JP | H07-255717 A | 10/1995 |
| JP | 9239044 A | 9/1997 |
| JP | 9239044 A | 9/1997 |
| JP | 9327453 A | 12/1997 |
| JP | H10-113400 A | 5/1998 |
| JP | H10-511595 A | 11/1998 |
| JP | H10-328318 A | 12/1998 |
| JP | H11-99148 | 4/1999 |
| JP | H11-160440 A | 6/1999 |
| JP | 2000116638 A | 4/2000 |
| JP | 2000116638 A | 4/2000 |
| JP | 2000140137 A | 5/2000 |
| JP | 2000140137 A | 5/2000 |
| JP | 2000152927 | 6/2000 |
| JP | 2000317000 A | 11/2000 |
| JP | 2001029489 A | 2/2001 |
| JP | 2001029491 A | 2/2001 |
| JP | 2001095793 A | 4/2001 |
| JP | 2001120528 A | 5/2001 |
| WO | WO 85/03212 A1 | 8/1985 |
| WO | WO 90/14129 | 11/1990 |
| WO | WO 90/14129 | 11/1990 |
| WO | WO 92/00567 A1 | 1/1992 |
| WO | WO 92/02277 A1 | 2/1992 |
| WO | WO 92/20202 A1 | 11/1992 |
| WO | WO 95/00204 A1 | 1/1995 |
| WO | WO 97/13552 | 4/1997 |
| WO | WO 97/42522 | 11/1997 |
| WO | WO 98/52635 | 11/1998 |
| WO | WO 99/03397 A1 | 1/1999 |
| WO | WO 99/48558 A1 | 9/1999 |
| WO | WO 00/15299 A1 | 3/2000 |
| WO | WO 01/60236 A2 | 8/2001 |
| WO | WO 02/13907 A1 | 2/2002 |
| WO | WO 02/24277 A1 | 3/2002 |
| WO | WO 02/061680 A2 | 8/2002 |

(56) References Cited

FOREIGN PATENT DOCUMENTS

| WO | 03/032838 A2 | 4/2003 |
|---|---|---|
| WO | 2004/030761 A1 | 4/2004 |
| WO | 2005/099578 A2 | 10/2005 |
| WO | 2006/034973 A1 | 4/2006 |

OTHER PUBLICATIONS

International Search Report and Written Opinion dated Nov. 28, 2006 for PCT Application No. PCT/US2006/016845.
Office Action dated Jul. 21, 2009 for U.S. Appl. No. 11/415,866.
Office Action dated Feb. 3, 2009 for U.S. Appl. No. 11/415,866.
Office Action dated Aug. 6, 2008 for U.S. Appl. No. 11/415,965.
Office Action dated Feb. 5, 2009 for U.S. Appl. No. 11/415,965.
Advisory Action dated Jul. 10, 2009 for U.S. Appl. No. 11/415,965.
Advisory Action dated May 28, 2009 for U.S. Appl. No. 11/415,965.
Office Action dated Sep. 18, 2008 for U.S. Appl. No. 11/415,974.
Office Action dated May 8, 2009 for U.S. Appl. No. 11/415,974.
Advisory Action dated Jul. 23, 2009 for U.S. Appl. No. 11/415,974.
Written Opinion of the International Searching Authority dated Aug. 29, 2007 for PCT Application No. PCT/US2006/016845.
http://www.dynamic-living.com/product/alternating-pressure-pump-and-pad/; "Alternating Pressure Pump and Pad" Retrieval date: Nov. 25, 2008.
http://www.preventpressuresores.com/index.html; "Active Massage Wheelchair Seating System" CCPM Technology (Computer Controlled Pressure Management); Retrieval date: Nov. 25, 2008.
http://www.alltimemedical.com/category.html?cid=101; "Pressure Reduction" All Time Medical; Retrieval date: Nov. 25, 2008.
http://answers.google.com/answers/threadview?id=522239; "Google Answers: Mattress Replacement for Wound Care" (i.e. "bed sores", ect.); Google Question; Retrieval date: Nov. 25, 2008.
Non-Final Office Action dated Jun. 21, 2010 for U.S. Appl. No. 11/415,866.
Office Action dated Dec. 7, 2010 for U.S. Appl. No. 11/415,866.
Notice of Allowance dated Feb. 17, 2011 for U.S. Appl. No. 11/415,866.
U.S. Appl. No. 10/454,754, filed on Jun. 3, 2003 Titled "Method and System for Predictive Physiological Gating of Radiation Therapy".
Non-final Office Action dated Nov. 6, 2012, for U.S. Appl. No. 13/164,698.
Shirazi et al., A cone-beam megavoltage CT scanner for treatment verification in conformal radiotherapy, 1998, pp. 319-328.
Hartson, M. et al., Comparison of CT numbers determined by a simulator CT & a diagnostic scanner, 1995, pp. 37-45.
Nishiki M., X-ray detector in IT era—FPD : Flat Panel Detector, 2001, pp. 1-2.
Boyer A. et al., Intensity-Modulated Radiotherapy: Current Status and Issues of Interest, 2001, pp. 880-914.
Wong J. et al., On-line Readiotherapy Imaging with an Array of Fiber-Optic Image Reducers, 1990, pp. 1477-1484.
Ying X. et al., A multiray model for calculating electron pencil beam distribution, 1988, pp. 662-671.
Ying X., Photon dose perturbations due to small inhomogeneities, 1987, pp. 78-83.
Yu C. X., Intensity-modulated arc therapy with dynamic multileaf collimation: An alternative to tomotherapy[1], 1995, pp. 1435-1449.
Cho, Paul S. et al., Cone-Beam CT for Radiotherapy Applications, 1995, pp. 1863-1883.
Keys, D. et al., A CCTV-Microcomputer Biostereometric System for Use in Radiation Therapy (Topography, Medical Physics, Tissue Compensators), 1984, pp. 3857.
Kudo et al., Feasible Cone Beam Scanning Methods for Exact Reconstruction in Three-Dimensional Tomography, 1990, pp. 2169.
Kuhn, M.H., Aim Project A2003: Computer Vision in RAdiology (COVIRA), Oct. 1994, pp. 17-31.
Kushima T. et al., New development of integrated CT simulation system for radiation therapy planning, 1993, pp. 197-213.
Kutcher, G. J. et al., Three dimensional radiation treatment planning, 1987.
Masahiro, et al., Patient Beam Positioning System Using CT Images, 1982, pp. 301-305.
Midgley, S. et al., A Feasibility Study for Megavoltage Cone Beam CT Using a Commercial EPID, 1998, pp. 155-169.
Mohan, R, et al., Intersection of shaped radiation beams with arbitrary image sections, Jun. 1987, pp. 161-168.
Nakagawa, Keiichi, M.D. et al., Megavoltage CT-Assisted Stereotactic Radiosurgery for Thoracic Tumors: Original Research in the Treatment of Thoracic Neoplasms, 2000, pp. 449-457.
Ning et al., Flat Panel Detector-Based Cone-Beam Volume CT Angiography Imaging: System Evaluation, Sep. 2000, pp. 949-963.
Ning et al., Image Intensifier-Based Volume Tomographic Angiography Imaging System: System Evaluation, 1995, pp. 280-290.
Uematsu, M. et al., A Dual Computed Tomography Linear Accelerator Unit for Stereotactic RadiationTherapy: A New Approach WithoutCranially Fixated Stereotactic Frames, 1996, pp. 587-592.
Uematsu, M. et al., Daily Positioning Accuracy of Frameless Stereotactic Radiation Therapy with a Fusion of Computed Tomography and Linear Accelerator (FOCAL) Unit: Evaluation of Z-axis with a Z-marker, Mar. 1999, pp. 337-339.
Maria Korteila, Varianin avulla sade tappaa kasvaimen tarkasti, 2000, pp. 1-8.
Jinho LimOptimization in radiation treatment planning, 2002.
"Advanced Workstation for Irregular Field Simulation and Image Matching," Copyright 1999, MDS Nordion, 7 pages.
Andrew, J. W. et al., "A video-based patient contou acquisition system for the design radiotherapy compensators," Abstract, Med Phys, May-Jun. 1989, vol. 16 (3), pp. 425-430.
Balter, J M., et al., "Daily Targeting of intrahepatic tumors for Radiotherapy", Int. J. Radiation Oncology Biol. Phys., vol. 52, No. 1, (2002), 266-271.
Brewsterfuauf, et al., "Automatic generation of beam apertures," Abstract, Medical Physics, 1993, vol. 20, pp. 1337, 1342.
Cho, P S., et al., "Cone-Beam CT for Radiotherapy Applications", Phys. Med. Biol, vol. 40, (1995), 1863-1883.
Drake, D G., et al., "Characterization of a Fluoroscopic Imaging System for kV and MV Radiography", Med. Phys., vol. 27, No. 5, (May 2000), 898-905.
Elliot, et al., "Interactive Imagine Segmentation for Radiation Treatment Planning", Abstract, IBM Systems Journal, vol. 31, No. 4, (1992), 620-634.
EPO, European Search Report in European Application No. 07 86 2095, Dec. 2, 2013, 11 pages.
European Search Report mailed Jan. 21, 2011 for European Application No. 03786979.9.
Fahrig, R , et al., "Three-Dimensional Computed Tomographic Reconstruction Using a C-Arm Mounted XRII: Image Based Correction of Gantry Motion Nonidealities", Med. Phys., vol. 27, No. 1, (Jan. 2000), 30-38.
Feldkamp, L A, et al., "Practical Cone-Beam Algorithm", J. Opt. Soc. Am. A, vol. 1, No. 6, (Jun. 1984), 612-619.
Gademann, et al., "Three-dimensional radiation planning. Studies on clinical integration," Abstract, Strahlenther Onkol, 1993, vol. 169 (3), pp. 159-167.
Groh, B A., et al., "A Performance Comparison of Flat-Panel Imager-Based MV and kV Conebeam CT", Med. Phys., vol. 29, No. 6, (Jun. 2002), 967-975.
Hara et al., "Radiotherapeutic System," 00480035/EP-B1, Citation from World Patent, 1994, 1 page.
Jaffray et al., "Flat-Panel Cone-Beam Computed Tomography for Image-Guided Radiation Therapy," Int. J. Radiation Oncology Biol. Phys., vol. 53, No. 5 (2002), pp. 1337-1349.
Jaffray, D. A. et al., SPIE vol. 3659, 204-214, 1999.
Jaffray, D A., et al., "A Radiographic and Tomographic Imaging System Integrated into a Medical Linear Accelerator for Localization of Bone and Soft- Tissue Targets", Int. J. Radiation Oncology Biol. Phys., vol. 45, No. 3, (1999), 779-789.
Jaffray, D A., et al., "Cone-Beam Computed Tomography with a Flat-Panel Imager: Initial Performance Characterization", Med. Phys., col. 27, No. 6, (Jun. 2000), 1311-1323.

(56) References Cited

OTHER PUBLICATIONS

Jaffray, et al., "Cone-beam CT: applications in image-guided external beam radiotherapy and brachytherapy," Engineering in Medicine and Biology Society, Proceedings of the 22nd Annual International Conference of the IEEE, Jul. 2000, vol. 3, p. 2044.
Keys, D, et al., "A CCTV-Microcomputer Biostereometric System for Use in Radiation Therapy (Topography, Medical Physics, Tissue Compensators)", Abstract, Energy Science and Technology, vol. 45-12B, (1984), 3857.
Kudo et al., "Feasible cone beam scanning methods for exact reconstruction in three-dimensional tomography," J. Opt. Soc. Am. A; 7, 2169 (1990).
Kuhn, MH , "AIM Project A2003: Computer Vision in Radiology (COVIRA)", Abstract, Computer Methods and Programs in Biomedicine, vol. 45, No. 1-2, (Oct. 1994), 17-31.
Kushima, GJ, et al., "New Development of Integrated CT Simulation System for Radiation Therapy Planning", Abstract. Kobe J. Med. Sci., vol. 9, No. 5-6, (Dec. 1993), 17-213.
Kutcher, et al., "Three dimensional radiation treatment planning," Abstract (1998), Dosimetry in radiotherapy, vol. 2, Proceedings of an international symposium held in Vienna, Austria, Aug.-Sep. 1987.
Masahiro et al., "Patient Beam Positioning System Using CT Images", Phys. Med. Biol., 1982, vol. 27, No. 2, pp. 301-305, printed in Great Britain.
Midgley, et al., "A Feasibility Study for Megavoltage Cone Beam CT Using a Commercial EPID", Phys. Med. Biol. 43, United Kingdom, (1998), 155-169.
Mohan, et al., "Intersection of shaped radiation beams with arbitrary image sections," Abstract, Comput Methods Programs Biomed, Jun. 1987, vol. 24, pp. 161-168.
Mosleh-Shirazi, M A., et al., "A Cone-Beam Megavoltage CT Scanner for Treatment Certification in Conformal Radiotherapy", Radiotherapy and Oncology, vol. 48, (1998), 319-328.
Nakagawa, K , et al., "Megavoltage CT-Assisted Stereotactic Radiosurgery for Thoracic Tumors: Original Research in the Treatment of Thoracic Neoplasms", Int. J. radiation ongology biol. phys., col. 48, No. 2, (2000), 449-457.
Ning et al., "Flat Panel Detector-Based Cone-Beam Volume CT Angiography Imaging: System Evaluation," IEEE Transactions on Medical Imaging, vol. 19, No. 9, Sep. 2000, 949-963.
Ning et al., SPIE vol. 3659, 192-203, 1999.
Ning, et al., "Image intensifier-based Volume tomographic angiography imaging system: system evaluation," SPIE, Medical Imaging 1995, vol. 2432, pp. 280-290.
PCT, International Search Report and Written Opinion in PCT Application PCT/US07/241 03, May 5, 2008, 8 pages.
Pisani, L , et al., "Setup Error in radiotherapy: On-line Correction using Electronic Kilovoltage and Megavoltage Radiographs", Int. J. Radiation Oncology Biol. Phys., vol. 47, No. 3, (2000), 825-839.
Ragan, "Correction for Distortion in a Beam Outline Transfer Device in Radiotherapy CT-Based Simulation," Med. Phys. 20 (1), Jan./Feb. 1993, pp. 179-185.
Redpath, et al., "Use of a simulator and treatment planning computer as a CT scanner for radiotherapy planning," Abstract, Proceedings—Eighth International Conference on the Use of Computers in Radiation Therapy held in Toronto, Canada, 1984, pp. 281-287. IEEE, New York, NY.
Reynolds, et al., "An algorithm for three-dimensional visualization of radiation therapy beams," Abstract, Med Phys, Jan.-Feb. 1988, vol. 15 (1), pp. 24-28.
Rizo et al., "Comparison of two three-dimensional x-ray cone-beam-reconstruction algorithms with circular source trajectories," J. Opt. Soc. Am. A, 10, 1639 (1991).
Ruchala, K J., et al., "Megavoltage CT Tomography System", Phy. Med. Biol., vol. 44, (1999), 2597-2621.
Siewerdsen et al., Med. Phys. 26, 1624-1641, 1999.
Siewerdsen et al., Med. Phys. 26, 2635-2647, 1999.
Siewerdsen, J H., et al., "Cone-Beam Computed Tomography with a Flat-Panel Imager: Magnitude and Effect of X-Ray Scatter", Med. Phys., vol. 28, No. 2, (Feb. 2001), 220-231.
Siewerdsen, J H., et al., "Optimization of X-Ray Imaging Geometry (With Specific Application to Flat-Paneled Cone-Beam Computed Tomography)", Med. Phys., vol. 27, No. 8, (Aug. 2000), 1903-1914.
Supplementary European Search Report mailed Jan. 12, 2011; EP Appln No. 03786979.9; 3 pages.
Swindell, W , et al., "Computed Tomography with a Linear Accelerator with Radiotherapy Applications", Med. Phys., vol. 10, No. 4, (Jul./Aug. 1983), 416-420.
Uematsu, M , et al., "A Dual Computed Tomography Linear Accelerator Unit for Stereotactic Radiation Therapy: A New Approach Without Cranially Fixated Stereotactic Frames", Int. J. Radiation Oncology Biol. Phys., vol. 35, No. 3, (1996), pp. 587-592.
Uematsu, M , et al., "Daily Positioning Accuracy of Frameless Stereotactic Radiation Therapy with a Fusion of Computed Tomography and Linear Accelerator (FOCAL) Unit: Evaluation of Z-axis with a Z-marker", Radiotherapy and Oncology, vol. 50, No. 3, (Mar. 1999), 337-339.
Uematsu, M , et al., "Infractional Tumor Position Stability During Computed Tomography (CT)—Guided Frameless Seterotactic Radiation Therapy for Lung or Liver cancers with a Fusion of CT and Linear Accelerator (FOCAL) Unit", Int. J. Radiation Oncology Biol. Phys, vol. 48, No. 2, (2000), 443-448.
Varian Medical Systems, Inc., Communication pursuant to Article 94(3) EPC, EP Application No. 03 786 979.9-1657, dated Jan. 30, 2014, 8 pages.
Yan et al., "Derivation and analysis of a filtered backprojection algorithm for cone beam projection," IEEE Trans. Medical Imaging, 10, pp. 462-472 (1991).
Final Office Action dated Sep. 24, 2015 for related U.S. Appl. No. 13/164,698.
Non-final Office Action dated Dec. 3, 2013, for U.S. Appl. No. 13/164,698.
Final Office Action dated May 22, 2013, for U.S. Appl. No. 13/164,698.
Final Office Action dated Jul. 9, 2014, for U.S. Appl. No. 13/164,698.
Advisory Action dated Oct. 3, 2014 for U.S. Appl. No. 13/164,698.
Non-final Office Action dated Feb. 9, 2015 for U.S. Appl. No. 13/164,698.
Wu, Q. et al., Dynamic splitting of large intensity-modulated fields, Jul. 2000, pp. 1731-1740.
Verfaillie, G. et al., Russian Doll Search for Solving Constraints Optimization Problems, 1996, pp. 181-187.
Carey, G. F., Computational Grids: Generations, Adaptation & Solution Strategies, 1997.
van Herk et al., Automatic three-dimensional correlation of CT-CT, CT-MRI, and CT-SPECT using chamfer matching, Medical Physics 21(7), Jul. 1994, pp. 1163-1178.
Woods et al., MRI-PET Registration with Automated Algorithm, Journal of Computer Assisted Tomography 17(4), Jul./Aug. 1993, pp. 536-546.
L. Antonuk, Electronic portal imaging devices: a review and historical perspective of contemporary technologies and research, Mar. 1, 2002, pp. R31-R65.
Agostinelli, S. et al., A prototype 3D CT extension for radiotherapy simulators, 2001, pp. 11-21.
Cho et al., Digital radiotherapy simulator, 1998, pp. 1-7.
Hartson, M. et al., Comparison of CT mumbers determined by a simulator CT & a diagnostic scanner, 1995, pp. 37-45.
Yu, C., Intensity Modulated Arc Therapy: Technology and Clinical Implementation, Sep. 1995, pp. 1-14.
Chin et al., Dose Optimization with Computer-Controlled Gantry Rotation, Collimator Motion and Dose-Rate Variation, May 1983, pp. 723-729.
Cotrutz et al., Intensity modulated arc therapy (IMAT) with centrally blocked rotational fields, 2000, pp. 2185-2206.
Yu, C. Intensity-modulated arc therapy with dynamic multileaf collimation: an alternative to tomotherapy, 1995, pp. 1435-1449.
Nakagawa T. et al., Accuracy improvement of irradiation position and new trend, 2001, pp. 102-105.

(56) References Cited

OTHER PUBLICATIONS

Nishiki M., X-ray detector in IT era—FPD: Flat Panel Detector, 2001, pp. 1-2.
Watanabe, Y., Development of corn beam X-ray CT system, Oct. 2002, pp. 778-783.
The Stanford medical linear accelerator. II. Installation and physical measurements, 1959, Weissbluth, M., C. J., Karzmark et al., 242-253.
Akanuma, A., et al., New Patient Set Up in Linac-CT Radiotherapy System—First Mention of a Hybrid CT-Linac System, 1984, pp. 465-467.
Schewe, J. E. et al., A room-based diagnostic imaging system for measurement of patient setup, Dec. 1998, pp. 2385-2387.
Antonuk L. et al., Strategies to improve the signal and noise performance of active matrix, flat-panel imagers for diagnostic x-ray applications, Feb. 2000, pp. 289-306.
Bassett P., An Interactive Computer System for Studying Human Mucociliary Clearance, 1979, pp. 97-105.
Bissonnette J. et al., Optimal radiographic magnification for portal imaging, Sep. 1994, pp. 1435-1445.
Boyer A. et al., Intensity-Modulated Radiotherapy: Current Status and Issues of Interest, 2001,pp. 880-914.
Brown A. et al., Three-Dimensional Photon Treatment Planning for Hodgkin's Disease, May 1992, pp. 205-215.
Cheng A. et al., Systematic verification of a three-dimensional electron beam dose calculation algorithm, 1996, pp. 685-693.
Cullity B., Elements of X-Ray Diffraction, 1978, pp. 6-12.
Dieu L. et al., Ion Beam Sputter-Deposited SiN/TiN Attenuating Phase-Shift Photoblanks, 2001, pp. 810-817.
Du M. et al., A Multileaf Collimator Field Prescription Preparation System for Conventional Radiotherapy, 1994, pp. 707-714.
Du M. et al., A Multileaf Collimator Field Prescription Preparation System for Conventional Radiotherapy, 1995, pp. 513-520.
El-Mohri Y. et al., Relative dosimetry using active matrix flat-panel imager (AMFPI) technology, 1999, pp. 1530-1541.
Frazier A. et al., Dosimetric Evaluation of the Conformation of the Multileaf Collimator to Irregularly Shaped Fields, 1995, pp. 1229-1238.
Frazier A. et al., Effects of Treatment Setup Variation on Beam's Eye View Dosimetry for Radiation Therapy Using the Multileaf Collimator vs. the Cerrobend Block, 1995, pp. 1247-1256.
Graham M. et al., A Method to Analyze 2-Dimensional Daily Radiotherapy Portal Images from an On-Line Fiber-Optic Imaging System, 1991, pp. 613-619.
Halverson K. et al., Study of Treatment Variation in the Radiotherapy of Head and Neck Tumors Using a Fiber-Optic On-Line Radiotherapy Imaging System, 1991, pp. 1327-1336.
Harms W. et al., A software tool for the quatitative evaluation of 3D dose calculation algorithms, 1998, pp. 1830-1836.
Jaffray D. et al., Activity distribution of a cobalt-60 teletherapy source, 1991, pp. 288-291.
Jaffray D. et al., Conebeam Tomographic Guidance of Radiation Field Placement for Radiotherapy of the Prostate, 1998, pp. 1-32.
Jaffray D. et al., X-ray scatter in megavoltage transmission radiography: Physical characteristics and influence on image quality, Jan. 1994, pp. 45-60.
Jaffray D. et al., X-ray sources of medical linear accelerators: Focal and extra-focal radiation, 1993, pp. 1417-1427.
Kestin L. et al., Improving the Dosimetric Coverage of Interstitial High-Dose-Rate Breast Implants, 2000, pp. 35-43.
Kestin L. et al., Intensity Modulation to Improve Dose Uniformity With Tangential Breast Radiotherapy: Initial Clinical Experience, 2000, pp. 1559-1568.
Kini V. et al., Use of Three-Dimensional Radiation Therapy Planning Tools and Intraoperative Ultrasound to Evaluate High Dose Rate Prostate Brachytherapy Implants, 1999, pp. 571-578.
Laughlin J. et al., Evaluation of High Energy Photon External Beam Treatment Planning: Project Summary, 1991, pp. 3-8.

Lockman et al., Estimating the dose variation in a volume of interest with explicit consideration of patient geometric variation, Sep. 2000, pp. 2100-2108.
Martinez A. et al., Improvement in Dose Escalation Using the Process of Adaptive Radiotherapy Combined with Three-Dimensional Conformal or Intensity-Modulated Beams for Prostate Cancer, 2001, pp. 1226-1234.
Masterson M. et al., Interinstitutional Experience in Verification of External Photon Dose Calculations, 1991, pp. 37-58.
Michalski J. et al., An Evaluation of Two Methods of Anatomical Alignment of Radiotherapy Portal Images, 1993, pp. 1199-1206.
Michalski J. et al, Prospective Clinical Evaluation of an Electronic Portal Imaging Device, 1996, pp. 943-951.
Michalski J. et al., The Use of On-line Image Verification to Estimate the Variation in Radiation Therapy Dose Delivery, 1993, pp. 707-716.
Milliken B. et al., Verification of the omni wedge technique, 1998, pp. 1419-1423.
Mohan, R., Three Dimensional Dose Calculations for Radiation Treatment Planning, 1991, pp. 25-36.
Oldham M. et al., Practical aspects of in situ 16O (y,n) 15O activation using a conventional medical accelerator for the purpose of perfusion imaging, Aug. 2001, pp. 1669-1678.
Perera H. et al., Rapid Two-Dimensional Dose Measurement in Brachytherapy Using Plastic Scintillator Sheet: Linearity, Signal-to-Noise Ratio, and Energy Response Characteristics, 1992, pp. 1059-1069.
Purdy J. et al., State of the Art of High Energy Photon Treatment Planning, 1987, pp. 4-24.
Sharpe M. et al., Compensation of x-ray beam penumbra in conformal radiotherapy, Aug. 2000, pp. 1739-1745.
Sharpe M. et al., Monitor unit settings for intensity modulated beams delivered using a step- and-shoot approach, Dec. 2000, pp. 2719-2725.
Shiu A et al., Verification data for electron beam dose algorithms, 1992, pp. 623-636.
Sontag M. et al., State-of-the-Art of External Photon Beam Radiation Treatment Planning, 1991, pp. 9-23.
Stromberg J. et al., Active Breathing Control (ABC) for Hodgkin's Disease: Reduction in Normal Tissue Irradiation with Deep Inspiration and Implications for Treatment, 2000, pp. 797-806.
Teicher B. et al., Allosteric effectors of hemoglobin as modulators of chemotherapy and radiation therapy in vitro and in vivo, 1998, pp. 24-30.
Tepper J. et al., Three-Dimensional Display in Planning Radiation Therapy: A Clinical Perspective, 1991, pp. 79-89.
Urie M. et al., The Role of Uncertainty Analysis in Treatment Planning, 1991, pp. 91-107.
Vicini F. et al., Dose-Volume Analysis for Quality Assurance of Interstitial Brachytherapy for Breast Cancer, 1999, pp. 803-810.
Vicini F. et al., Implementation of 3D-Virtual Brachytherapy in the Management of Breast Cancer: A Description of a New Method of Interstitial Brachytherapy, 1998, pp. 629-635.
Vicini F. et al., Low-Dose-Rate Brachytherapy as the Sole Radiation Modality in the Management of Patients with Early-Stage Breast Cancer Treated with Breast-Conserving Therapy: Preliminary Results of a Pilot Trial, 1997, pp. 301-310.
Williamson J. et al., One-dimensional scatter-subtraction method for brachytherapy dose calculation near bounded heterogeneities, 1993, pp. 233-244.
Wong J. et al., Conservative management of osteoradionecrosis, Jul. 1997, pp. 16-21.
Wong J. et al., The Cumulative Verification Image Analysis Tool for Offline Evaluation of Portal Images, 1995, pp. 1301-1310.
Wong J. et al., Development of a Second-Generation Fiber-Optic On-Line Image Verification System Effect of small Inhomogeneities on dose in a cobalt-60 beam, 1993, pp. 311-320.
Wong J. et al., Effect of small Inhomogeneities on does in a cobalt-60 beam, 1981, pp. 783-791.
Wong J. et al., On methods of inhomogeneity corrections for photon transport, 1990, pp. 807-814.
Wong J. et al., A new approach to CT pixel-based photon dose calculations in heterogeneous media, 1983, pp. 199-208.

(56) References Cited

OTHER PUBLICATIONS

Wong J. et al., On-line image verification in radiation therapy: an early USA experience, 1993, pp. 43-54.
Wong J. et al., On-line Radiotherapy Imaging with an Array of Fiber-Optic Image Reducers, 1990, pp. 1477-1484.
Wong J. et al., Portal Dose Images I: Quantitative Treatment Plan Verification, 1990, pp. 1455-1463.
Wong J. et al., Reconsideration of the power-law (Batho) equation for inhomogeneity corrections, 1982, pp. 521-530.
Wong J. et al., Role of Inhomogeneity Corrections in Three-Dimensional Photon Treatment Planning, 1991, pp. 59-69.
Wong J. et al., Second scatter contribution to dose in a cobalt-60 beam, 1981, pp. 775-782.
Wong J. et al., Treatment Verifications and Patient Dose Estimations Using Portal Dose Imaging, 1988, pp. 213-225.
Wong J. et al., The Use of Active Breathing Control (ABC) to Reduce Margin for Breathing Motion, 1999, pp. 911-919.
Wu Y. et al., Implementing multiple static field delivery for intensity modulated beams, Nov. 2001, pp. 2188-2197.
Yan D. et al., The Influence of Interpatient and Intrapatient Rectum Variation on External Beam Treatment of Prostate Cancer, 2001, pp. 1111-1119.
Yan D. et al., A Model to Accumulate Fractionated Dose in a Deforming Organ, 1999, pp. 665-675.
Yan D. et al., A New Model for "Accept or Reject" Strategies in Off-Line and On-Line Megavoltage Treatment Evaluation, 1995, pp. 943-952.
Ying X. et al., Portal Dose Images II: Patient Dose Estimation, 1990, pp. 1465-1475.
Yu C. et al., A method for implementing dynamic photon beam intensity modulation using independent jaws and a multileaf collimator, 1995, pp. 769-787.
Yu et al., A multiray model for calculating electron pencil beam distribution, 1988, pp. 662-671.
Yu et al., Photon dose perturbations due to small inhomogeneities, 1987, pp. 78-83.
Yu C. et al., Photon does calculation incorporating explicit electron transport, Jul. 1995, pp. 1157-1166.
MDS Nordion, Advanced Workstation for Irregular Field Simulation and Image Matching, 1999, 7 pages.
Bortfeld et al., Clinically relevant intensity modulation optimization using physical criteria, 1997, pp. 1-4.
Brewster et al., Automatic generation of beam apertures, 1993, pp. 1337-1342.
Chui, C.S. et al., Dose calculation for photon beams with intensity modulation generated by dynamic jaw or multileaf collimations, 1994, pp. 1237-1244.
I.M.R.T.C.W. Group, Intensity-modulated radiotherapy: Current status and issues of interest, 2001, pp. 880-914.
Kirkpatrick, S. et al., Optimization by simulated annealing, 1983, pp. 671-680.
Niemierko, A. et al., Random sampling for evaluation treatment plans, 1990, pp. 753-762.
Spirou et al., A Gradient Inverse Planning Algorithm with Dose-Volume Contraints, 1998, pp. 321-333.
Spirou et al., Generation of Arbitrary Intensity Profiles by Dynamic Jaws or Multileaf Collimators, 1994, pp. 1031-1041.
Tervo et al., A Model for the Control of a Multileaf Collimator in Radiation Therapy Treatment Planning, 2000, pp. 1875-1895.
W. De Gersem et al., Leaf position optimization for step-and-shoot IMRT, 2001, pp. 1371-1388.
Wu et al., Algorithm and Functionality of an Intensity Modulated Radiotherapy Optimization System, 2000, pp. 701-711.
Xia et al., Multileaf Collimator Leaf Sequencing Algorithm for Intensity Modulated Beams with Multiple Static Segments, 1998, pp. 1424-1434.
Zellars, R.C. et al., Prostate position late in the course of external beam therapy: Patterns and predictors, 2000, pp. 655-660.
Rostkowska, J. et al., Physical and Dosimetric Aspects of QualityAssurance in Sterotactic Radiotherapy, 2001, pp. 53-54.

Sidhu, K. et al., Optimization of Conformal Thoracic Radiotherapy Plance While Using Cone-Beam CT Imaging for Treatment Verification, 2001, pp. 175-176.
Smith, R. et al., Development of cone beam CT for radiotherapy treatment planning, 2001, pp. S115.
Nag, S. et al., Intraoperative Planning and Evaluation of Permanent Prostate Brachytherapy: Report of the American Brachytherapy Society, 2001, pp. 1422-1430.
MacKenzie, M. and, Robinson, D.,Intensity modulated arc deliveries approximated by a large number of fixed gantry position sliding window dynamic multileaf collimator fields, 2002, pp. 2359-2365.
Bissonnette, J-P, et, al., An Alternative X-Ray Detector for Portal Imaging: High Density Glass Scintillator, 1993, pp. 36-37.
Bissonnette, J-P, et, al., Physical characterization and optimal magnification of a portal imaging system, 1992, pp. 182-188.
Colbeth, R. et al., 40× 30 cm Flat Panel Imager for Angiography, R&F, and Cone-Beam CT Applications, February pp. 94-102.
Colbeth, R. et al., Characterization of an Amorphous Silicon Fluoroscopic Imager, 1997, pp. 42-51.
Colbeth, R. et al., Characterization of a third generation, multi-mode sensor panel, Feb. 1999, pp. 491-500.
Colbeth, R. et al., A Multi-mode X-ray Imager for Medical and Industrial Applications, 1998, pp. VI-629-VI-632.
Colbeth, R. et al., Flat panel imaging system for fluoroscopy applications, Feb. 1998, pp. 376-387.
Gilblom, D. et al., Real-time x-ray imaging with flat panels, 1998, pp. 213-223.
Gilblom, D. et al., A real-time, high-resolution camera with an amorphous silicon large-area sensor, 1998, pp. 29-38.
Jaffray, D. et al., Medical linear accelerator x-ray sources: Variation with make, model, and time, 1992, pp. 174-181.
Johnsen, S. et al., Improved Clinac Electron Beam Quality, 1983, pp. 737.
Klausmeier-Brown, M.E. et al., Real-Time Image Processing in a Flat-Panel, Solid-State, Medical Fluoroscopic Imaging System, Jan. 1998, pp. 2-7.
Kubo, H., Potential and role of a prototype amorphous silicon array electronic portal imaging device in breathing synchronized radiotherapy, Nov. 1999, pp. 2410-2414.
Mallik, R. et al., Simulator Based CT: 4 Years of Experience at the Royal North Shore Hospital, Sydney, Australia, Apr. 1993, pp. 177-185.
Munro, P. et al., Megavoltage Cone-Beam Computed Tomography Using a High Quantum Efficiency Image Receptor, 2002, pp. 1340.
Munro, P. et al., A Digital Fluoroscopic Imaging Device for Radiotherapy Localization, 1990, pp. 641-649.
Munro, P., On Line Portal Imaging, 1997, pp. 114.
Ning, R. et al., Real Time Flat Panel Detector-Based Volume Tomographic Angiography Imaging: Detector Evaluation, Feb. 2000, pp. 396-407.
Munro, P. et al., Therapy imaging: limitations of imaging with high energy x-ray beams, 1987, pp. 178-184.
Wright, M. et al., Amorphous silicon dual mode medical imaging system, Feb. 1998, pp. 505-514.
Cho, Y. et al., Thermal Modelling of a Kilovoltage X-Ray Source for Portal Imaging, Jul. 2000, pp. 1856-1860.
Ebert, M. et al., 3D image guidance in radiotherapy: a feasibility study, 2001, pp. 1807-1816.
Ford, E.C. et al., Cone-beam CT with megavoltage beams and an amorphous silicon electronic portal imaging device: Potential for verification of radiotherapy of lung cancer, 2002, pp. 2913-2924.
Hunt, P. et al., Development of an IMRT quality assurance program using an amorphous silicon electronic portal imaging device, 2000, 1 page.
Mueller, K. et al., Cone-Beam Computed Tomography (CT) for a Megavoltage Linear Accelerator (LINAC) Using an Electronic Portal Imaging Device (EPID) and the Algebraic Reconstruction Technique (ART), Jul. 2000, pp. 2875-2878.
Rowbottom, C. et al., Simultaneous optimization of beam orientations and beam weights in conformal radiotherapy, 2001, pp. 1696-1702.
Simo Muinonen, Sädehoiden valmistelun optimointi fysiikan keinoin, 1995, pp. 1-166.

(56) References Cited

OTHER PUBLICATIONS

Jyrki Alakuijala, Algorithms for modeling anatomic and target volumes in image-guided neurosurgery and radiotherapy, 2001, pp. 1-121.
Intensiteettimuokattu sädehoito—uusi tekniikka parantanee hoitotuloksia, 2001, Heikki Joensuu,, Mauri Kouri, Mikko Tenhunen, pp. 389-394.
Tiina Seppälä, FiR 1 epithermal neutron beam model and dose calculation for treatment planning in neutron capture therapy, 2002, pp. 1-46.
Maria Korteila, Varianin avulla säde tappaa kasvaimen tarkasti, 2000, pp. 1-8.
Budgell, Temporal resolution requirements for intensity modulated radiation therapy delivered by multileaf collimators, 1999, pp. 1581-1596.
Xing et al, Dosimetric verification of a commercial inverse treatment planning system, 1999, pp. 463-478.
Johan Löf, Development of a general framework for optimization of radiation therapy, 2000, pp. 1-140.
Xing et al, Iterative methods for inverse treatment planning, 1996, pp. 2107-2123.
Jinho Lim Optimization in radiation treatment planning, 2002.
Podgorsak et al, Dynamic Stereotactic Radiosurgery, 1988, pp. 115-126.
Webb et al, Inverse planning with constraints to generate smoothed intensity-modulated beams, 1998, pp. 2785-2794.
Crooks et al, Linear algebraic methods applied to intensity modulated radiation therapy, 2001, pp. 2587-2606.
Digital Imaging and Communications in Medicine (DICOM) Supplement 11 Radiotherapy Objects, 1997, pp. 1-103.
Anderson, R., Software system for automatic parameter logging on Philips SL20 linear accelerator, 1995, pp. 220-222.
Berkeshev, O.S. et. al., Practical realization of a method of digital x-ray diagnostics in a scanning-type device[3], 2001, pp. 36-37.
Jaffray, et al., Cone-beam computed tomography on a medical linear accelerator using a flat-panel imager, 2000, pp. 558-560.
Karzmark, C.J., A Primer on Theory and Operation of Linear Accelerators in Radiation Therapy, Dec. 1981, pp. 1-61.
Wong, J. et al., Behandlung des Lungenkarzinoms mittels stereotaktischer Strahlentherapie unter Verwendung des weltweit ersten PRIMATOM Systems—eine Fallstudie[4], 2001, pp. 133-136.
Studholme et al., Automated three-dimensional registration of magnetic resonance and positron emission tomography brain images by multiresolution optimization of voxel similarity measures, 1997, pp. 25-35.
Andrew, J. W. et al., "A video-based patient contour acquisition system for the design radiotherapy compensators," Abstract, Med Phys, May/Jun. 1989, 16 (3), pp. 425-430.
Balter, J M., et al., "Daily Targeting of intrahepatic tumors for Radiotherapy", Int. J. Radiation Oncology Biol. Phys., vol. 52, No. 1, 2002, 266-271.
Cho, P. S., et al., "Cone-Beam CT for Radiotherapy Applications", Phys. Med. Biol, vol. 40, 1995, 1863-1883.
Drake, D G., et al., "Characterization of a Fluoroscopic Imaging System for kV and MV Radiography", Med. Phys., vol. 27, No. 5, May 2000, 898-905.
Elliot, et al., "Interactive Imagine Segmentation for Radiation Treatment Planning", Abstract, IBM Systems Journal, vol. 31, No. 4, 1992, 620-634.
Extended European Search Report dated Dec. 2, 2013, for European Patent Application No. 07 86 2095.2, 12 pages.
European Search Report mailed Jan. 21, 2011 for European Patent Application No. 03786979.9, 3 pages.
Fahrig, R , et al., "Three-Dimensional Computed Tomographic Reconstruction Using a C-Arm Mounted XRII: Image Based Correction of Gantry Motion Nonidealities", Med. Phys., 27 (1), Jan. 2000), 30-38.
Feldkamp, L A., et al., "Practical Cone-Beam Algorithm", J. Opt. Soc. Am. A, vol. 1, No. 6, Jun. 1984), 612-619.

Gademann, et al., "Three-dimensional treatment planning. Evaluations for clinical integration," Abstract, Strahlenther Onkol, 1993, vol. 169 (3), pp. 159-167. (w/ English Abstract).
Groh, B A., et al., "A Performance Comparison of Flat-Panel Imager-Based MV and kV Conebeam CT", Med. Phys., 29 (6), Jun. 2002, 967-975.
Hara, "Radiotherapeutic System," 00480035/EP-B1, Citation from World Patent, Nov. 9, 1994, 1 page.
Jaffray et al., "Flat-Panel Cone-Beam Computed Tomography for Image-Guided Radiation Therapy," Int. J. Radiation Oncology Biol. Phys., vol. 53, No. 5, 2002, pp. 1337-1349.
Jaffray, D. A. et al., Performance of a Volumetric CT Scanner Based Upong a Flat-Panel Imager, SPIE vol. 3659, 204-214, Feb. 1999.
Jaffray, D A., et al., "A Radiographic and Tomographic Imaging System Integrated into a Medical Linear Accelerator for Localization of Bone and Soft-Tissue Targets", Int. J. Radiation Oncology Biol. Phys., vol. 45, No. 3, 1999, 773-789.
Jaffray, D A., et al., "Cone-Beam Computed Tomography with a Flat-Panel Imager: Initial Performance Characterization", Med. Phys., col. 27, No. 6, Jun. 2000, 1311-1323.
Jaffray, et al., "Cone-beam CT: Applications in Image-Guided External Beam Radiotherapy and Brachytherapy," Engineering in Medicine and Biology Society, Proceedings of the 22nd Annual International Conference of the IEEE, Jul. 23-28, 2000, vol. 3, p. 2044.
Keys, D, et al., "A CCTV-Microcomputer Biostereometric System for Use in Radiation Therapy (Topography, Medical Physics, Tissue Compensators)", Abstract, Energy Science and Technology, vol. 45-12B, 1984, 3857.
Kudo et al., "Feasible cone beam scanning methods for exact reconstruction in three-dimensional tomography," J. Opt. Soc. Am. A; 7, 2169, Dec. 1990.
Kuhn, MH , "AIM Project A2003: Computer Vision in Radiology (COVIRA)", Abstract, Computer Methods and Programs in Biomedicine, vol. 45, No. 1-2, 1994, 17-31.
Kushima, GJ , et al., "New Development of Integrated CT Simulation System for Radiation Therapy Planning", Kobe J. Med. Sci., 39,, Dec. 1993, 197-213.
Kutcher, et al., "Three dimensional radiation treatment planning," 1998, Dosimetry in radiotherapy, vol. 2, Proceedings of an international symposium held in Vienna, Austria, Aug.-Sep. 1987.
Endo, Masahiro et al., "Patient Beam Positioning System Using CT Images", Phys. Med. Biol., 1982, vol. 27, No. 2, 301-305.
Midgley, et al., "A Feasibility Study for Megavoltage Cone Beam CT Using a Commercial EPID", Phys. Med. Biol. 43, 1998, 155-169.
Mohan, et al., "Intersection of shaped radiation beams with arbitrary image sections," Computer Methods Programs Biomedicine 24, 1987, 161-168.
Mosleh-Shirazi, M A., et al., "A Cone-Beam Megavoltage CT Scanner for Treatment Certification in Conformal Radiotherapy", Radiotherapy and Oncology, vol. 48, 1998, 319-328.
Nakagawa, K , et al., "Megavoltage CT-Assisted Stereotactic Radiosurgery for Thoracic Tumors: Original Research in the Treatment of Thoracic Neoplasms", Int. J. radiation oncology biol. phys., col. 48, No. 2, 2000, 449-457.
Ning et al., "Flat Panel Detector-Based Cone-Beam Volume CT Imaging: Detector Evaluation," SPIE vol. 3659, 192-203, 1999.
Ning, et al., "An Image intensifier-based volume tomographic angiography imaging system: system evaluation," SPIE vol. 2432, 1995, pp. 280-290.
PCT. International Search Report and Written Opinion in PCT Application PCT/US07/241 03, May 5, 2008, 17 pages.
Pisani, L , et al., "Setup Error in Radiotherapy: On-line Correction using Electronic Kilovoltage and Megavoltage Radiographs", Int. J. Radiation Oncology Biol. Phys., vol. 47, No. 3, 2000, 825-839.
Ragan, et al., "Correction for Distortion in a Beam Outline Transfer Device in Radiotherapy CT-Based Simulation," Med. Phys. 20 (1), Jan./Feb. 1993, 179-185.
Redpath, et al., "The Use of a simulator and treatment planning computer as a CT scanner for radiotherapy planning," Abstract,

(56) References Cited

OTHER PUBLICATIONS

Proceedings—Eighth International Conference on the Use of Computers in Radiation Therapy held in Toronto, Canada, 1984, pp. 281-287. IEEE, New York, NY.
Reynolds, et al., "An algorithm for three-dimensional visualization of radiation therapy beams," Med Phys, 15 (1) Jan.-Feb. 1988, pp. 24-28.
Rizo et al., "Comparison of two three-dimensional x-ray cone-beam-reconstruction algorithms with circular source trajectories," J. Opt. Soc. Am. A, 10, 1639-1648, Oct. 1991.
Ruchala, K J., et al., "Megavoltage CT on Tomography System", Phy. Med. Biol. 44, 1999, 2597-2621.
Siewerdsen et al., "A ghost story: Spatio-temporal response characteristics of an indirect-detection flat-panel imager", Med. Phys. 26 (8), 1624-1641, Aug. 1999.
Siewerdsen, J.H, et al., "Cone-beam computed tomography with a flat-panel imager: Effects of image lag", Med. Phys. 26 (12), 2635-2647, Dec. 1999.
Siewerdsen, J H., et al., "Cone-Beam Computed Tomography with a Flat-Panel Imager: Magnitude and Effect of X-Ray Scatter", Med. Phys., 2.8 (2), Feb. 2001, 220-231.
Siewerdsen, J H., et al., "Optimization of X-Ray Imaging Geometry (With Specific Application to Flat-Panel Cone-Beam Computed Tomography)", Med. Phys., 27 (8), Aug. 2000, 1903-1914.
Supplementary European Search Report mailed Jan. 12, 2011 for European Application No. 03786979.9; 3 pages.
Swindell, W, et al., "Computed Tomography with a Linear Accelerator with Radiotherapy Applications", Med. Phys. 10 (4), Jul./Aug. 1983, 416-420.
Uematsu, M, et al., "A Dual Computed Tomography Linear Accelerator Unit for Stereotactic Radiation Therapy: A New Approach Without Cranially Fixated Stereotactic Frames", Int. J. Radiation Oncology Biol. Phys., vol. 35, No. 3, 1996, 587-592.
Uematsu, M, et al., "Daily Positioning Accuracy of Frameless Stereotactic Radiation Therapy with a Fusion of Computed Tomography and Linear Accelerator (focal) Unit: Evaluation of Z-axis with a Z-marker", Radiotherapy and Oncology 50, 1999, 337-339.
Uematsu, M, et al., "Infractional Tumor Position Stability During Computed Tomography (CT)-Guided Frameless Seterotactic Radiation Therapy for Lung or Liver cancers with a Fusion of CT and Linear Accelerator (FOCAL) Unit", Int. J. Radiation Oncology Biol. Phys, vol. 48, No. 2, 2000, 443-448.
Communication pursuant to Article 94(3) EPC for European Patent Application No. 03 786 979.9, dated Jan. 30, 2014, 8 pages.
Yan et al., "Derivation and analysis of a filtered backprojection algorithm for cone beam projection data," IEEE Trans. Medical Imaging, vol. 10, No. 3, 462-472, Sep. 1991.
Baiter, J M., et al., "Daily Targeting of intrahepatic tumors for Radiotherapy", Int. J. Radiation Oncology Biol. Phys., vol. 52, No. 1, 2002, 266-271.
Hara, "Radiotherapeutic System," 00480035/EP-B1, Citation from World Patent, Nov. 09, 1994, 1 page.
Kushima, GJ, et al., "New Development of Integrated CT Simulation System for Radiation Therapy Planning", Kobe J. Med. Sci., 39, Dec. 1993, 197-213.
Nakagawa, K, et al., "Megavoltage CT-Assisted Stereotactic Radiosurgery for Thoracic Tumors: Original Research in the Treatment of Thoracic Neoplasms", Int. J. radiation oncology biol. phys., col. 48, No. 2, 2000, 449-457.
Ning et al., "Flat Panel Detector-Based Cone-Beam vol. CT Imaging: Detector Evaluation," SPIE vol. 3659, 192-203, 1999.
Pisani, L, et al., "Setup Error in Radiotherapy: On-line Correction using Electronic Kilovoltage and Megavoltage Radiographs", Int. J. Radiation Oncology Biol. Phys., vol. 47, No. 3, 2000, 825-839.
Ruchala, K J., et al., "Megavoltage CT on Tomography System" Phy. Med. Biol. 44, 1999, 2597-2621.
Siewerdsen, J H., et al., "Cone-beam computed tomography with a flat-panel imager: Effects of image lag", Med. Phys. 26 (12), 2635-267, Dec. 1999.
Swindell, W, et al., "Computed Tomography with a Linear Accelerator with Radiotherapy Applications", Med. Phys. 10 (4), Jul./Aug. 1983, 416-420.
Uematsu, M, et al., "A Dual Computed Tomography Linear Accelerator Unit for Stereotactic Radiation Therapy: A New Approach Without Cranially Fixated Stereotactic Frames", Int. J. Radiation Oncology Biol. Phys., vol. 35, No. 3, 1996, 587-592.
Uematsu, M, et al., "Daily Positioning Accuracy of Frameless Stereotactic Radiation Therapy with a Fusion of Computed Tomography and Linear Accelerator (focal) Unit: Evaluation of Z-axis with a Z-marker", Radiotherapy and Oncology 50, 1999, 337-339
Uematsu, M, et al., "Infractional Tumor Position Stability During Computed Tomography (CT)-Guided Frameless Seterotactic Radiation Therapy for Lung or Liver cancers with a Fusion of CT and Linear Accelerator (FOCAL) Unit", Int. J. Radiation Oncology Biol. Phys, vol. 48, No. 2, 2000, 443-448
Advisory Action dated Dec. 10, 2015 for related U.S. Appl. No. 13/164,698.
Non-final Office Action dated Feb. 29, 2016 for related U.S. Appl. No. 13/164,698.

\* cited by examiner

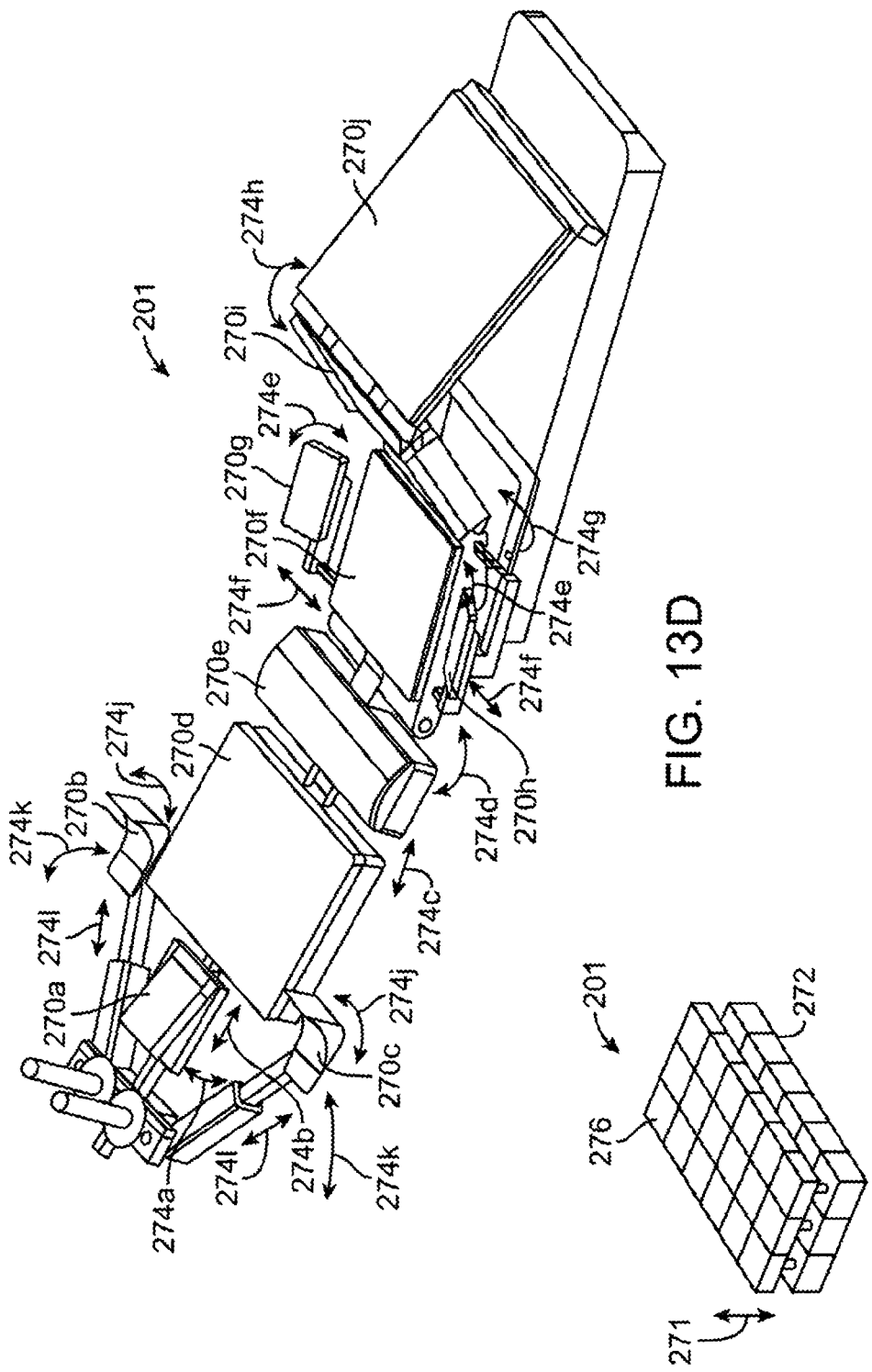

SYSTEM AND METHODS FOR TREATING PATIENTS USING RADIATION

RELATED APPLICATION DATA

This application is related to U.S. patent application Ser. No. 11/415,965, filed May 1, 2006, abandoned, U.S. patent application Ser. No. 11/415,866, filed May 1, 2006, now U.S. Pat. No. 7,983,380, and U.S. patent application Ser. No. 11/415,974, filed May 1, 2006, now U.S. Pat. No. 7,640,607.

FIELD

This application relates generally to radiation systems.

BACKGROUND

Various systems and methods exist to provide radiation therapy treatment of tumorous tissue with high-energy radiation. While some patient conditions require whole body radiation treatments, many forms of radiation treatment benefit from the ability to accurately control the amount, location and distribution of radiation within a patient's body. Such control often includes applying various levels of radiation to various areas of the tumorous region. For example, in some instances it is desirable to apply a greater dosage of radiation to one portion of a tumorous region than another. As another example, in some instances it is desirable to minimize the dosage of radiation to non tumorous regions where radiation may have deleterious effects. Due to a variety of contributing factors, achieving accurate control of the amount, location and distribution of radiation within the patient's body can be difficult. Among these factors are movement in the patient's body, changes in organ or inter organ structure or composition, and changes in the relative position of a patient's organs.

Prior to a radiation therapy, the patient undergoes an imaging procedure to determine the exact size, shape and location of the tumorous region. In a radiation treatment session, the patient is subjected to radiation from an accelerator that emits a beam of radiation energy collimated and oriented to enter the patient's body from a particular angle. Varying the intensity and the entry angle of the incident radiation beam allows a radiation specialist to generate a radiation dose volume that corresponds to the size, shape, and location of the tumorous region.

Several factors may prevent optimal radiation exposure to the tumorous region and minimal radiation exposure of the healthy tissue regions. For example, minor changes in patient's position from the imaging device to the treatment device may radically alter the position of the tumorous region or organ. In existing procedures, the patient is generally placed on a first patient support when the imaging device is used to obtain images of the patient. After the imaging session, the patient is then moved to a second patient support where the patient can be treated in a treatment session. As a result of moving the patient to different supports, the position and/or the shape of the target tissue within the patient may change.

Sometimes, a treatment radiation device and a diagnostic device may be placed in a same room to thereby reduce a transportation distance between the treatment and diagnostic devices. In such systems, the treatment radiation device may remain on while the diagnostic device is used to image the patient. If the treatment radiation device is placed too closely to the diagnostic device, a magnetic field (resulted from maintaining the accelerator of the treatment radiation device on) may interfere with an operation of the diagnostic device. Sometimes, the diagnostic device may remain on while the treatment device is used to treat the patient. In the case in which the diagnostic device includes a particle accelerator (e.g., an electron accelerator, as in an x-ray source), a magnetic field (resulted from maintaining the accelerator of the diagnostic device on) may also interfere with the operation of the treatment device.

Another problem associated with existing radiation system that includes a rotating radiation source is that a patient may feel uncomfortable while a radiation source is rotating around the patient. In the case in which the radiation source is secured to an arm that rotates around the patient, the patient may also be injured by a rotating arm if accidentally comes in contact with it. As such, it may be desirable to protect the patient from a rotating component of a radiation system while the patient is undergoing through treatment and/or imaging.

A further problem associated with existing radiation systems is that they are bulky and occupy much space. This is attributable at least in part by the fact that existing radiation systems use an electromagnetic system to change a trajectory of a beam. Such electromagnetic system generally takes up a lot of space and is expensive to make. As such, it would be desirable to provide a radiation system that is space efficient and/or less expensive to manufacture.

SUMMARY

In accordance with some embodiments, a radiation system includes a radiation source having an accelerator, the radiation source having a magnetic field associated therewith that is resulted from an operation of the accelerator, and a magnetic field source configured to provide a compensating magnetic field to at least partially counteract against the magnetic field that is resulted from the operation of the accelerator.

In accordance with other embodiments, a radiation system includes a radiation device having a radiation source, a patient support, and a protective guard located between the radiation source and the patient support, wherein the protective guard is moveably coupled to the radiation device or the patient support.

In accordance with other embodiments, a radiation system includes a particle generator for generating a particle, an accelerator for accelerating the particle, and a magnetic source for changing a trajectory of the particle, wherein the magnetic source comprises a permanent magnet.

In accordance with other embodiments, a radiation system includes a structure having a first side, a second side, a first opening located on the first side, a second opening located on the second side, and a bore that extends between the first and the second openings, a radiation source coupled to the structure, and a patient position sensing device located next to the radiation source.

In accordance with other embodiments, a radiation method includes using a device to obtain physiological data of a patient, delivering treatment radiation to treat a portion of the patient, wherein the delivery of the treatment radiation is performed based at least in part on the physiological data, and moving the portion of the patient from a first side of a structure to a second side of the structure through a bore on the structure.

Other aspects and features will be evident from reading the following detailed description of the embodiments.

BRIEF DESCRIPTION OF THE DRAWINGS

The drawings illustrate the design and utility of preferred embodiments, in which similar elements are referred to by common reference numerals. In order to better appreciate how advantages and objects of the embodiments are obtained, a more particular description of the embodiments will be illustrated in the accompanying drawings.

FIG. 13D illustrates an isometric view of a patient support in accordance with other embodiments;

FIG. 13E illustrates an isometric view of a patient support in accordance with other embodiments;

DETAILED DESCRIPTION OF THE EMBODIMENTS

Figure 1A:
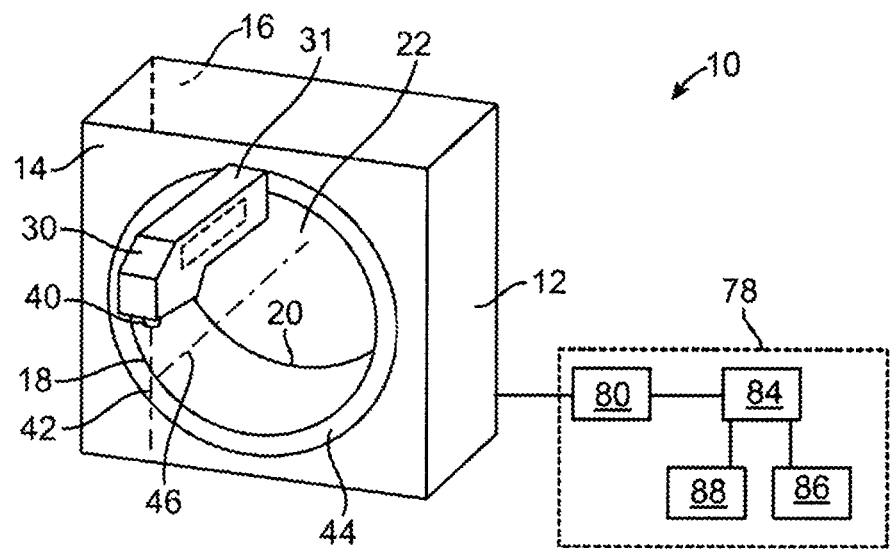
FIG. 1A illustrates an isometric view of a radiation system in accordance with some embodiments.

Various embodiments are described hereinafter with reference to the figures. It should be noted that the figures are not drawn to scale and elements of similar structures or functions are represented by like reference numerals throughout the figures. It should also be noted that the figures are only intended to facilitate the description of specific embodiments. They are not intended as an exhaustive description of the invention or as a limitation on the scope of the invention. In addition, an aspect described in conjunction with a particular embodiment is not necessarily limited to that embodiment and can be practiced in any other embodiments. Moreover, alternative configurations, components, methods, etc. discussed in conjunction with one embodiment can be used in any other embodiment even if such other embodiment does not discuss such alternatives or discusses different alternatives.

FIG. 1A illustrates a radiation system 10 in accordance with some embodiments. The radiation system 10 includes a structure 12 having a first side 14, a second side 16, a first opening 18 located on the first side 14, a second opening 20 located on the second side 16; and a bore 22 extending between the first and second openings 18, 20. In the illustrated embodiments, the openings 18, 20 are circular in shape and are sized for accommodating at least a part of a patient. In other embodiments, the openings 18, 20 can have other shapes. The through bore 22 of the structure 12 provides a passage for allowing at least a portion of a patient to be transported from one side of the structure 12 to an opposite side of the structure 12. In some embodiments, a diagnostic procedure (e.g., an imaging procedure) is performed on the patient on one side of the structure 12 (e.g., for the purpose of obtaining information, such as a position of a target region, of the patient), and the patient is then transported through the bore 22 to the opposite side of the structure 12 for a treatment procedure. In other embodiments, the patient is treated on one side of the structure 12, and is then transported through the bore 22 to the opposite side of the structure 12 for further procedure(s), such as a diagnostic procedure (e.g., to evaluate a treatment procedure, or to verify location, orientation, and/or shape of a target tissue,) or a treatment procedure.

It should be noted that the shape and configuration of the structure 12 should not be limited to the examples discussed previously, and that the structure 12 can have other configurations in other embodiments. For example, in other embodiments, the structure 12 can have a curvilinear shape, or other shapes. Also, in some embodiments, the structure 12 can have a size and shape such that the structure can house mechanical and electrical components associated with an operation of the radiation system 10 as desired.

The radiation system 10 also includes a first radiation source 40 located adjacent to the first side 14 for delivering a radiation beam 42. The radiation beam 42 can be a pencil beam, a fan beam, a cone beam, or other types of beams having different configurations. As used in this specification, the term "radiation source" refers to an emission point/region of a radiation beam (e.g., radiation beam 42), and may or may not include components, such as a particle generator, an accelerator, a cooling system, a shielding, etc., that are used to generate the radiation beam 42. As shown in the figure, the radiation system 10 includes an arm 30 secured to the structure 12, and the first radiation source 40 is secured to the arm 30. Some or all of the components used to generate the radiation beam 42 can be housed within the arm 30, the structure 12, a separate housing (not shown), or combination thereof. For example, in some embodiments, the accelerator 31 associated with the radiation source 40 may be housed within the arm 30. In such cases, one or more magnets (electromagnet(s) or permanent magnet(s)) may be provided within the arm 30 for changing a characteristic (e.g., a trajectory) of an electron beam created by the accelerator 31. If permanent magnet(s) is used, its associated magnetic field can be trimmed electromagnetically (e.g., using one or more electromagnetic coil(s)) or mechanically (e.g., using one or more permanent magnet(s)). Also, in some embodiments, the mechanical trimming can be performed using a magnetic shunt. Magnetic field trimming will be described with reference to FIG. 18.

As shown in the figure, the arm 30 is secured to a mechanical linkage 44, such as a ring, that is rotatable relative to the structure 12, thereby allowing the first radiation source 40 to rotate about an axis 46 of the bore 22. The arm 30 of the radiation system 10 is advantageous in that it allows radiation be delivered to a portion of a patient that is placed outside the bore 22. In particular, since the patient is not confined by the bore 22, the patient can be oriented at different angles relative to the axis 46 outside the bore 22. For example, the patient can be positioned at least partially outside the bore 22 and oriented at an angle relative to the axis 46. In some embodiments, the arm 30 is also advantageous in that it can be used to house at least some of the components, such as an accelerator, associated with the radiation source 40, thereby eliminating the need to cramp the components within the bore 22.

Figure 1B:
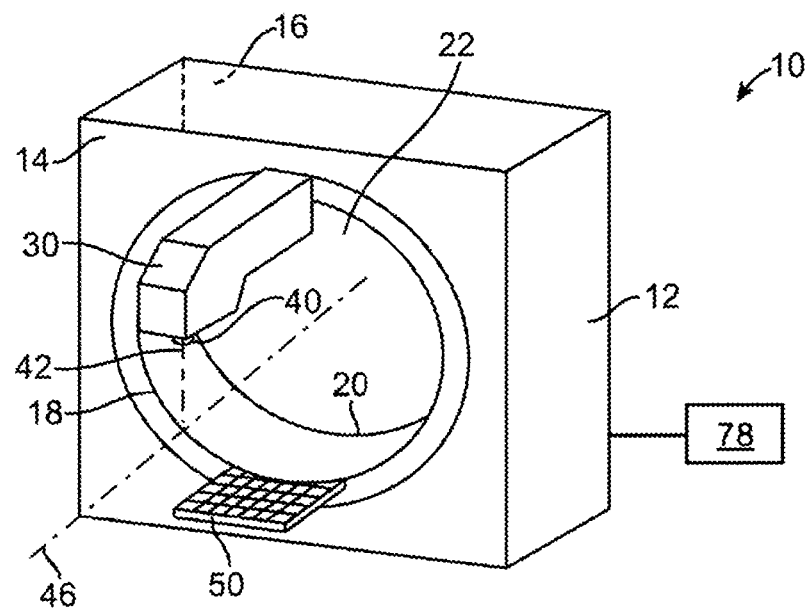
FIG. 1B illustrates an isometric view of a radiation system having imaging capability in accordance with some embodiments.
Figure 1C:
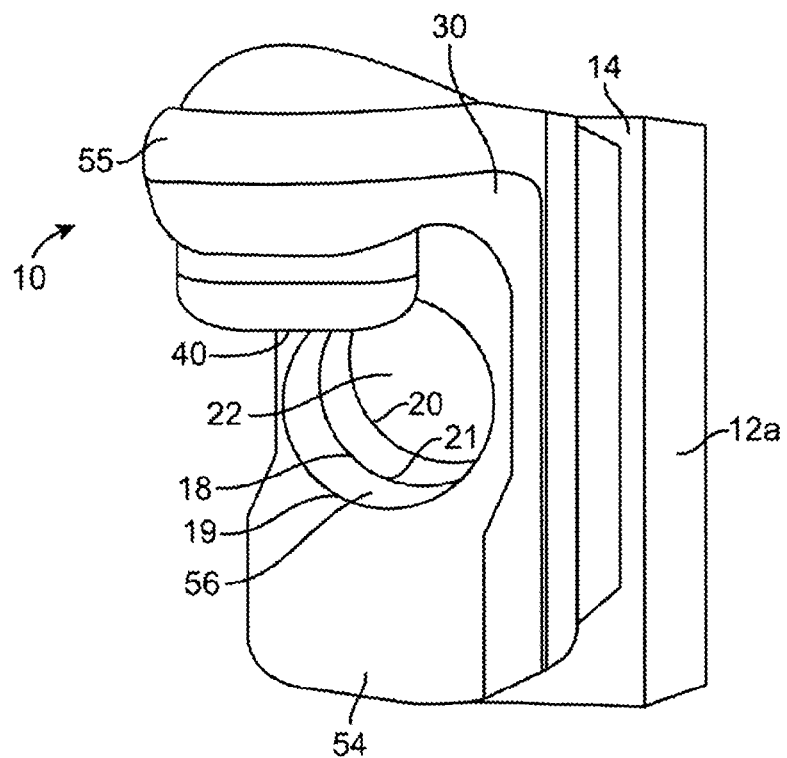
FIG. 1C illustrates an isometric view of a radiation system in accordance with other embodiments.
Figure 1D:
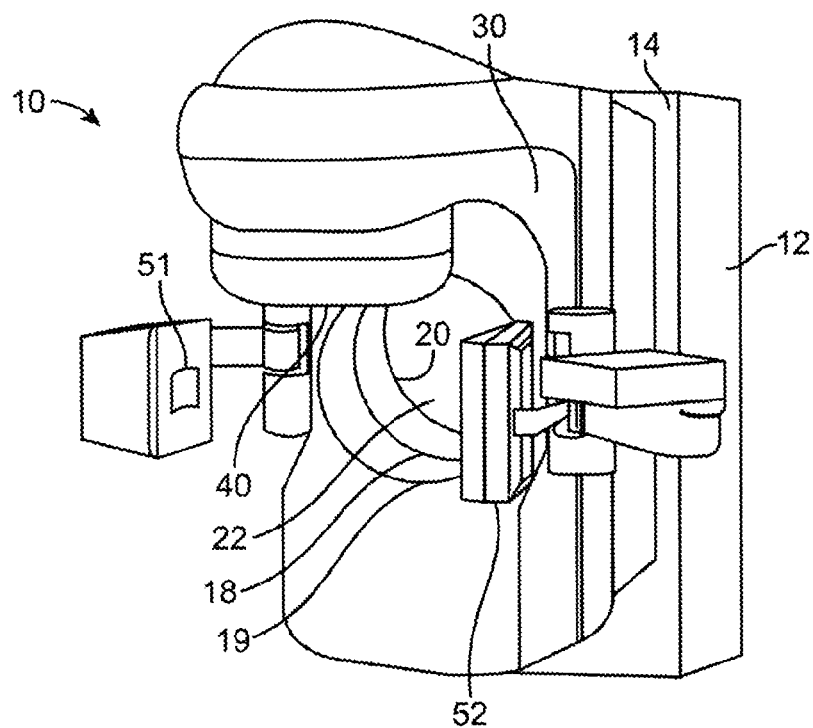
FIG. 1D illustrates an isometric view of a radiation system in accordance with other embodiments.
Figure 1E:
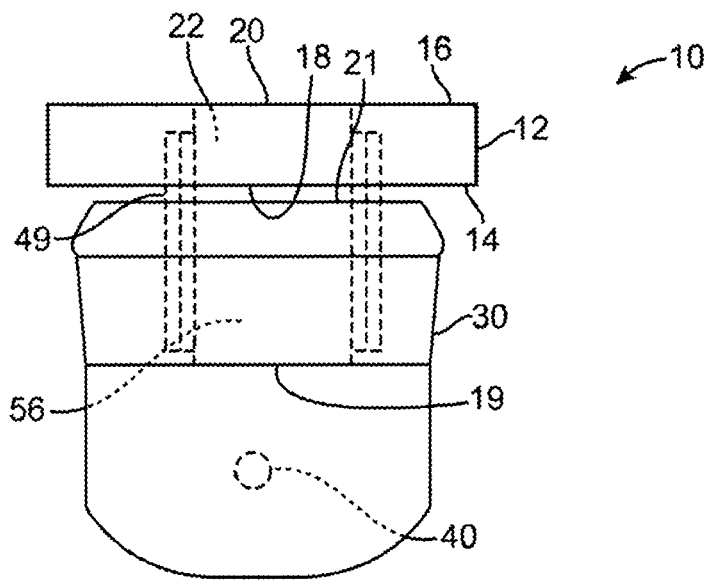
FIG. 1E illustrates a top view of the radiation system of FIG. 1C in accordance with some embodiments.
Figure 1F:
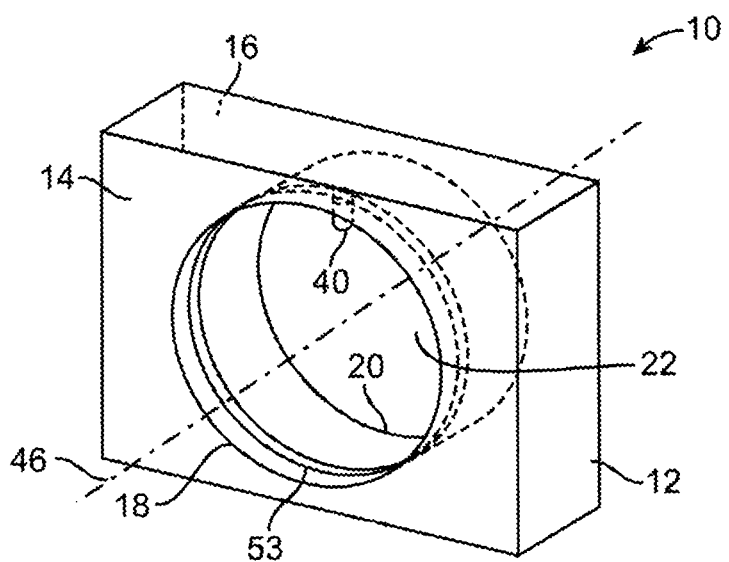
FIG. 1F illustrates an isometric view of a radiation system in accordance with other embodiments.

In other embodiments, or any of the embodiments described herein, the radiation system 10 may not include the arm 30 (FIG. 1F). In such cases, the first radiation source 40 may be rotatably secured to the structure 12. For example, the radiation source 40 may be secured to a ring (which may be a full ring or a partial ring) that is rotatable relative to the structure 12 in a slip-ring configuration. In such cases, at least some of the components within arm 30 may be disposed within the structure 12. It should be noted that any one or a combination of any of the features described herein may be incorporated and implemented with the radiation system 10 of FIG. 1F, and that a configuration where a radiation source such as source 40 is within a ring can be incorporated and implemented in any embodiments such as those illustrated or described herein.

In the illustrated embodiments, the first radiation source 40 is a treatment radiation source for providing treatment energy. In such cases, the radiation system 10 further includes one or more collimators (not shown) for controlling a delivery of the radiation beam 42 (e.g., changing a shape of the beam 42). A collimator can be, for example, a multi-leaf collimator, which is known in the art. Alternatively, the first radiation source 40 can be a diagnostic radiation source for providing diagnostic energy. In some embodiments, the treatment energy is generally those energies of 160 keV or greater, and more typically 1 MeV or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. For example, a radiation beam having an energy level that is typically used for treatment purpose may be considered as having a diagnostic energy level if the radiation beam is used for diagnostic purpose (e.g., for imaging). As such, the term "treatment energy" and the term "diagnostic energy" should not be limited to energy levels having certain magnitudes. In further embodiments, the first radiation source 40 is a multi-energy x-ray source that is capable of providing radiation energy at different energy levels. By way of example, the first radiation source 40 is able to generate X-ray radiation at a plurality of photon energy levels within a range anywhere between approximately 10 kilo-electron-volts (keV) and approximately 20 mega-electron-volts (MeV). Radiation sources capable of generating X-ray radiation at different energy levels are described in U.S. patent application Ser. No. 10/033,327, entitled "RADIOTHERAPY APPARATUS EQUIPPED WITH AN ARTICULABLE GANTRY FOR POSITIONING AN IMAGING UNIT," filed on Nov. 2, 2001, and U.S. patent application Ser. No. 10/687,573, entitled "MULTI-ENERGY X-RAY SOURCE," filed on Oct. 15, 2003, both of which are expressly incorporated by reference in their entirety.

In some embodiments, the radiation system 10 further includes a control system 78. The control system 78 includes a processor 84, such as a computer processor, coupled to a control 80. The control system 78 may also include a monitor 86 for displaying data and an input device 88, such as a keyboard or a mouse, for inputting data. In some embodiments, during an operation of the radiation system 10, the radiation source 40 rotates about the patient (e.g., as in an arc-therapy). The rotation and the operation of the radiation source 40 are controlled by the control 80, which provides power and timing signals to the radiation source 40 and controls a rotational speed and position of the radiation source 40 based on signals received from the processor 84. Although the control 80 is shown as a separate component from the structure 12 and the processor 84, in alternative embodiments, the control 80 can be a part of the structure 12 or the processor 84.

In any of the embodiments described herein, the radiation system 10 can further include an imager 50 located next to the first opening 18 and opposite from the radiation source 40 (FIG. 1B). In some embodiments, the imager 50 includes a conversion layer made from a scintillator element, such as Cesium Iodide (CsI), and a photo detector array (e.g., a photodiode layer) coupled to the conversion layer. The conversion layer generates light photons in response to radiation, and the photo detector array, which includes a plurality of detector elements, is configured to generate electrical signal in response to the light photons from the conversion layer. The imager 50 can have a curvilinear surface (e.g., a partial circular arc). Such configuration is beneficial in that each of the imaging elements of the imager 50 is located substantially the same distance from the radiation source 40. In an alternative embodiment, the imager 50 may have a rectilinear surface or a surface having other profiles. The imager 50 can be made from amorphous silicon, crystal and silicon wafers, crystal and silicon substrate, or flexible substrate (e.g., plastic), and may be constructed using flat panel technologies or other techniques known in the art of making imaging device. In alternative embodiments, the imager 50 may use different detection schemes. For example, in alternative embodiments, instead of having the conversion layer, the imager 50 may include a photoconductor, which generates electron-hole-pairs or charges in response to radiation.

It should be noted that the configuration of the imager 50 should not be limited to the examples discussed previously, and that imagers having other configurations may be used in other embodiments. By way of example, U.S. patent application Ser. No. 10/439,350, entitled "MULTI ENERGY X-RAY IMAGER" filed on May 15, 2003, discloses imaging devices capable of generating signals in response to multiple radiation energy levels, and can be used as the imager 50 in accordance with some embodiments. In addition, U.S. patent application Ser. No. 10/013,199, entitled "X-RAY IMAGE ACQUISITION APPARATUS," and filed on Nov. 2, 2001, discloses an image detecting device that is capable of detecting multiple energy level X-ray images, and can also be used as the imager 50 in accordance with other embodiments. U.S. patent application Ser. No. 10/687,552, entitled "MULTI-ENERGY RADIATION DETECTOR," and filed on Oct. 15, 2003, discloses multi-energy radiation detectors that can be used as the imager 50 in different embodiments. In other embodiments, the imager 50 can be implemented using flat panel technologies. Also, in further embodiments, the imager 50 can be a multi-slice flat panel. Multi-slice flat panel CT has been described in U.S. patent application Ser. No. 10/687,552, entitled "MULTI-SLICE FLAT PANEL COMPUTED TOMOGRAPHY," and filed on Oct. 15, 2003. U.S. patent application Ser. Nos. 10/439,350, 10/013,199, and 10/687,550 are expressly incorporated by reference in their entirety. In other embodiments, the imager 50 may be similarly incorporated in the radiation system 10 of FIG. 1F, or in any of the radiation systems 10 described herein.

It should be noted that the radiation system 10 should not be limited to the configuration discussed previously, and that the radiation system 10 can have other configurations in other embodiments. For example, in some embodiments, the radiation system 10 can have the configuration shown in FIG. 1C. In the illustrated embodiments, the radiation system 10 includes the structure 12a, which has a configuration that is similar to that discussed previously with reference to structure 12 of FIG. 1A. The radiation system 10 also includes the arm 30 and the radiation source 40. However, in the illustrated embodiments, the arm 30 has a configuration that resembles a L-shape, and includes a first portion 54 and a second portion 55. The second portion 55 of the arm 30 has a first opening 19, a second opening 21, and a bore 56 extending between the first and the second openings 19, 21. As shown in FIG. 1E, which is a top view of the system of FIG. 1C, the arm 30 is rotatably coupled to the structure 12 via a cylindrical shaft 49, which circumscribe at least part of the bore 22 and at least part of the bore 56 in a coaxial configuration. In other embodiments, the arm 30 can be rotatably coupled to the structure 12 in other configurations. The bore 56 is positioned relative to the bore 22 such that at least a part of a patient can move through the bore 56 to the bore 22, and vice versa. In other embodiments, any of the features described herein can also be included with the radiation system 10 of FIG. 1C. For example, in other embodiments, the radiation source 40 can deliver diagnostic energy, and the radiation system 10 of FIG. 1C can further include an imager (e.g., the imager 50) in operative position with the radiation source 40 such that the radiation source 40 and the imager can be used to generate image data.

In some embodiments, any of the radiation systems 10 described herein can further include a x-ray source, such as tube 51 (an example of an imaging device) and an imager 52 (another example of an imaging device) secured to the second portion 54 of the arm 30 (FIG. 1D), wherein the x-ray tube 51 and the imager 52 are positioned to image at least a portion of the patient. The x-ray tube 51 and the imager 52 can be used to generate data regarding a patient while the patient is positioned in an operative position associated with the radiation source 40. For example, in some embodiments, the x-ray tube 51 generates a cone beam, and the imager 52 generates cone beam CT data, which represent image of a portion of a patient. Alternatively, the imaging devices can be used for radiography or fluoroscopic imaging. In the embodiments of FIG. 1A, the x-ray tube 51 and the imager 52 could be attached to ring 44. In the embodiments of FIG. 1F, the x-ray tube 51 and the imager 52 could be attached to the ring 53.

Figure 2:
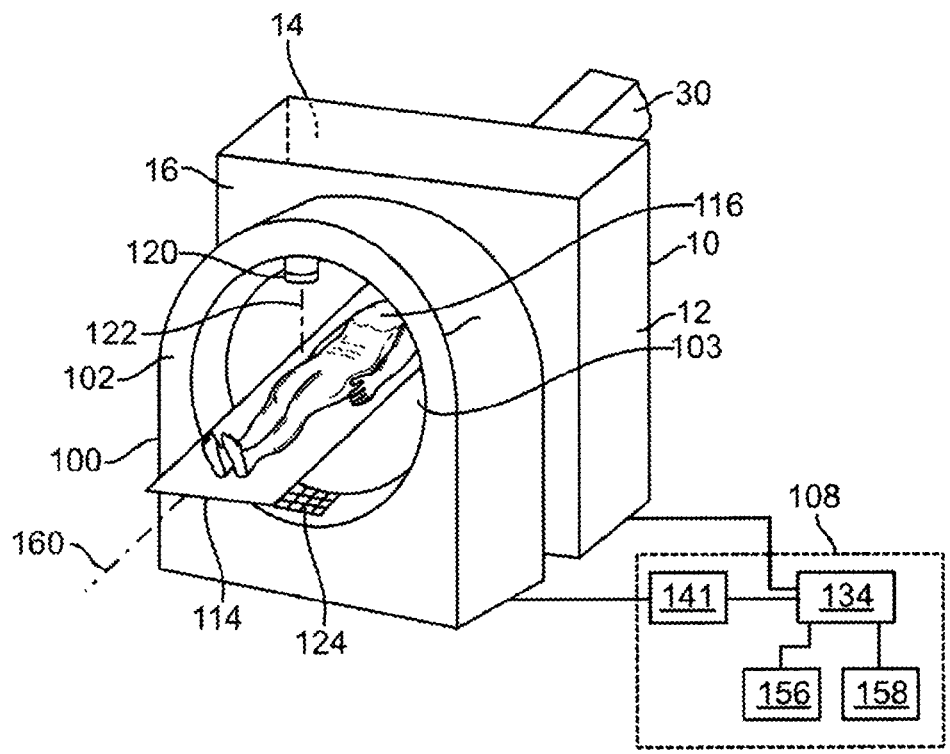
FIG. 2 illustrates an isometric view of a radiation system that includes, or is used with, a computed tomography device, in accordance with some embodiments.

FIG. 2 illustrates the radiation system 10 of FIG. 1A when used with a computed tomography image acquisition device (CT device) 100. The CT device 100 includes a gantry 102 having a bore 103, a patient support 114 for supporting a patient 116, and a control system 108 for controlling an operation of the gantry 102. In the illustrated embodiments, the gantry 102 has a slip-ring configuration (donut shape). Alternatively, the gantry 102 can have other configurations, such as a C-arm configuration. The CT device 100 also includes a radiation source (e.g., x-ray source) 120 that projects a beam 122 of radiation towards a detector 124 on an opposite side of the gantry 102 while the patient 116 is positioned at least partially between the radiation source 120 and the detector 124. The radiation source 120 can be configured to generate a cone beam (for cone beam computed tomography—"CBCT"). In other embodiments, the radiation source 120 generates beams having other configurations, such as a fan beam. The detector 124 has a plurality of sensor elements configured for sensing radiation that passes through the patient. Each sensor element generates an electrical signal representative of an intensity of the radiation as it passes through the patient. It will be appreciated that throughout the present specification, although specific embodiments of various imaging devices may be illustrated by fan beam CT or cone beam CT, any type of CT generally can be practiced in any of the embodiments.

The control system 108 includes a processor 134, such as a computer processor, coupled to a gantry rotation control 141. The control system 108 may also include a monitor 156 for displaying data and an input device 158, such as a keyboard or a mouse, for inputting data. During a scan to acquire x-ray projection data (i.e., CT image data), the gantry 102 rotates about the patient. The rotation of the gantry 102 and the operation of the radiation source 120 are controlled by the gantry rotation control 141, which provides power and timing signals to the radiation source 120 and controls a rotational speed and position of the gantry 102 based on signals received from the processor 134. Although the control 141 is shown as a separate component from the gantry 102 and the processor 134, in alternative embodiments, the control 141 can be a part of the gantry 102 or the processor 134. In some embodiments, the processor 134 and the processor 84 are implemented using a same component, such as a single processor.

During a radiation procedure using the CT device 100, the radiation source 120 generates and directs a x-ray beam 122 towards the patient 116, while the detector 124 measures the x-ray absorption at a plurality of transmission paths defined by the x-ray beam during the process. The detector 124 produces a voltage proportional to the intensity of incident x-rays, and the voltage is read and digitized for subsequent processing in a computer. After image data at different gantry angles have been collected, the collected data are processed for reconstruction of a matrix (CT image), which constitutes a depiction of a density function of the bodily section being examined. By considering one or more of such sections, a skilled diagnostician can often diagnose various bodily ailments. In some cases, the one or more sections can also be used to perform treatment planning.

As shown in the figure, an axis 160 of the bore 103 of the CT device 100 is substantially parallel with (e.g., within 20° from) the axis 46 of the bore 22 of the radiation system 10. Such configuration allows the patient 116 to be transported between a first operative position (e.g., the position of the patient 116 when being operated (e.g., treated or imaged) by the radiation source 40 of the radiation system 10) and a second operative position (e.g., the position of the patient 116 when being operated by the radiation source 120 of the CT device 100). In the illustrated embodiments, the patient 116 can be transported between the first and second operative positions by positioning the patient support 114 in a linear manner along the axis 46 of the radiation system 10. Patient supports that can be used with the radiation system 10 will be described in further detail later. In the illustrated embodiments, the axis 160 of the bore 103 aligns with the axis 46 of the bore 22. In other embodiments, the axis 160 of the bore 103 may not align with the axis 46 of the bore 22. For example, in some embodiments, the axis of the bore 160 may be offset from the axis 46 of the bore 22.

In the illustrated embodiments of FIG. 2, the processor 134 used to control an operation of the CT device 100 is also coupled to the radiation system 10, and is configured to control an operation of the radiation system 10. Alternatively, a separate control system (e.g., the system 78) can be used to control an operation of the radiation system 10. Also, in some embodiments, the radiation system 10 includes the CT device 100. In such cases, the CT device 100 can be separated from the radiation system 10 as that shown in the figure. Alternatively, the CT device 100 can be integrated with the radiation system 10 as a single unit.

In some embodiments, the electron accelerator 31 associated with the radiation source 40 may cause interference with the device 100. In such cases, a shield (not shown) can be placed between the accelerator 31 and the device 100 to prevent, or at least minimize the effect of, interference due to the accelerator 31. The shield can be made from Mumetal or other materials. In some embodiments, the shield can be placed around the accelerator 31. In other embodiments, the shield can be placed around the device 100 or a component (e.g., a component that may be affected by a magnetic field from the accelerator 31) of the device 100. In other embodiments, the shield can be secured to the structure 12, such as to the second side 16 of the structure 12.

Figure 3:
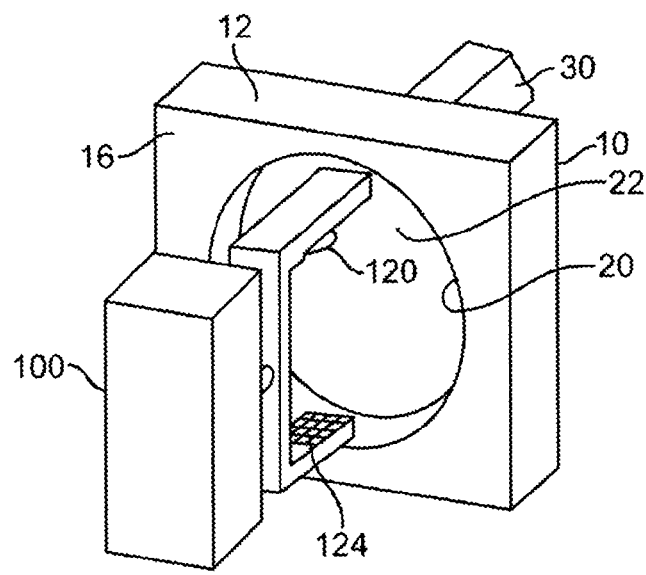
FIG. 3 illustrates an isometric view of a radiation system that includes, or is used with, a device having a C-arm configuration, in accordance with some embodiments.

It should be noted that the devices that can be used/included with the radiation system 10 should not be limited to the CT device 100 discussed previously, and that a variety of forms of medical devices (e.g., devices with a ring gantry) can be used/included with the radiation system 10 in other embodiments. For example, in some embodiments, the device 100 used/included with the radiation system 10 may be a diagnostic/treatment device having a C-arm configuration (FIG. 3). The device 100 is positioned relative to the bore 22 such that a patient can be positioned between a first operative position associated with the radiation source 40, and a second operative position associated with the device 100. In any embodiment, the device 100 can be any diagnostic device, such as a laminar tomography device, a MRI device, a fluoroscope, an angiography device, a PET device, a SPECT device, a PET-CT device, a tomosynthesis imaging device, a CT device, a CBCT device, etc. that can be used/included with the radiation system 10. In such cases, the diagnostic device 100 is positioned relative to the bore 22 such that a patient can be positioned between a first operative position associated with the radiation source 40, and a second operative position associated with the diagnostic device. In further embodiments, the device 100 used/included with the radiation system 10 may include a plurality of diagnostic devices (e.g., any multiple, or any combination, of the diagnostic devices described).

In the above embodiments, the radiation system 10 can further include rollers that allows the radiation system 10 to be "rolled" to a desired position. After the radiation system 10 is desirably positioned, the rollers may be locked to thereby prevent the radiation system 10 from moving. For example, the rollers may be locked during an operation. The rollers are advantageous because it allows the flexibility to readily move the radiation system 10 (e.g., before an operation, or during an operation). In other embodiments, the rollers are optional, and the radiation system 10 is fixedly secured to a floor of an operation room.

Figure 4A:
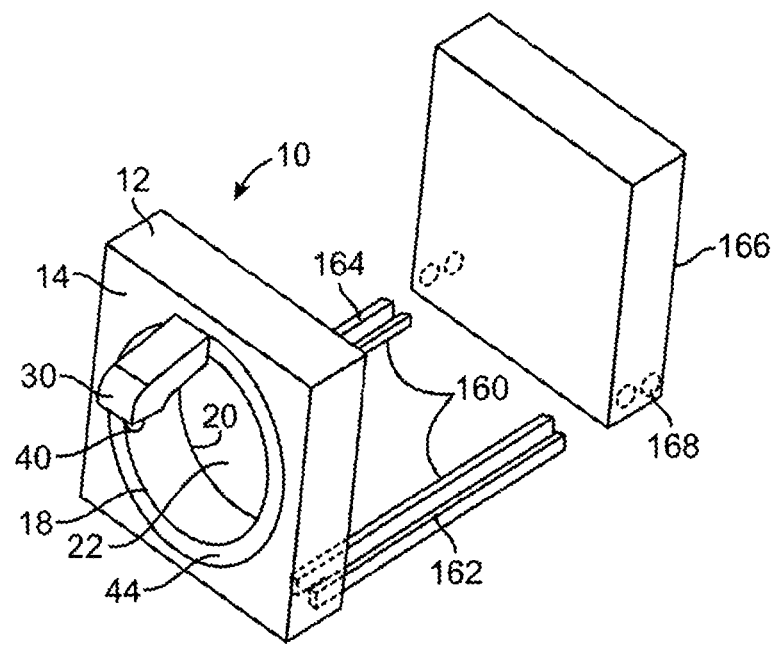
FIG. 4A illustrates an isometric view of a radiation system having a docking system for allowing a device to be docked adjacent to the radiation system in accordance with some embodiments.

In some embodiments, the radiation system 10 can further include a docking system that allows a device 100 to be docked next to the second opening 20 in a desired relationship (either during an operation, or before an operation). Various techniques can be employed to implement the docking feature of the radiation system 10. FIG. 4A illustrates the radiation system 10 of FIG. 1A that includes a docking system 160 for allowing a device 166 to be docked next to the structure 12. The device 166 is represented as a block diagram, and can be a treatment device or a diagnostic device (such as any of the devices 100 discussed previously). In the illustrated embodiments, the docking system 160 is a rail system that includes a first rail 162 and a second rail 164 located adjacent to the second side 16 of the radiation system 10. The rails 162, 164 can be secured to the radiation system 10, a floor at which the radiation system 10 sits, or a platform (not shown) that is itself secured to the radiation system 10 or the floor. The rails 162, 164 each have a substantially rectilinear profile, but can have a curvilinear profile in other embodiments. Also, in other embodiments, the docking system 160 can have less than two (e.g., one) rails, or more than two rails.

Figure 4B:
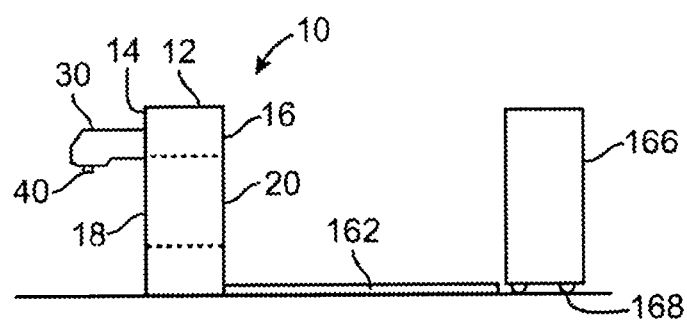
FIGS. 4B and 4C illustrate a method of docking a device adjacent to the radiation system of FIG. 4A in accordance with some embodiments.
Figure 4C:
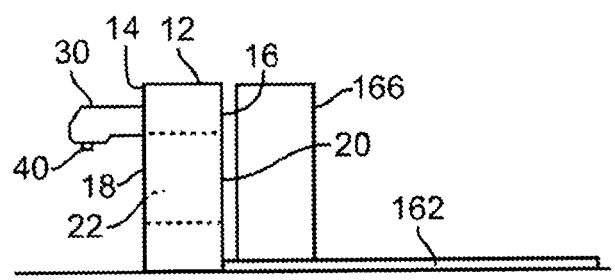

FIGS. 4B and 4C illustrate a method of docking a device 166 adjacent to the second side 16 of the radiation system 10 in accordance with some embodiments. The device 166 is represented as a block diagram, and can be a treatment device or a diagnostic device (such as any of the devices 100 discussed previously). As shown in FIG. 4B, before the device 166 is docked, the device 166 is positioned such that its wheels/rollers 168 are aligned with the rails 162, 164 of the docking system 160. The device 166 is then advanced such that the rollers 168 engage with the docking system 160. Next, the device 166 is further advanced, while guided by the docking system 160, until the device 166 is docked next to the second opening 20 of the radiation system 10 (FIG. 4C). In some embodiments, the docking system 160 can further include a locking device (not shown), which can be used to lock the device 166 in place when the device 166 is desirably positioned.

In some embodiments, the position of one or both of the rails 162, 164 of the docking system 160 can be adjusted such that the docking system 160 can accommodate different devices 166 having different configurations. For example, in some embodiments, the distance between the rails 162, 164 can be varied such that devices 166 having different roller spacing can be docked. Also, in other embodiments, one or more rails can be removed or added to the docking system 160 for allowing devices 166 having different number of rollers to be docked. In some embodiments, the docking system 160 can further include the rollers 168 of the device 166.

It should be noted that the docking system 160 should not be limited to the example discussed previously, and that the docking system 160 can be implemented using other techniques. For example, in other embodiments, instead of, or in addition to rail(s), the structure 12 and the device 166 can have a key-type docking mechanism, which allows a portion of the structure 12 to mate with a portion of the device 166, or other alignment devices, including visual alignment marks, sensors, or other means, which allow the device 166 to be positioned in a desired relationship relative to the radiation system 10. In further embodiments, the device 166 does not include rollers 168. Instead, the device 166 can be positioned using a crane, air cushion, a positioner, glide block(s), or other transportation mechanism.

In some embodiments, instead of, or in addition to, the docking system 160, the radiation system 10 can further include a docking system 170 for allowing the structure 12 to be docked into a desired position. Various techniques can be employed to implement the docking feature of the radiation system 10.

Figure 5A:
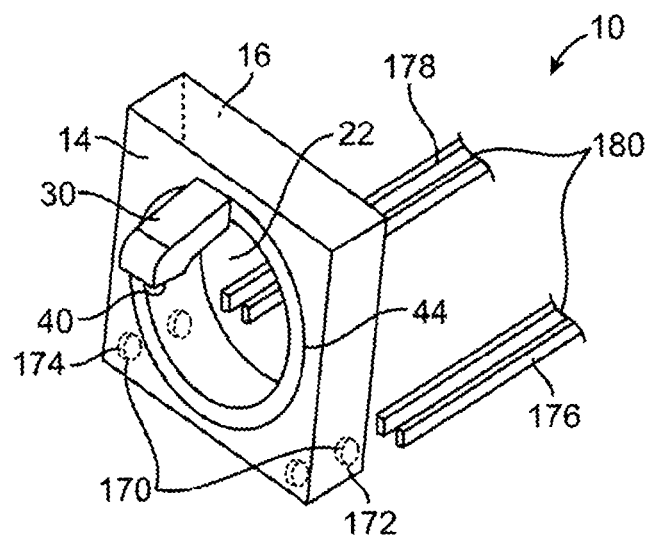
FIG. 5A illustrates an isometric view of a radiation system having a docking system for allowing the radiation system to be docked adjacent to a device in accordance with some embodiments.

FIG. 5A illustrates the radiation system 10 of FIG. 1A that includes a docking system 170. In the illustrated embodiments, the docking system 170 includes a roller system having a set of first roller(s) 172 and a second set of roller(s) 174 located adjacent to a bottom portion of the radiation system 10. In other embodiments, the docking system 170 can have less than two (e.g., one) roller, or more than sets of two rollers. In the illustrated embodiments, the roller sets 172, 174 are configured to mate with rails 176, 178 of a rail system 180. The rail system 180 can be secured to another device, such as the device 166, a floor at which the radiation system 10 sits, or a platform that is placed against a floor or secured to the device 166. The rails 176, 178 each have a substantially rectilinear profile, but can have a curvilinear profile in other embodiments. In some embodiments, the docking system 170 can further includes the rail system 180.

Figure 5B:
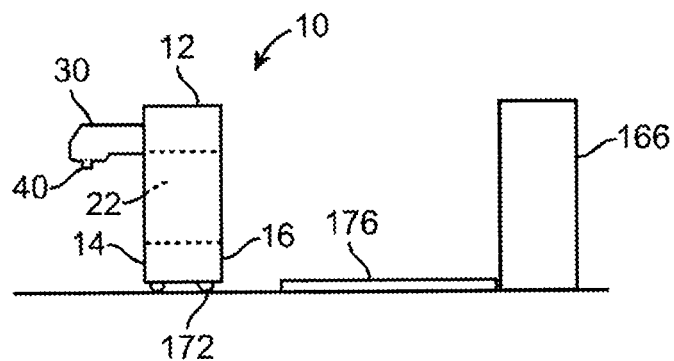
FIGS. 5B and 5C illustrate a method of docking the radiation system of FIG. 5A adjacent to a device in accordance with some embodiments.
Figure 5C:
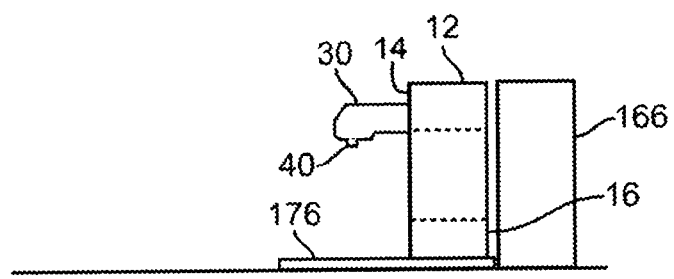

FIGS. 5B and 5C illustrate a method of docking the radiation system 10 to a desired position, e.g., adjacent to the device 166, in accordance with some embodiments. The device 166 is represented as a block diagram, and can be a treatment device or a diagnostic device (such as any of those discussed previously). As shown in FIG. 5B, before the radiation system 10 is docked, the radiation system 10 is positioned such that its roller sets 172, 174 are aligned with the rails 176, 178. The radiation system 10 is then advanced such that the roller sets 172, 174 engage with the rails 176, 178, respectively. Next, the radiation system 10 is further advanced, while guided by the rails 176, 178, until the radiation system 10 is docked next to the device 166 (FIG. 5C). In some embodiments, the docking system 170 can further include a locking device (not shown), such as a brake system, which can be used to lock the radiation system 10 in place when the radiation system 10 is desirably positioned.

In some embodiments, the position of one or both of the roller sets 172, 174 of the docking system 170 can be adjusted such that the radiation system 10 can be mated with rails having different configurations. For example, in some embodiments, the distance between the roller sets 172, 174 can be varied such that the radiation system 10 can be docked with rails having different spacing. Also, in other embodiments, one or more roller sets can be removed or added to the docking system 170 for allowing the radiation system 10 to dock with a rail system having different number of rails.

It should be noted that the docking system 170 should not be limited to the example discussed previously, and that the docking system 170 can be implemented using other techniques. For example, in other embodiments, the structure 12 and the device 166 can have a key-type docking mechanism, which allows a portion of the structure 12 to mate with a portion of the device 166. In alternative embodiments, the docking system 170 can have a first portion (e.g., a, protrusion) associated with the radiation system 10, and a second portion (e.g., a component having a recess) associated with the device 166, wherein the first portion and/or the second portion are configured to mate with each other. The first and second portions of a docking system can be implemented using any machinery, device, or system known in the art, including those described earlier in relation to FIGS. 4A-4C. In other embodiments, the radiation system 10 can include other alignment devices, which allow the radiation system 10 to be positioned in a desired relationship relative to the device 166. In further embodiments, the radiation system 10 does not include the roller system. Instead, the radiation system 10 can be positioned using a crane, air cushion, a positioner, glide block(s), or other transportation mechanism.

In any of the docking systems described herein, the docking system can further include one or more facilities, such as a water line, an electricity connection, an oil supply, etc., that connects to the device (such as the structure 12 or the device 166) as the device is being docked (or after the device is docked). In some embodiments, the facilities can be located on, underneath a floor, or underneath a platform that is secured to the floor. Alternatively, or additionally, the docking system can allow for provision of facilities from one device, such as device 12, to one or more others.

Also, in any of the docking systems described herein, the docking system can further include a communication system that allows one device to communicate with the device 166 or another device. For example, in some embodiments in which the device 166 is being docked, the structure 12 includes a signal receiver and/or a transmitter, and the device 166 includes a signal transmitter and/or a receiver. During use, the signal transmitter of, e.g., the device 166 transmits signals to the structure 12 regarding a position of the device 166 (e.g., relative to a prescribed coordinate system). The signal receiver of the structure 12 receives the transmitted signal, and generates an output based on the transmitted signal. In some embodiments, the output can be displayed on a user interface, such as a computer screen, which allows an operator to perform an action based on the output. In other embodiments, the devices can perform or assist in docking (including, e.g., gross positioning and/or fine positioning). For example, the device 166 can be configured to automatically position itself based on the received output. In further embodiments, the structure 12 can include a position sensor which senses a position of the device 166, and a transmitter that transmits steering signals to the device 166. In such cases, the device 166 includes a receiver, which receives the steering signals and steers itself into a desired position relative to the structure 12 based on the steering signals. Other communication techniques can also be used in other embodiments.

Figure 6A:
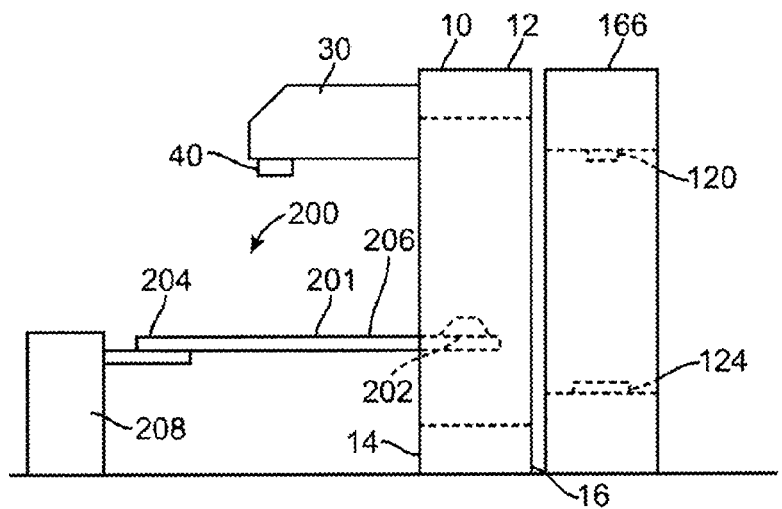
FIG. 6A illustrates a side view of a patient support system in accordance with some embodiments, showing the patient support system placed on one side of the radiation system of FIG. 1A.

FIG. 6A illustrates a patient support system 200 that can be used with any of the embodiments of the radiation system 10 described herein, or with any radiation system, such as a treatment device or a diagnostic device. The patient support system 200 includes a patient support 201 having a first end 202, a second end 204, and a support surface 206 that extends between the first and second ends 202, 204. In some embodiments, the support surface 206 of the patient support 201 can include a plurality of envelopes that can be filled with a fluid (gas or liquid). The envelopes can be selectively filled to create a desired topography of the support surface 206, thereby allowing a patient to be correctly placed on the support surface 206. For example, in some embodiments, the envelopes adjacent the perimeter of the support surface 206 can be selectively filled to create a recess in a center portion of the support surface 206. Alternatively, small individual regions can have mechanically or thermally positionable mechanisms to provide various shapes in the support surface. The shape of the support surface 206 can accommodate a shape of a patient or a portion thereof. The precise shape for a given patient determined, e.g., during treatment planning or a previous session, can be stored and used later such that when the patient lies on the support surface 206, the patient will be correctly positioned relative to the support surface 206. In other embodiments, the support surface 206 does not include the envelopes or other positionable mechanism.

Figure 6B:
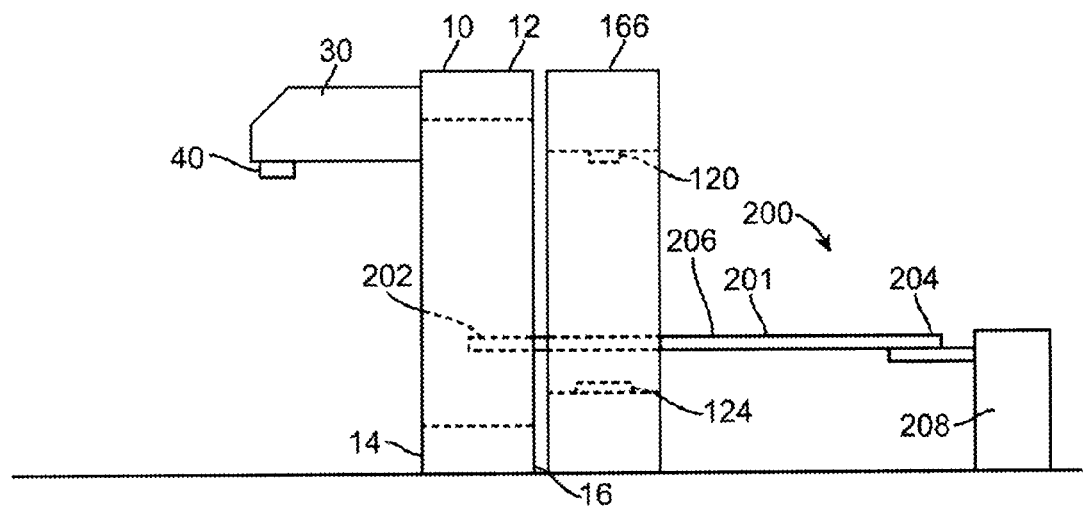
FIG. 6B illustrates a side view of a patient support system in accordance with other embodiments, showing the patient support system placed on another side of the radiation system of FIG. 1A.
Figure 7:
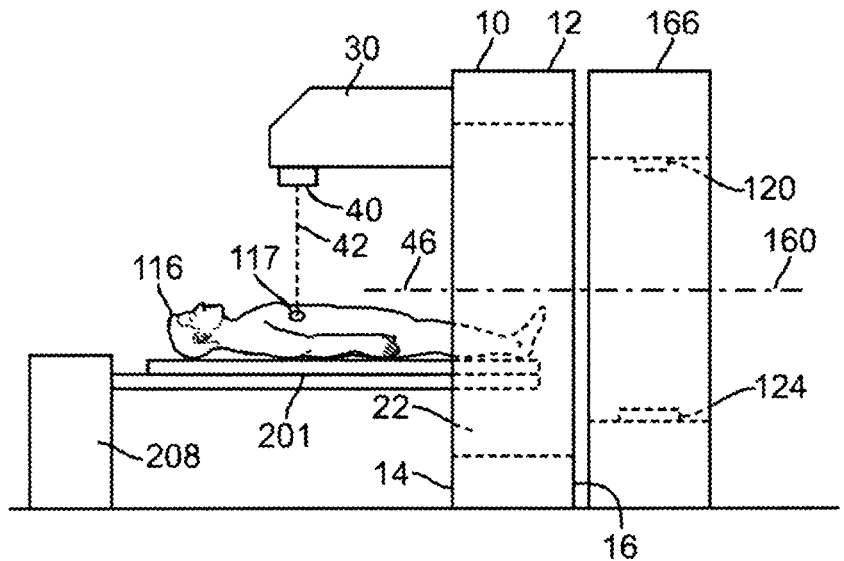
FIG. 7 illustrates a side view of the patient support system of FIG. 6A, showing a patient support of the patient support system being placed at a first operative position.
Figure 8:
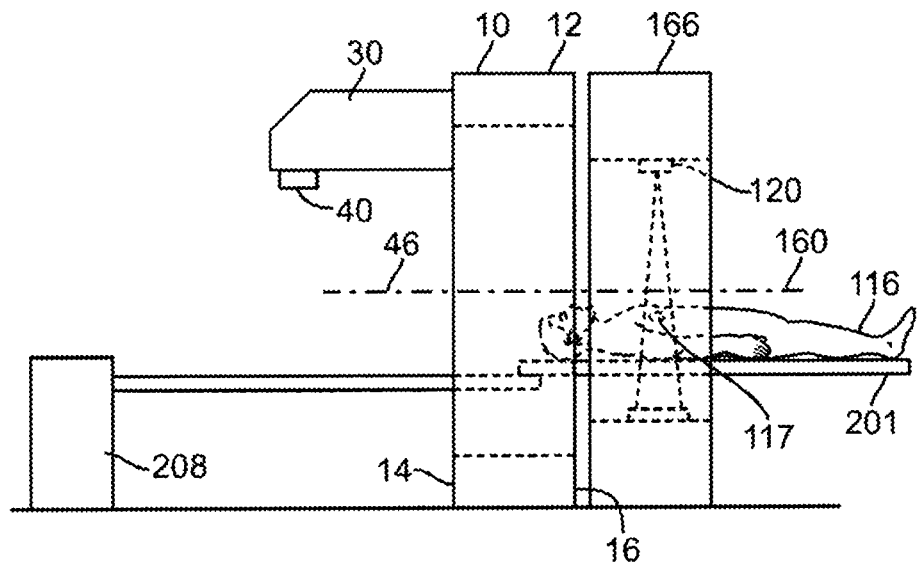
FIG. 8 illustrates a side view of the patient support system of FIG. 6A, showing a patient support of the patient support system being placed at a second operative position.

The patient support system 200 also includes a positioner 208 (represented as a block diagram) for positioning the patient support 201. In particular, the positioner 208 is configured to position the patient support 201 at a first operative position such that radiation beam from the radiation source 40 can be delivered to a portion 117 (e.g., a target region) of the patient 116 (FIG. 7), and a second operative position such that the device 166 can be used to operate on the portion 117 of the patient 116 (FIG. 8). As shown in FIGS. 7 and 8, the portion 117 of the patient 116 is positioned on (adjacent to) the first side 14 of the structure 12 when it is being treated by the radiation source 40, and is positioned on (adjacent to) the second side 16 of the structure 12 (e.g., within a gantry of the device 166) when it is being imaged by the device 166. In the illustrated embodiments of FIGS. 6A, 7, and 8, the patient support system 200 is located on the first side 14 of the structure 12. Alternatively, the patient support system 200 (or any of the patient support systems described herein) can be located on the second side 16 of the structure 12 (FIG. 6B). In such cases, the positioner 208 places the patient support 201 at the first operative position associated with the radiation source 40 by translating at least a part of the patient support 201 past the device 166.

In some embodiments, the device 166 is an imaging device, such as a CT device. In such cases, the positioner 208 can be used to position the patient support 201 (and therefore, the patient 116) at the second operative position associated with the imaging device 166, thereby allowing the imaging device 166 to obtain image data of an internal bodily structure of the patient 116. The obtained image data can then be used to create, or modify, a treatment plan, or to perform patient positioning. In some embodiments, the treatment plan includes parameters (such as a size and shape of a target region, an amount of radiation to be delivered to the target region, margin requirements, etc.) that can be used in a radiation treatment session to treat a portion of the patient 116. Methods of creating treatment plans using image data are known to those skilled in the art.

In some embodiments, the obtained image data can be used to verify a position, orientation, and/or a shape, of a target region (e.g., a tissue intended to be treated with radiation). For example, the obtained image data using the imaging device 166 can be compared against a previously obtained image data associated with the treatment plan to determine whether a target region has changed location, size, or shape. After a position, orientation, and/or a shape of the target region has been verified, the positioner 208 can position the patient 116 to the first operative position, at which the radiation source 40 can be used to deliver radiation beam 42 to treat the patient 116.

In some embodiments, the positioner 208 does not move the patient 116 while radiation is being delivered to the patient 116 from the radiation source 40. In other embodiments, the positioner 208 can be used to move the patient 116 while radiation is being delivered from the radiation source.

In some embodiments, after the patient 116 has been treated, the positioner 208 can be used to position the patient 116 from a first operative position to a second operative position. While the patient 116 is at the second operative position, the imaging device 166 is used to obtain image data of the treated area of the patient 116. The obtained image data can then be used to determine an effect (e.g., an effectiveness, accuracy, etc.) of the previously performed treatment procedure. In some embodiments, the obtained image data can be used to determine a next treatment plan (for a next treatment session) based on a treatment result from an earlier treatment session. For example, the obtained image data may be used to create the next treatment plan, or to modify a previously determined treatment plan, for a next treatment (e.g., next radiation segment, or next radiation session).

It should be noted from the above embodiments that the patient support system 200 is advantageous in that it allows the patient 116 to be treated and imaged without moving the patient 116 from one patient support (e.g., a patient support associated with a treatment device) to another patient support (e.g., a patient support associated with a diagnostic device). This in turn limits, or reduces the risk of, misalignment of the patient 116, and/or misalignment of a target region within the patient 116, relative to a treatment/diagnostic machine. The patient support system 200 is also advantageous because it saves setup time.

Also, in some embodiments, the radiation system 10 may have imaging capability. For example, an imager may be placed opposite the source 40. Moreover, one or more diagnostic x-ray sources and imager(s) opposite the source(s) may be provided. In some embodiments, one or more of the diagnostic sources and one or more imagers may be disposed in the same plane as the treatment source 40. Such image data can be obtained for at least a portion (e.g., a target region) of the patient 116 while the patient 116 is at the first operative position. For example, before or after a treatment session, or in between treatment radiation delivery sessions, the radiation system 10 can deliver radiation energy to image a target region of the patient 116. The obtained image data can be used to verify a position, an orientation, and/or a shape, of the target region, and/or to evaluate an effect of a treatment session. In any embodiment, image data obtained using the imaging capability of system 10 can be processed with image data obtained using one or more of the device 166, and/or one or more images from a previous diagnostic or planning session, for treatment evaluation, treatment planning, and/or patient positioning.

Figure 9:
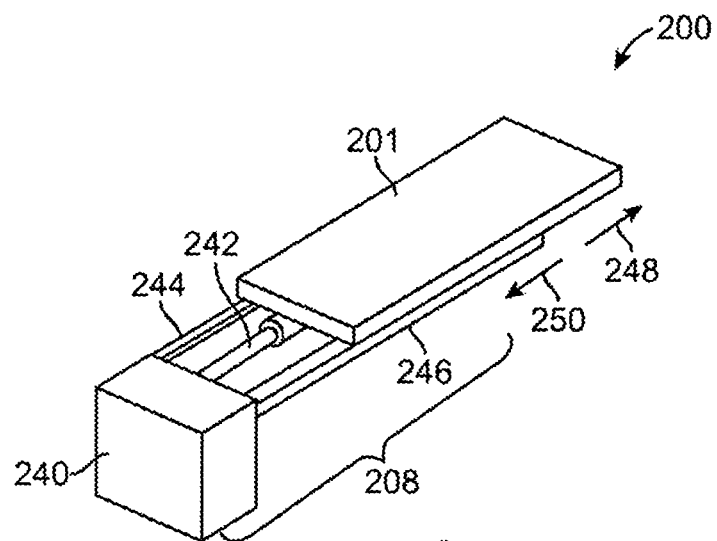
FIG. 9 illustrates a side view of a patient support system in accordance with some embodiments.

FIG. 9 illustrates the patient support system 200 of FIG. 7 in accordance with some embodiments. The patient support system 200 can be used with any of the embodiments of the radiation system 10 described herein, or with any radiation system, such as a treatment device or a diagnostic device. In some embodiments, the positioner 208 includes an actuator 240, a cylinder 242 coupled to the actuator 240, and a set of supports 244, 246, wherein the patient support 201 is slidably coupled to the supports 244, 246. In other embodiments, the supports 244, 246 are part of the patient support 201, in which cases, the positioner 208 does not include the supports 244, 246. During use, the actuator 240 delivers hydraulic pressure to activate the cylinder 242, which in turn, causes the patient support 201 to translate in a first direction indicated by arrow 248. The actuator 240 can also remove hydraulic pressure to activate the cylinder 242, which in turn, causes the patient support 201 to translate in a second direction indicated by arrow 250. The supports 244, 246 provides vertical support for the patient support 201 as the patient support 201 is being positioned by the actuator 240. In some embodiments, the supports 244, 246 are rails, and the patient support 201 includes asset of protrusions (e.g., wheels) that mate with the respective rails. Such configuration allows the patient support 201 to be guided in a desired manner as the patient support 201 is being positioned by the actuator 240.

It should be noted that the patient support system 200 should not be limited to the example discussed previously, and that the patient support system 200 can have other configurations in other embodiments. For example, in other embodiments, instead of the hydraulic pressure actuating cylinder 242, the positioner 208 can include a motor, such as an electric motor, a pneumatic motor, or a piezoelectric motor, for positioning the patient support 201. In some embodiments, the motor couples to a screw shaft and causes the screw shaft to turn. The screw shaft is coupled to the patient support 201, which positions the patient support 201 by rotation of the screw shaft. Also, in other embodiments, the supports 244, 246 can have configurations that are different from that shown in the figure. For example, instead of the bottom side of the patient support 201, the supports 244, 246 can be coupled to the top side of the patient support 201 or to side edges of the patient support 201. In other embodiments, the positioner 208 can be implemented using machineries, devices, and systems that are known in the art of positioning devices.

Figure 10A:
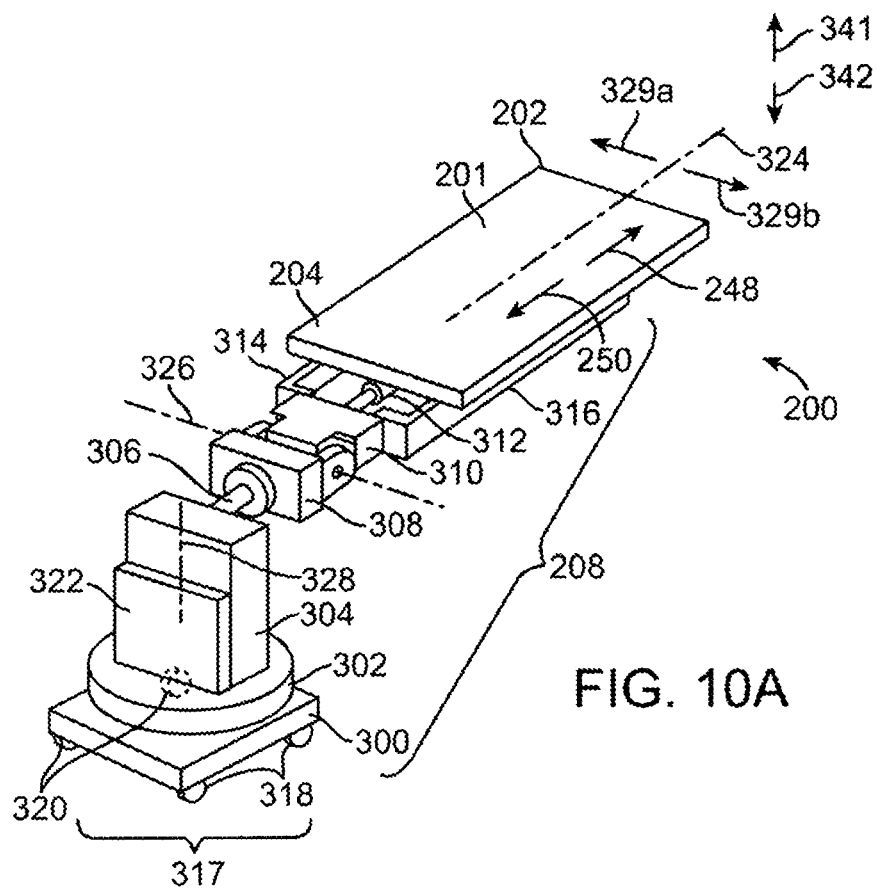
FIG. 10A illustrates a side view of a patient support system in accordance with other embodiments.

In the above embodiments, the patient support system 200 is configured to translate linearly substantially along the axis 46 of the radiation system 10. In other embodiments, the patient support system 200 can also have other degrees of freedom. FIG. 10A illustrates the patient support system 200 having multiple degrees of freedom in accordance with some embodiments. The patient support system 200 can be used with any of the embodiments of the radiation system 10 described herein, or with any radiation system, such as a treatment device or a diagnostic device. In the illustrated embodiments, the positioner 208 includes a first base portion 300, a second base portion 302 that is rotatably coupled to the first base portion 300, a first actuator 304 for turning a shaft 306, a second actuator 308 for rotating a third actuator 310, the third actuator 310, a cylinder 312 coupled to the third actuator 310, and a set of supports 314, 316. The first actuator 304 can be, for example, a motor, that rotates the shaft 306, thereby causing the patient support 201 to roll or rotate about a first axis 324. The second actuator 308 can be, for example, a motor, that causes rotation of the third actuator 310 about a second axis 326, thereby creating an inclined angle or pitch for the patient support 201. The third actuator 310 is configured to actuate the cylinder 312, thereby causing the patient support 201 to translate in directions 248, 250, as similarly discussed previously with reference to FIG. 9. In some embodiments, the positioner 208 can further include a fourth actuator (not shown) for causing the second base portion 302 to rotate relative to the first base portion 300 about a third axis 328. Also, in other embodiments, the positioner 208 can further include an actuator for translating the patient support 201 in the directions 329a, 329b. In further embodiments, the positioner 208 can further include an actuator for changing an elevation of the patient support 201 (e.g., moving the patient support 201 in either of the directions 341, 342). In some embodiments, such feature may be desirable if the bore 22 of the radiation system 10 is offset (e.g., higher or lower) than the bore of the adjacent device (e.g., bore 160 of the device in FIG. 2). In such cases, after the patient has been treated at the first operative position associated with the structure 12, the patient will be moved to the second operative position associated with the adjacent device by translating the patient support longitudinally and raising (or lowering) the patient support. This will ensure that the patient support is located at a desired elevation relative to the second bore. The various actuators described herein can be implemented using machineries, devices, and systems that are known in the art of positioning devices. The axes described herein can be positioned in different locations than those shown herein as desired.

Providing multiple degrees of freedom for the patient support 201 is advantageous in that it allows the patient 116 to be treated or imaged in different configurations, and allows matching of patient position and/or orientation from session to session (e.g., from a first imaging session to a second imaging session, from a first treatment session to a second treatment session, and/or from a treatment session to an imaging session, or vice versa). For example, in some embodiments, the patient support 201 can be rotated about the axis 324 to place the patient 116 in a desired orientation before the radiation source 40 is used to deliver radiation to the patient 116. In other embodiments, the patient support 201 can be rotated about the axis 324 while the radiation source 40 is delivering radiation to the patient 116. In some embodiments, the rotation of the patient support 201 about the axis 324 can be used to compensate for slippage of the radiation source 40 relative to the structure 12. In other embodiments, the patient support 201 can be rotated about the axis 324 in accordance with a treatment plan to thereby allow a target region of the patient 116 to be treated from different angles. Providing for pitch (e.g. rotation about axis 326) and/or yaw (e.g. rotation about axis 328) type motions allow for providing non coplanar fields. In further embodiments, the positioning (in any or a combination of the degrees of freedom described herein) provided by any of the embodiments of the patient positioning system 200 may be used to execute and/or update a treatment plan. For example, instead of or in addition to modifying a gantry angle, a position of the patient in one or more axes may be modified based on images of the patient.

As shown in the figure, the patient support system 200 has a cantilever configuration. To eliminate, or at least reduce, the effect of tipping due to the cantilever configuration, the patient support system 200 further includes a weight 322 secured to the second base portion 302. In other embodiments, the patient support system 200 does not include the weight 322. For example, if the first actuator 304 is made sufficiently heavy to prevent tipping of the patient support 201, then the weight 322 is not needed. Also, in other embodiments, instead of the cantilever configuration shown, the patient support system 200 can have other configurations, such as a simply supported configuration, which includes an additional support (not shown) for supporting the first end 202 of the patient support 201. In further embodiments, the patient support system 200 is secured to a floor, a platform, or a structure, such as a rotatable platform. Rotatable platform will be described later with reference to FIGS. 13A and 13B.

In the illustrated embodiments, the patient support system 200 further includes a docking device 317 which allows the patient support system 200 to be docked into a desired position. In some embodiments, the docking device 317 includes a first set of rollers 318 on a first side of the first base portion 300, and a second set of rollers 320 on a second side of the first base portion 300. In other embodiments, the docking device 317 can have less than two (e.g., one) set of rollers, or more than two sets of rollers. Also, in other embodiments, the docking device 317 can have less than two rollers 318/322 or more than two rollers 318/322 per set. Alternatively, any technique or device for moving the patient support 200, including any of those described in conjunction with moving device 166 described earlier, may be used.

Figure 10B:
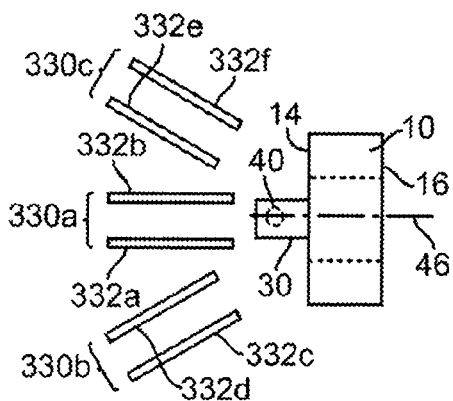
FIG. 10B illustrates a top view of a docking system for allowing a patient support system to be docked adjacent to a radiation system in accordance with some embodiments.

FIG. 10B illustrates a top view of an environment in which the patient support system 200 of FIG. 10A can be used. As shown in FIG. 10B, three sets 330a-330c of rails are provided adjacent to the radiation system 10. The first rail set 330a includes first and second rails 332a, 332b, the second rail set 330b includes first and second rails 332c, 332d, and the third rail set 330c includes first and second rails 332e, 332f. The rails 332a, 332b of the first set 330a are configured (e.g., sized and shaped) to mate with the sets 318, 320 of rollers, respectively. The rails 332c, 332d of the second set 330b are configured (e.g., sized and shaped) to mate with the sets 318, 320 of rollers, respectively. The rails 332e, 332f of the third set 330c are configured (e.g., sized and shaped) to mate with the sets 318, 320 of rollers, respectively. In other embodiments, instead of having three sets 330a-330c of rails 332. Less than three sets (e.g., one set), or more than three sets of rails can be provided. Also, in other embodiments, instead of having two rails 332 per set 330, each set 330 can have less than two rails 332 or more than two rails 332.

In some embodiments, the position of one or both of the sets 318, 320 of rollers of the patient support system 200 can be adjusted such that the patient support system 200 can be mated with rails having different configurations. For example, in some embodiments, the distance between the sets 318, 320 of rollers can be varied such that the patient support system 200 can be docked with rails having different spacing. Also, in other embodiments, one or more rollers can be removed or added to the patient support system 200 for allowing the patient support system 200 to dock with a rail system having different number of rails. In some embodiments, the docking system 317 of the patient support system 200 can further include the rails 332.

In other embodiments, the position of one or both of the rails 332 in each rail set 330 can be adjusted such that the rail system can accommodate different patient support systems having different configurations. For example, in some embodiments, the distance between the rails 332 in each set 330 can be varied such that patient support systems 200 having different roller spacing can be docked. Also, in other embodiments, one or more rails can be removed or added for allowing patient support systems 200 having different number of rollers to be docked.

It should be noted that the docking device 317 of the patient support system 200 should not be limited to the examples discussed previously, and that the docking device 317 can have other configurations in other embodiments. For example, in some embodiments, the docking device 317 can have a first portion associated with the patient support system 200, and a second portion associated with the radiation system 10, wherein the first portion and/or the second portion are configured to mate with each other. The first and second portions of the docking device 317 can be implemented using any machinery, device, or system known in the art. As such, the docking device 317 of the patient support system 200 may or may not include rollers, and may or may not include rails 332. In further embodiments, any of the features or components described with reference to FIGS. 4 and 5 may be used to implement the docking device 317.

Figure 10C:
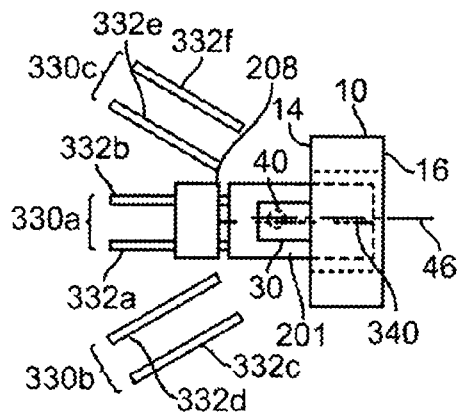
FIG. 10C illustrates a top view of the patient support system of FIG. 10A docked adjacent to the radiation system of FIG. 1A in a first configuration in accordance with some embodiments.
Figure 10D:
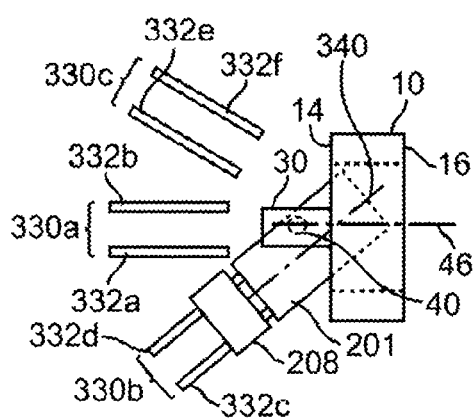
FIG. 10D illustrates a top view of the patient support system of FIG. 10A docked adjacent to the radiation system of FIG. 1A in a second configuration in accordance with other embodiments.
Figure 10E:
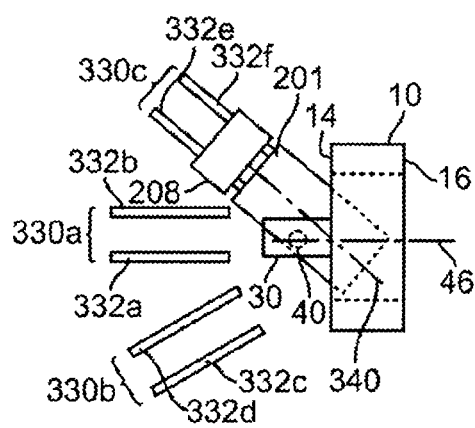
FIG. 10E illustrates a top view of the patient support system of FIG. 10A docked adjacent to the radiation system of FIG. 1A in a third configuration in accordance with other embodiments.
Figure 10F:
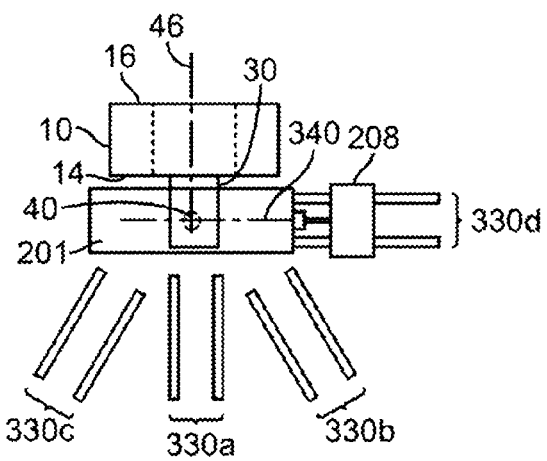
FIG. 10F illustrates a top view of the patient support system of FIG. 10A docked adjacent to the radiation system of FIG. 1A in a fourth configuration in accordance with other embodiments.

In one method of use, the patient support system 200 of FIG. 10A can be docked into a desired position relative to the radiation system 10 using the first set 330a of rails 332a, 332b (FIG. 10C). As shown in FIG. 10C, a longitudinal axis 340 of the patient support 201 is substantially parallel (e.g., within a prescribed range of angles, such as between 0° to 20°) with the axis 46 of the bore 22 of the radiation system 10. In such configuration, at least part of the patient support 201 can be positioned through the bore 22. In another method of use, the patient support system 200 of FIG. 10A can be docked into a desired position relative to the radiation system 10 using the second set 330b of rails 332c, 332d (FIG. 10D). When docked using the second set 330b of rails 332c, 332d, the longitudinal axis 340 of the patient support 201 is substantially non parallel (e.g., forming an angle that is larger than a prescribed value, such as, 50) with the axis 46 of the bore 22 of the radiation system 10. Such configuration allows the patient 116 supported on the patient support 201 to be treated in a non-coplanar manner. In yet another method of use, the patient support system 200 of FIG. 10A can be docked into a desired position relative to the radiation system 10 using the third set 330c of rails 332e, 332f (FIG. 1E). Such configuration allows the patient 116 supported on the patient support 201 to be treated in another non-coplanar manner. In yet another method of use, the patient support system 200 of FIG. 10A can be docked next to the radiation system 10 in a side-by-side manner using a fourth set 330d of rails (FIG. 10F). Such configuration allows the patient 116 supported on the patient support 201 to be treated in another non-coplanar manner. In some cases, for any of the configurations of FIGS. 10C-10E, the position and/or orientation of the patient support 201 can be further adjusted (e.g., by translating and/or rotating the patient support 201) after the patient support system 200 is docked.

In other embodiments, instead of, or in addition to, having the rail sets 330 adjacent to the first side 14 of the radiation system 10, one or more rail sets can be provided adjacent to the second side 16 of the radiation system 10. Such configuration allows the patient support system 200 to be docked adjacent to the second side 16 of the radiation system 10, thereby allowing the patient support 201 to be inserted into the bore 22 of the radiation system 10 from the second side 16 of the radiation system 10. For example, in other embodiments, the device 166 can be first docked next to the radiation system 10. The patient support system 200 is then docked next to the device 166, thereby allowing the patient support 201 to be inserted into the bore 22 of the radiation system 10 through at least a portion of the device 166.

Figure 10G:
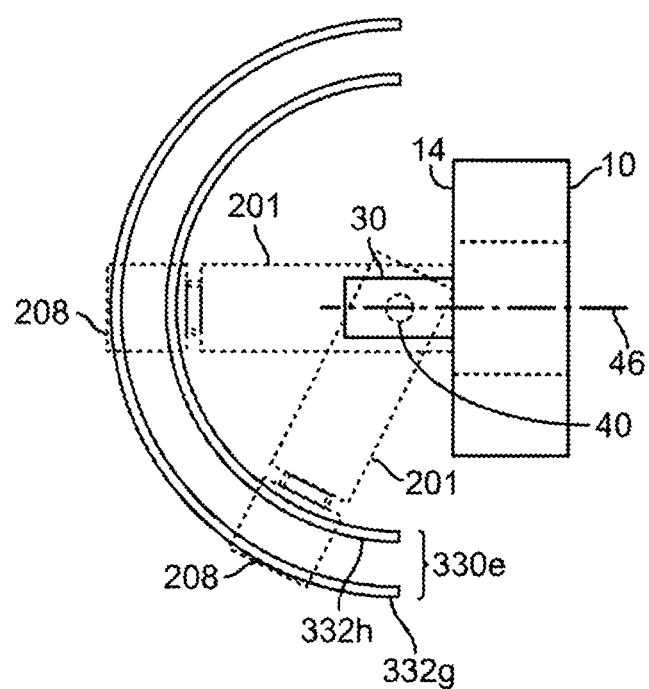
FIG. 10G illustrates a top view of a docking system in accordance with other embodiments.

In other embodiments, instead of providing multiple sets of rails, a single set of rail(s) may be provided for allowing the patient support system 200 to be placed at different positions relative to the radiation system 10. FIG. 10G illustrates a set 330e of rails 332g, 332h that are positioned next to the radiation system 10. Each of the rails 332g, 332h has an arc shape, which allows the patient support system 200 to be slid in a curvilinear manner around the radiation system 10. This in turn allows the patient support system 200 to be placed at different positions relative to the radiation system 10. In other embodiments, the rail set 330e can have more than two rails or less than two rails (e.g., one rail). In some embodiments, the patient support system 200 is detachably coupled to the rail set 330 (e.g., the patient support system 200 can include a docking system for allowing the patient support system 200 to be docked against the rail set 330).

Figure 10H:
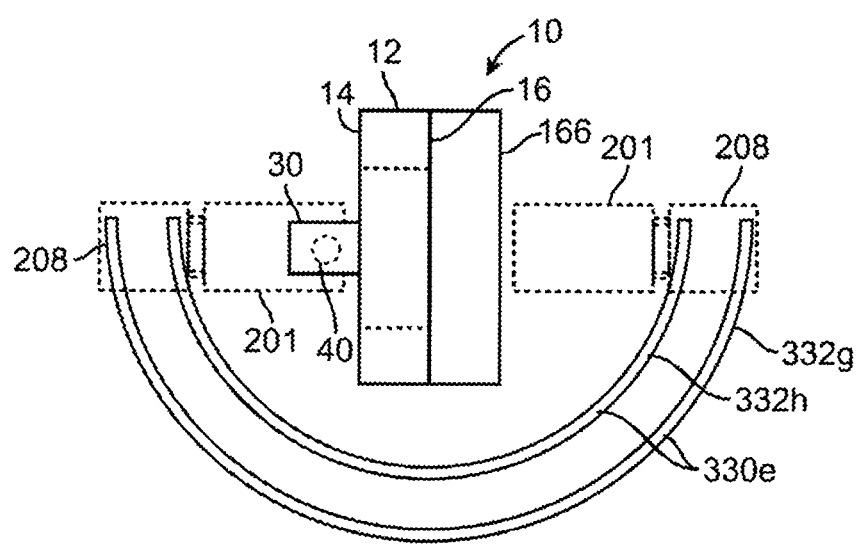
FIG. 10H illustrates a top view of a docking system in accordance with other embodiments.

In further embodiments, the rail set 330e can have different configurations. For example, as shown in FIG. 10H, the rail set 330e can have an arc shape that allows the patient support system 200 to be positioned from one side of the structure 12 (e.g., at the first operative position associated with the radiation source 40), to another side of the structure 12 (e.g., at the second operative position associated with the device 166). In alternative embodiments, the rail set 330e can have a ring configuration that loops substantially around the radiation system 10 and the device 166. In the embodiment of FIG. 10H, the patient support surface may be carried along with the other portions of the patient support system 200. Alternatively, the patient support surface may temporarily be engaged with system 10 and/or system 12, as will be described in more detail below, and a portion of the patient support system 200 without the support surface may travel along the rail set 330e and access the support surface from either side.

It should be noted that the patient support system 200 of FIG. 10A should not be limited to the examples described previously, and that the patient support system 200 can have different configurations in other embodiments. In other embodiments, the patient support 201 does not have some, a combination, or all, of the degree of freedom described previously. For example, in some embodiments, the positioner 208 does not include the first actuator 304, the second actuator 308, or both. Also, in other embodiments, the relative positions of the actuators 304, 308, 310 can be different from that shown in the figure. Further, in other embodiments, the patient support system 200 does not include the docking device 317. In such cases, the patient support system 200 can be fixedly secured to a floor.

Figure 11A:
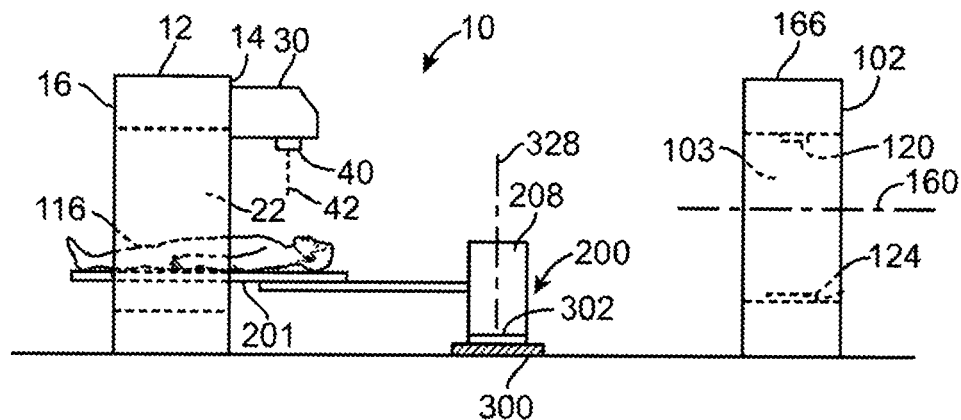
FIG. 11A illustrates a side view of a patient support system placed between a radiation system and a device in accordance with some embodiments, showing a patient support of the patient support system placed at a first operative position.
Figure 11B:
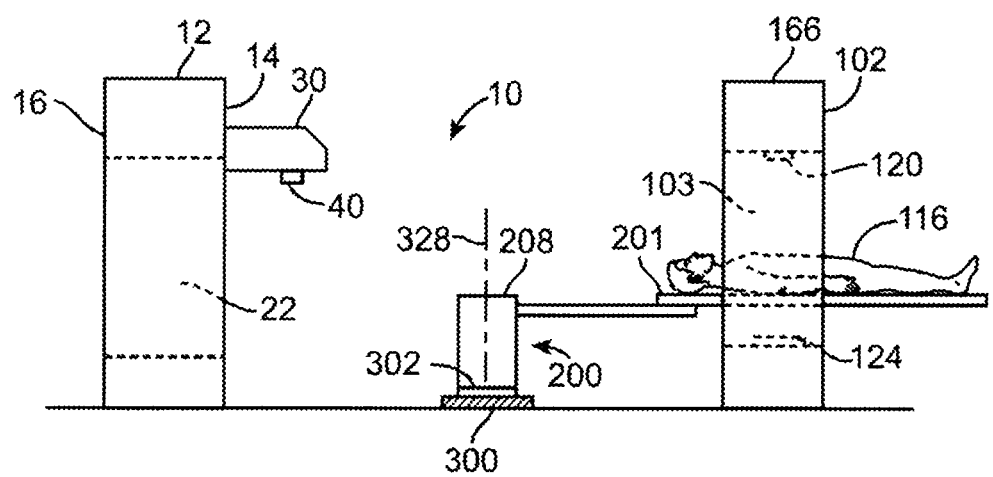
FIG. 11B illustrates a side view of the patient support system of FIG. 11A, showing the patient support of the patient support system placed at a second operative position.

In other embodiments, instead of using the patient support system 200 with the radiation system 10 and the device 166 (e.g., the device 100) having the configuration shown in FIG. 6 (which shows the structure 12 and the device 166 being in a front-to-back or front-to-front configuration), any of the embodiments of the patient support system 200 described herein can be used with the radiation system 10 and the device 166 having other configurations. FIGS. 11A and 11B illustrate the radiation system 10 of FIG. 1, and the device 166, wherein the device 166 is placed closer to the first side 14 than the second side 16 of the structure 12 in a front-to-front configuration. The device 166 is illustrated as the CT device, but can be any of the diagnostic/treatment devices described herein. In such cases, any of the embodiments of the patient support system 200 described herein can be placed between the radiation system 10 and the device 166. During use, the patient support system 200 positions the patient support 201 at the first operative position associated such that the radiation source 40 can be used to deliver the radiation beam 42 to treat the patient 116 (FIG. 11A). If it is desired that the patient 116 be imaged, for example, the patient support 201 is first translated to remove the patient support 201 out of the bore 22 of the radiation system 10. The second base portion 302 of the patient support system 200 is then rotated relative to the first base portion 300 about the axis 328, until the patient support 201 is closer to the device 166 than the radiation system 10. The patient support 201 is then translated axially until the patient support 201 is located at the second operative position at which the patient 116 can be operated by the device 166 (FIG. 11B). The above described operation of the patient support system 200 can be reversed if it is desired to move the patient support 201 from the second operative position associated with the device 166 to the first operative position associated with the radiation source 40.

In other embodiments, instead of using the patient support system 200 in an environment in which the radiation system 10 and the device 166 are placed in a front-to-front manner (such as that shown in FIG. 11A), the patient support system 200 can be placed between the radiation system 10 and the device 166 that are placed in a back-to-back manner. Also, in other embodiments, instead of the radiation system 10 and/or the device 166 described herein, any of the embodiments of the patient support system 200 can be used with other treatment machine and/or diagnostic machine. For example, in some embodiments, the patient support system 200 can be placed between a radiation treatment machine having a configuration that is different from that shown in FIG. 1, and a diagnostic machine, such as an imaging device.

Figure 12A:
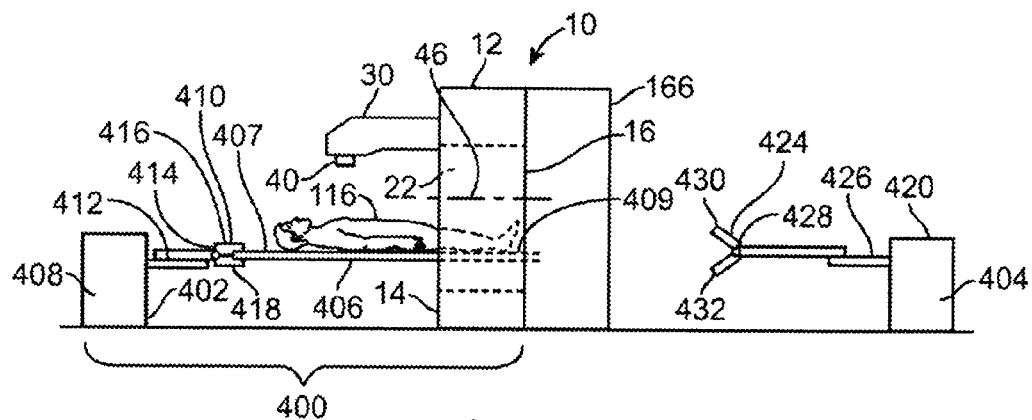
FIG. 12A illustrates a side view of a patient support system having a first positioner, a second positioner, and a patient support in accordance with some embodiments, wherein the patient support is shown coupled to the first positioner.
Figure 12B:
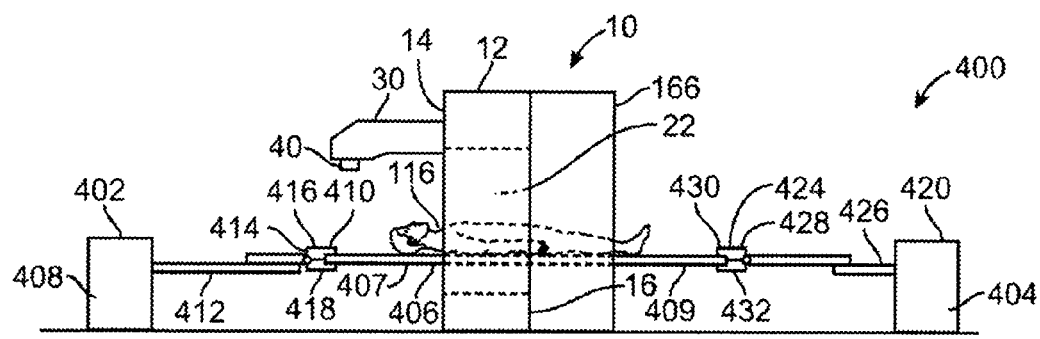
FIG. 12B illustrates a side view of the patient support system of FIG. 12A, showing the patient support being coupled to both the first and the second positioners.
Figure 12C:
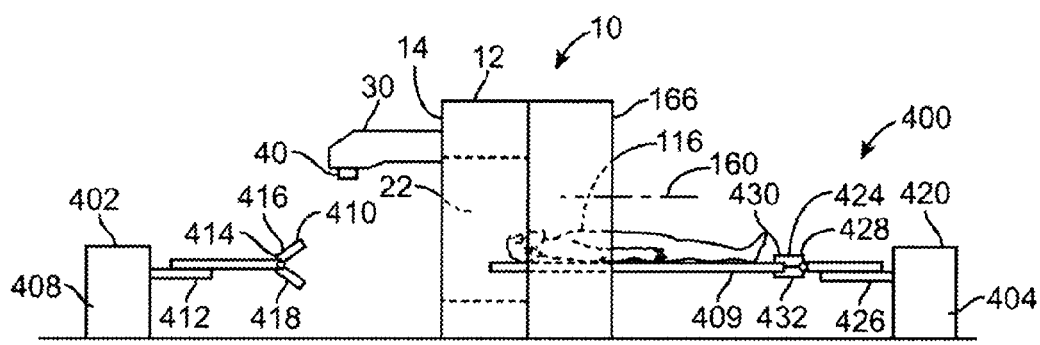
FIG. 12C illustrates a side view of the patient support system of FIG. 12A, showing the patient support being coupled to the second positioner.

FIGS. 12A-12C illustrate a patient support system 400 in accordance with other embodiments. The support system 400 includes a first positioner 402, a second positioner 404, and a patient support 406. The first positioner 402 is located adjacent to the radiation system 10, and the second positioner 404 is located adjacent to the device 166. The patient support 406 has a first end 407 and a second end 409.

The first positioner 402 includes an actuator 408, a coupler 410 that is used to detachably secure the patient support 406 to the positioner 402, and a support system 412 coupled to the patient support 406 and the actuator 408. The actuator 408 can be a motor, a hydraulic mechanism, or other mechanism, and is configured to position the patient support 406 along the axis 46 of the bore 22. As the patient support 406 is being positioned by the actuator 408, the support system 412 provides structural support for the patient support 406. In some embodiments, the support system 412 includes a pair of supports, such as the supports 244, 246 discussed previously with reference to FIG. 9. Alternatively, the support system 412 can have other configurations (e.g., having a platform). In the illustrated embodiments, the coupler 410 includes a jaw assembly 414 having a first jaw 416 and a second jaw 418, and is configured to engage with the first end 407 of the patient support 406. As shown in FIG. 12A, the jaw assembly 414 is in a closed position, thereby detachably coupling the patient support 406 to the first positioner 402. In other embodiments, instead of the jaw assembly 414, the coupler 410 can have other configurations that allow the coupler 410 to detachably secure to a portion of the patient support 406. For example, in other embodiments, the coupler 410 can include one or more dowels or protrusions that are sized to be inserted in respective slot(s) at the patient support 406. The dowel(s) or protrusion(s) may be used to provide moment resistance resulted from the patient 116 being supported on the patient support 406. The coupler 410 may further include a locking mechanism for securing to the patient support 406 after the dowel(s) or protrusion(s) have been inserted into respective slot(s). In further embodiments, the coupler 410 may have other types of securing mechanisms for detachably coupling to the patient support 406. Also, in alternative embodiments, instead of the first end 407, the coupler 410 can engage with other portion(s) of the patient support 406.

In some embodiments, the second positioner 404 may be similar to the first positioner 402, and includes an actuator 420, a coupler 424 that is used to detachably secure the patient support 406 to the second positioner 404, and a support system 426 coupled to the patient support 406 and the actuator 420. The actuator 420 can be a motor, a hydraulic mechanism, or other mechanism, and is configured to position the patient support 406 along the axis 160 of the lumen 122. As the patient support 406 is being positioned by the actuator 420, the support system 426 provides structural support for the patient support 406. In some embodiments, the support system 426 includes a pair of supports, such as the supports 244, 246 discussed previously with reference to FIG. 9. Alternatively, the support system 426 can have other configurations. The coupler 424 includes a jaw assembly 428 having a first jaw 430 and a second jaw 432, and is configured to engage with the second end 409 of the patient support 406. In other embodiments, instead of the jaw assembly 428, the coupler 424 can have other configurations that allow the coupler 424 to detachably secure to a portion of the patient support 406. Also, in alternative embodiments, instead of the second end 409, the coupler 424 can engage with other portion(s) of the patient support 406.

In other embodiments, the second positioner 404 can have a configuration that is different from the first positioner 402. For example, in other embodiments, the second positioner 404 can have number of degrees of freedom, and/or degrees of freedom, that are different from those of the first positioner 402.

The patient support system 400 can be used to position the patient 116 at a first operative position (e.g., the position of the patient 116/patient support 406 at which the patient 116 can be treated by the radiation source 40), and at a second operative position (e.g., the position of the patient 116/patient support 406 at which the patient 116 can be operated by the device 166). For example, as shown in FIG. 12A, the coupler 410 can engage with the patient support 406 to thereby allow the actuator 408 to control a position of the patient support 406. In some embodiments, the actuator 408 is coupled to a processor (such as any of the processors described herein), which controls an operation of the actuator 408. For example, the processor 84/134 can provide signals to the actuator 408 to cause the actuator 408 to position the patient support 406 along the axis 46 during, or in between, radiation delivery sessions.

If it is desired to place the patient 116 at the second operative position, the actuator 408 then advances the patient support 406 further into the bore 22 until the second end 409 of the patient support 406 is engaged with the coupler 424 of the second positioner 404 (FIG. 12B). When the coupler 424 is engaged with the second end 409, the jaws 430, 432 of the jaw assembly 428 are closed to grab onto the second end 409 of the patient support 406. After the coupler 424 is engaged with the patient support 406, the coupler 410 of the first positioner 402 is then disengaged (e.g., by opening the jaw assembly 414) with the first side 407 of the patient support 406 (FIG. 12C). The patient support 406 can then be positioned by the second positioner 404 until the patient support 406 is at the second operative position. During use of the device 166, the second positioner 404 can be used to position the patient support 406 along the axis 160 associated with the device 166.

In other embodiments, the patient support system 400 can have configurations that are different from those described previously. For example, in other embodiments, the patient support system 400 can include other types of mechanical devices or systems that allow the patient support 406 to be passed from one positioner to another positioner. Also, in other embodiments, the radiation system 10 and/or the device 166 can have a mechanical component that temporarily engages the patient support 406 before the patient support is passed from a first positioner to a second positioner. In such cases, the first positioner may or may not engage with the patient support 406 while the radiation system 10 and/or the device 166 is engaged with the patient support 406. In some embodiments, a single positioner can be used such that after the system 10 and/or system 166 has engaged the patient support 406, the positioner is moved to the opposite side to engage the patient support 406 from that side.

In further embodiments, the radiation system 10 or the device 166 can include a positioner for positioning the patient support 406. In such cases, the patient support system 400 does not include the positioner 404 (or the positioner 402), and the positioner 402 (or the positioner 404) can be used to position the patient support 406 through a first range of positions, and pass the patient support 406 to the positioner of the radiation system 10 or the device 166, which can be used to position the patient support 406 through a second range of positions. The first range of positions and the second range of positions may or may not overlap.

In any of the embodiments of the patient support system 200/400 described herein, the positioner 208 (or positioner 402 or 404) can be coupled to a computer system or a processor, such as the processor 84 of FIG. 1A, the processor 134 of FIG. 2, or a separate processor. The processor can then be used to control an operation of the positioner 208. For example, the processor may be configured (e.g., programmed and/or constructed) to control an amount of movement of the patient support (e.g., rotation about axis 324 to thereby tilt the patient support, and/or other types of movement described herein) during a procedure. In some embodiments, the amount of movement of the patient support is prescribed by a treatment plan, which is executed by the processor during a treatment session. The treatment plan may be one that is determined during a diagnostic session, or alternatively, be one that is determined during a treatment session (for example, the treatment plan determined in a diagnostic session may be modified during a treatment session to result in a modified treatment plan).

In some embodiments, the patient support system 200 can further include one or more position/motion sensors for sensing a position/motion of the patient support 201. The sensed position/motion is then transmitted from the sensor(s) to the processor, which determines an actual position of the patient support 201 based on the sensed position/motion received from the sensor(s). In some cases, the processor can be further configured to position the patient support 201 based on the actual position of the patient support 201 (e.g., having a feedback feature).

Also, in any of the embodiments of the patient support system 200/400 described herein, the patient support system 200/400 can further include one or more markings (not shown), which allows the patient support 201/406 to be registered with the radiation system 10 and/or with the device 166. For example, one or both of the radiation system 10 and the device 166 can include an optical sensor for sensing the marking(s) of the patient support system 200/400, thereby allowing a position of the patient support 201 to be determined. The optical sensor can be, for example, a camera or an infrared position sensor. In some embodiments, the optical sensor is coupled to the processor, which receives position signals from the optical sensor. Based on the received position signals, the processor then determines an actual position of the patient support 201.

It should be noted that the patient support system 200/400 can have other configurations in other embodiments. For example, in other embodiments, the patient support system 200 can have the configuration shown in FIG. 13A. The patient support system 200 of FIG. 13A includes the patient support 201, a patient positioner 208, a first base portion 300, and a second base portion 302 that is rotatably coupled to the first base portion 300. In the illustrated embodiments, the first base portion 300 is coupled (e.g., fixedly secured, or detachably secured) to a platform 262, which is rotatably secured to a floor (or a platform). The platform 262 can rotate about a vertical axis 350 in the directions shown by the double-headed arrow 360*a*. The second base portion 302 is rotatably coupled to the first base portion 301 such that the second base portion 302 is rotatable about vertical axis 352 in the directions shown by the arrow 360*b*. In other embodiments, first base portion 300 and the platform 262 can be implemented as a single unit or structure.

The positioner 208 includes a first arm 366 rotatably secured to the second base portion 302 such that the first arm 366 is rotatable relative to the second base portion 302 in the directions shown by the arrow 360*c*. The positioner 208 also includes a second arm 368 that is rotatably secured to the first arm 366 such that the second arm 368 is rotatable relative to the first arm 366 in the directions shown by the arrow 360*d*. The patient support 201 is slidably secured to a support 370, which in turn, is rotatably secured to the second arm 368. As such, the patient support 201 is rotatable relative to the second arm 368 in the directions shown by the arrow 360*e*, and is slidable relative to the support 370 as indicated by the arrow 360*f*.

During use, the platform 262 can be rotated to place the patient support 201 at a desired position relative to the radiation system 10. Also, in some cases, the second base portion 302 can be rotated relative to the first base portion 300 to place the patient support 201 at a desired position relative to the radiation system 10 (FIG. 13B). As illustrated, the combination of rotating the first base portion 300 about the axis 350, and rotating the second base portion 302 about the axis 352 (and in some cases, further coupled with translation movement 360*f* of the patient support 201) allows the patient support 201 to be oriented at a desired angle 390 relative to the radiation system 10, and be placed in an operative position associated with the radiation system 10 (FIG. 13C). For example, in some cases, after the patient support 201 has been positioned such that a point 380 on the patient support 201 is located at a desired location, the movements of the base portions 300, 302 (and in some cases, together with translation of the patient support 201) may allow the patient support 201 to be rotated about a vertical axis 384 through the point 380 (as indicated by the arrow 382) to thereby adjust an orientation of the patient support 201 relative to the system 10. Also, in some cases, movements of the arms 366, 368 allows a height (elevation) of the patient support 201 to be adjusted. Further, the patient support 201 may rotate relative to the second arm 368 as the second arm 368 rotates relative to the first arm 366 to thereby remain in a horizontal configuration. The patient support 201 may rotate relative to the second arm 368 while the second arm 368 remains stationary relative to the first arm 366. In such cases, the movement of the patient support 201 allows an angle of tilt of the patient support 201 to be adjusted.

In other embodiments, the patient support 201 of the patient support system 200 may be configured so that it does not translate relative to the arm 368. Also, in further embodiments, the patient support 201 may have other degrees of freedom, such as any or combination of the degrees of freedom described with reference to FIG. 1A. For example, in other embodiments, the patient support 201 may have a roll feature in which the patient support 201 may tilt or rotate about a longitudinal axis 324 of the patient support 201.

Figure 13A:
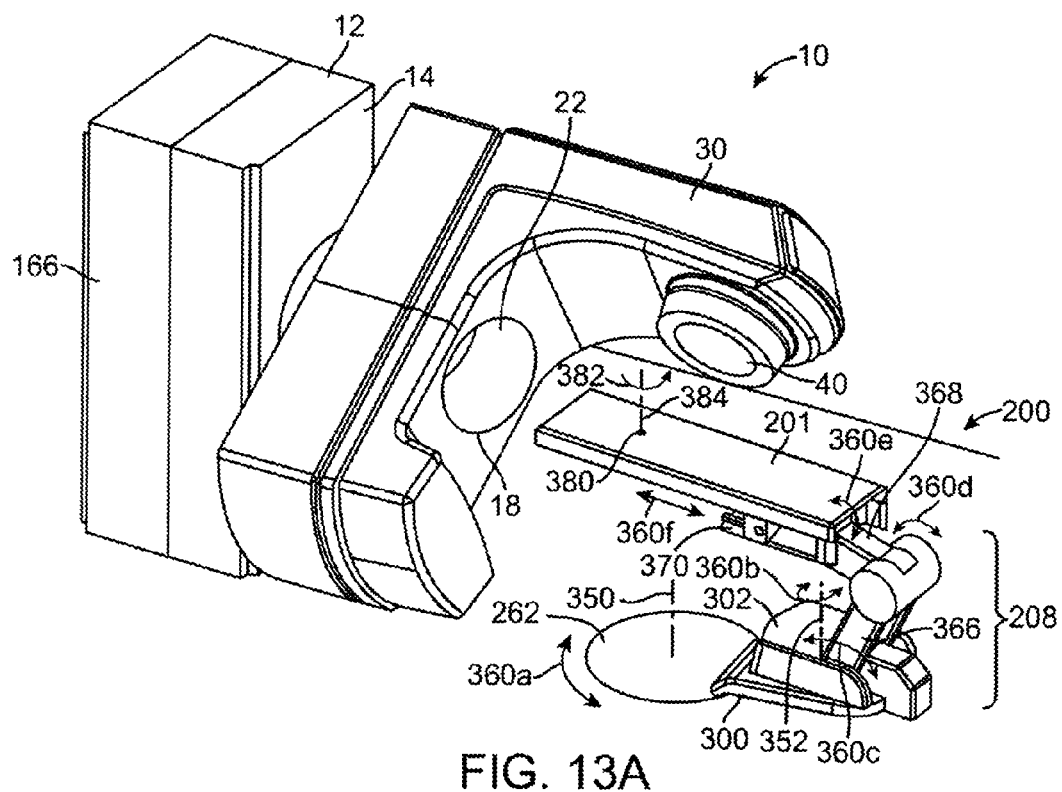
FIG. 13A illustrates a patient support system in accordance with other embodiments.
Figure 13B:
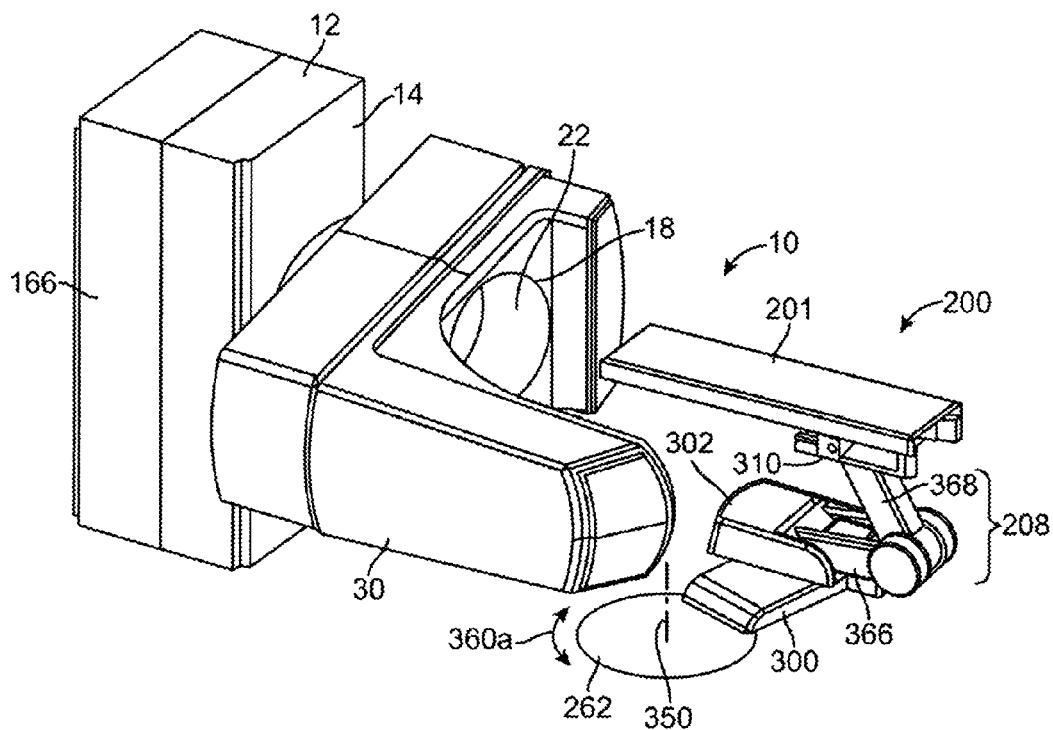
FIG. 13B illustrates a patient support system in accordance with other embodiments.
Figure 13C:
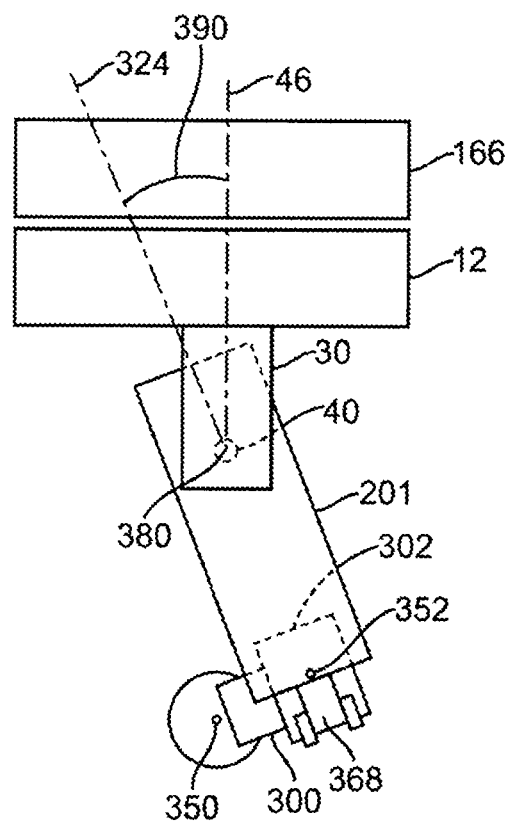
FIG. 13C illustrates a method of using the patient support of FIG. 13A in accordance with some embodiments.

Although the patient support system 200 of FIGS. 13A and 13B is illustrated as being used with the radiation system 10 with the arm 30, in other embodiments, the patient support system 200 of FIGS. 13A and 13B may be used with any of the radiation systems 10 described herein (e.g., the radiation system 10 of FIG. 1F that does not include the arm 30), with any of the devices 166 described herein, and/or with any radiation system not described herein (which may be a treatment machine or a diagnostic machine).

In any of the embodiments of the patient support system 200/400 described herein, the patient support 201/406 can have a feature that allows a surface of the patient support 201 to be customized for different patients. FIG. 13D illustrates a variation of the patient support 201 in accordance with some embodiments. The patient support 201 includes a plurality of support portions 270a-270j that are positionable relative to each other, thereby allowing a desired support surface to be formed. In the illustrated embodiments, support portions 270a-270j are adapted to support a head, left arm, right arm, upper body, mid-body, lower body, left side of a body, right side of a body, thighs, and legs, respectively, of a patient. In some cases, the support portion 270d can be rotated relative to the support portion 270f (as indicated by arrow 274d) to form a convenient position and shape for loading and unloading a patient for treatment and/or imaging. For example, to facilitate patient loading, the patient support can form into a shape of a chair onto which the patient sits. Thereafter, once the patient is in the chair (and positioned and/or immobilized if desired), the patient support forms into a position and/or moves into a location as needed for treatment and/or imaging.

As shown in the embodiments of FIG. 13D, support portion 270a may translate relative to support portion 270d (as indicated by arrow 274b) to accommodate patients with different neck lengths, and may rotate relative to support portion 270d (as indicated by arrow 274a) to adjust an angle of tilt of a patient's head. The support portion 270d may also translate relative to support portion 270e (as indicated by arrow 274c) to adjust for patients with different body lengths. The support portions 270g, 270h may rotate (as indicated by arrows 274e) and translate (as indicated by arrows 274f) to hold a patient's body in place and to adjust for patients with different body widths. The support portion 270i may rotate relative to the support portion 270f to adjust an angle of tile of a patient's thighs. The support portion 270j may rotate relative to the support portion 270i to adjust an angle of tile of a patient's legs. The support portions 270b, 270c may rotate (as indicated by arrows 274j), may locally translate (as indicated by arrows 274l), and/or may globally translate (as indicated by arrows 274k) to adjust for different arms positions of the patient. In other embodiments, not all of the support portions 270 of the patient support 201 are moveable as described, and any or a subset of the support portions 270 may be fixed relative to an adjacent support portion. Also, in further embodiments, any of the support portions 270 may have additional degree of movement(s). For example, in other embodiments, the support portion 270i may translate relative to the support portion 270f to adjust for patients with different thigh lengths.

In some embodiments, the patient support 201/406 can further include device(s) for knowing and setting position for each of the supported portions, such as position sensors secured to each of the support portions 270a-270j. In such cases, a memory can be used to store position signals from the position sensors, which represent a desired support configuration of the patient support 201 for a specific user. The memory can store different sets of position signals for different users. Also, a user interface, such as a computer, or a set of buttons, can be used to allow a user to select a desired set of position signals from the memory. In some embodiments, the positioner 208 automatically adjusts the support portions 270a-270j based on the selected set of position signals, thereby placing the support portions 270a-270j in a configuration that was previously selected by a user.

In any of the embodiments described herein, the patient support 201/406 can include a matrix of support portions 276 (FIG. 13E). Each of the support portions 276 can be positioned by a positioner 272 to move in the directions shown by the double headed arrow 271. Such configuration allows the patient support 201 to provide different configurations of the support surface for different users. The positioner 272 may be actuated using a motor, a hydraulic, a pneumatic device, or any of other types of mechanical linkage. In some embodiments, the patient support 201 of FIG. 13E can further include device(s) for sensing position, such as position sensors, and a memory for storing set positions, as similarly discussed previously. The matrix of support portions 276 may be implemented in any of the embodiments of the patient support 201/406 described herein. For example, in some embodiments, any of the support portions 270 in FIG. 13D may be substituted with, or may include, a matrix of the support portions 276. In other embodiments, the matrix of the support portions 276 may be implemented in other embodiments of the patient support 201/406, or in a patient support not described herein.

Figure 14A:
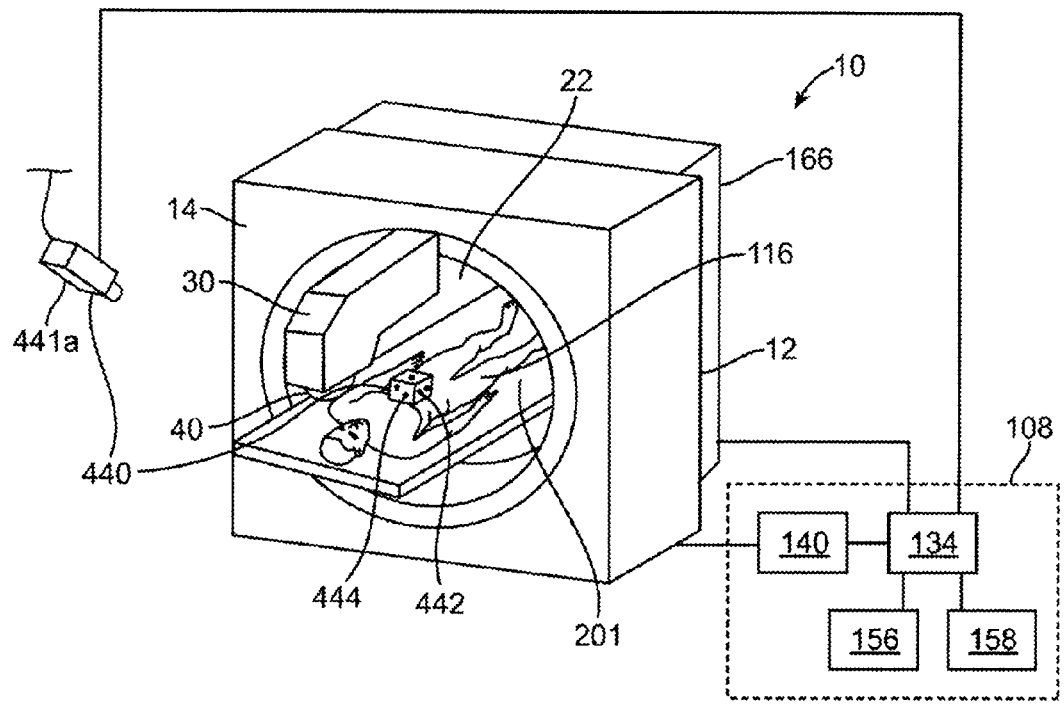
FIG. 14A illustrates an isometric view of a radiation system that includes a patient position sensing system in accordance with some embodiments.

In any of the embodiments of the radiation system 10 described herein, the radiation system 10 can further include a patient position sensing system 440 (FIG. 14A). The patient position sensing system 440 includes an optical device 441a and a marker block 442. In the illustrated embodiments, the optical device 441a is a camera, such as a CCD camera, but can be other type of optical sensor that is capable of sensing an object. The optical device 441a can be mounted to a ceiling, to the radiation system 10 (e.g., within the bore 22), to the device 166, to the patient support system 200 (e.g., the patient support 201) (FIG. 14C), or to a support stand (not shown). The marker block 442 includes a plurality of markers 444 that are so positioned such that at least some of them can be viewed/sensed by the optical device 441a. The markers 444 can be implemented using reflective objects. In the illustrated embodiments, the optical device 441a is coupled to the processor 134, which controls an operation of the radiation system 10 based on input received from the optical device 441a. Alternatively, the optical device 441 can be coupled to the processor 84 of FIG. 1A, or a separate processor, for processing image signals received from the optical device 441a.

During use, the marker block 442 is secured to the patient 116, and the optical device 441a is used to sense the positions of at least some of the markers 444 on the marker block 442. Based on the sensed positions of at least some of the markers 444, the processor 134 then determines a position and an orientation of the marker block 442. The determined position and orientation of the marker block 442 can then be used to determine whether the patient 116 has moved and/or an amount of movement undergone by the patient 116. In such cases, the processor 134 can be configured to control an operation (e.g., a rotational speed of the radiation source 40 about the patient 116, an activation of the radiation source 40, a de-activation of the radiation source 40, an activation period of the radiation source 40 (duration of radiation delivery), etc.) of the radiation system 10 based on the determined patient movement. In some embodiments, the patient movement is associated with a respiration of the patient 116. In such cases, the processor 134 can be configured to control an operation of the radiation system 10 based on phase(s) of the respiratory cycle of the patient 116. In other embodiments, the processor 134 can be configured to control an operation of the radiation system 10 based on other physiological movements of the patient 116.

In some embodiments, the processor 134 can be configured to gate an operation of the radiation system 10 based on the determined patient movement. For example, in some embodiments, the processor 134 is configured to activate the radiation source 40 when an amplitude of the patient movement is below a prescribed threshold, and de-activate the radiation source 40 when an amplitude of the patient movement is above a prescribed threshold. In another example, the processor 134 is configured to activate the radiation source 40 during a certain prescribed phase(s) of the patient movement (e.g., respiratory movement/cycle), and de-activate the radiation source 40 during another prescribed phase(s) of the patient movement. As used in this specification, the term "phase" refers to a variable that is associated with a degree of completeness of a physiological cycle (e.g., a respiratory cycle). Patient position sensing systems, methods of performing medical procedures based on sensed physiological movement, and methods of gating an operation of a radiation device have been described in U.S. patent application Ser. Nos. 09/178,383, 09/893,122, 10/664,534, 10/454,754, 10/234,658, 10/305,416, 10/656,478, and 10/655,920, all of which are expressly incorporated by reference herein.

It should be noted that the patient position sensing system 440 should not be limited by the configuration described previously, and that the patient position sensing system 440 can have other configurations in other embodiments. For example, in other embodiments, instead of a single optical device 441a, the patient position sensing system 440 can further include one or more additional optical device(s) 441 for sensing the marker block 442 when the patient 116 is located at the first operative position associated with the radiation source 40. Also, in other embodiments, the patient position sensing system 440 can further include one or more marker block(s) 442; In further embodiments, instead of having a cube configuration, the marker block 442 can have other shapes, such as a semi-spherical shape, a cone shape, or other customized shapes.

Figure 14B:
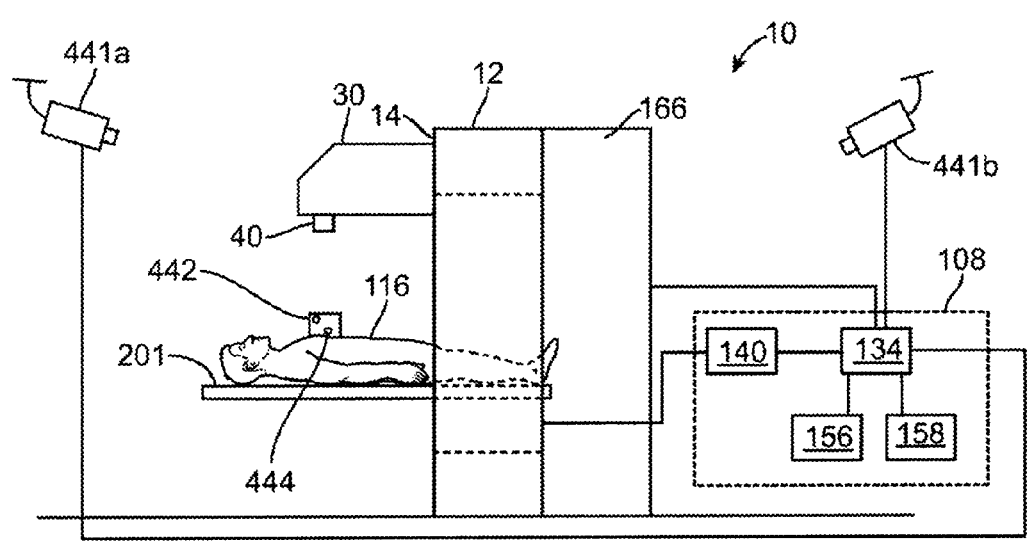
FIG. 14B illustrates a side view of a radiation system that includes a patient position sensing system in accordance with other embodiments.
Figure 14C:
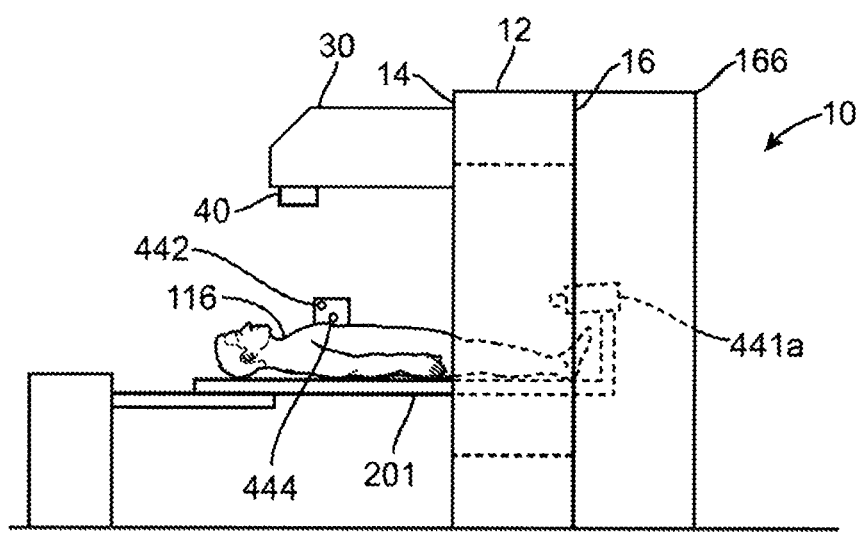
FIG. 14C illustrates a side view of a radiation system that includes a patient position sensing system in accordance with other embodiments.

In other embodiments, instead of, or in addition to, having the optical device 441a for sensing patient movement when the patient 116 is being operated by the radiation source 40, the radiation system 10 can have a second optical device 441b for sensing patient movement when the patient 116 is being operated by the device 166 (illustrated as a block diagram) (FIG. 14B). In such cases, when the patient 116 is positioned at the second operative position associated with the device 166, the optical device 441b can be used to sense patient movement. The sensed patient movement can then be used to control an operation of the device 166, as similarly discussed previously.

In some embodiments, if the optical device 441a is secured to the patient support system 200 (such as that shown in FIG. 14C), then the second optical device 441b is not needed. In such cases, the optical device 441b will be moved with the patient support 201, and the optical device 441 can be used to sense the marker block 442 when the patient is positioned at the first operative position associated with the radiation source 40, and at the second operative position associated with the device 166. In other embodiments, the optical device 441a may be secured at a distance that is sufficiently far away from the first and second operative positions such that it can view both positions in a single field of view. In further embodiments, the optical device 441a may be moveable (e.g., pivotable and/or translatable). For example, if the device 166 is positioned next to the structure 12 in a side-by-side configuration, the optical device 441a may be rotated towards a first direction associated with the structure 12 when the patient is being operated in the first operative position, and may be rotated towards a second direction associated with the device 166 when the patient is being operated in the second operative position. Devices placed in a side-by-side configuration will be described in FIG. 17E.

In some embodiments, the device 166 is a CT device. In such cases, the second optical device 441b is used to determine phases of a physiological cycle as the CT device is used to generate a plurality of images at the plurality of phases of a physiological cycle, wherein each of the images provides an indication of a location of a target region. The processor 134 then creates a treatment plan based at least in part on the plurality of images collected at the plurality of phases in the cycle. After the treatment plan has been created, the patient 116 is then positioned from the second operative position associated with the device 166 to the first operative position associated with the radiation source 40 (e.g., by being translated at least partially through the bore 22 of the structure 12). The radiation source 40 is then used to treat the patient 116 in accordance with the created treatment plan. In some embodiments, the created treatment plan prescribes the phases of a physiological cycle at which radiation is to be delivered to the patient 116, and the amount of radiation to be delivered at the prescribed phases. In such cases, the first optical device 441a can be used to determine patient movement when the patient 116 is at the first operative position, and the radiation source 40 is used to deliver radiation to the patient 116 based on the determined patient movement in conformance with the treatment plan.

In any of the embodiments described herein, instead of using the optical device 441 to sense marker(s) on the marker block 442, the optical device 441 may be used to sense a marker on a patient. For example, the marker may be a print made on a skin of the patient. Alternatively, the marker may be a part of an anatomy of the patient, such as a skin mark on the patient, or a topography/shape of a portion of a patient.

Although the patient position sensing system 440 has been described as having the optical device 441 and the marker block 442, in other embodiments, other position/movement sensing devices can be used as the patient position sensing system 440. As such, the patient position sensing system 440 may or may not include the optical device 441 and the marker block 442. For example, in other embodiments, the patient position sensing system 440 includes one or more infrared position sensors for sensing at least a part of the patient 116. In other embodiments, the patient position sensing system 440 includes one or more magnetic field sensors. In such cases, one or more magnetic devices, such as coils, may be placed within, or secured on, the patient 116. An external electromagnetic coil then provides electromagnetic pulses to interact with the coil(s) within/on the patient 116. Based on the interaction, the position and/or the orientation of the patient 116 can be determined. In alternative embodiments, the patient position sensing system 440 includes one or more sensors, such as RF transponder, ultrasound sensors, or microwave energy sensors (which utilizes technologies that are similar to those used in radar systems), for sensing at least a part of the patient 116. In other embodiments, the patient position sensing system 440 includes one or more ultrasound energy sensors for sensing at least a part of the patient 116. In further embodiments, other devices, such as a strain gauge, or other mechanical/electrical devices, can be used to sense a position/movement of the patient 116.

In further embodiments, the patient position sensing system 440 may be an imaging device. The imaging device may be, for example, a CT device, a laminar tomography device, a MRI device, a fluoroscope, an angiography device, a PET device, a PET-CT device, a SPECT device, or a tomosynthesis imaging device. In such cases, the imaging device may be used to obtain an image of a portion of the patient, and a processor then processes the image to determine a position of a target tissue. For example, the processor may process the image to identify one or more markers implanted at or near a target tissue. Alternatively, the processor may process the image to identify a part of an anatomy of the patient. In some embodiments, the device 166 may be the imaging device that is a part of the patient position sensing system 440.

It should be noted that the method of using the patient position sensing system 440 should not be limited to the examples discussed previously, and that the patient position sensing system 440 can be used to assist determining treatment plans and/or to assist gating of medical procedures in other manners in other embodiments. For example, in other embodiments, the patient movement sensed by the first optical device 441a can be used in a predictive physiological gating procedure, in which the operation of the radiation source 40 is predictively gated based at least in part on the patient movement. Predictive gating of a medical procedure has been described in U.S. patent application Ser. No. 09/893,122.

Further, in some embodiments, the position sensing system 440 can be used to determine a position of the patient support 201. For example, the marker block 442 (or another marker block) can be secured to the patient support, and the optical device 441 is then used to sense the markers on the marker block. Based on the sensed markers, the processor 134 then determines a position and an orientation of the marker block 442 (and therefore, the position and orientation of the patient support 201). In other embodiments, instead of using a marker block, the patient support 201 can include a detectable marker secured to a portion of the support 201.

In the above embodiments, the position sensing system 440 has been described as having the marker block 442. However, in other embodiments, the marker block 442 is not needed, and the position sensing system 440 does not include the marker block 442. For example, in some embodiments, the optical device 441 can be used to sense a portion of a patient, wherein the portion is used as a marker (e.g., a physiological marker). In such cases, a processor (such as the processor 84/134) can be configured to receive image signal from the optical device 441, and process the signal to identify the physiological marker. In some embodiments, the processor can be configured to identify and analyze a topography of a patient surface, and determine a characteristic of the patient, such as an amplitude and/or a phase of a breathing cycle of the patient based on a result of the analysis.

Figure 15:
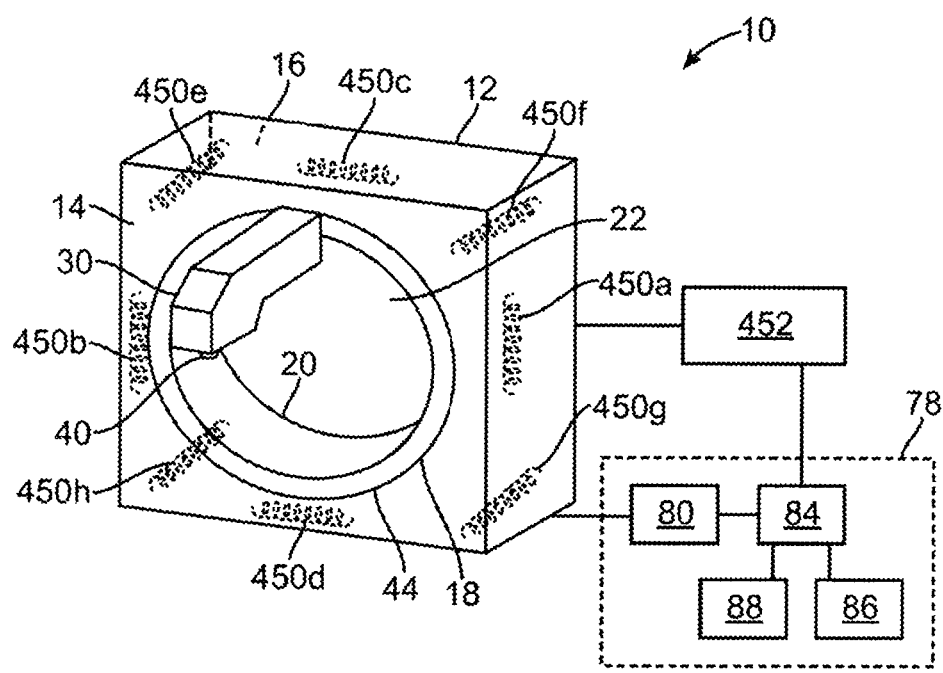
FIG. 15 illustrates an isometric view of a radiation system that includes compensating coils in accordance with some embodiments.

In any of the embodiments of the radiation system 10 described herein, the radiation system 10 can further include one or more compensating coils 450 that are electrically coupled to a generator 452 (FIG. 15). In the illustrated embodiments, the radiation system 10 includes a pair of coils 450a, 450b that are parallel to a x-axis of the radiation system 10, a pair of coils 450c, 450d that are parallel to a y-axis of the radiation system 10, and four coils 450e-450h that are parallel to a z-axis of the radiation system 10. In other embodiments, the number of coils 450 can be different from that shown. For example, in other embodiments, the radiation system 10 can include one coil (e.g., coil 450a) that is parallel to the x-axis, one coil (e.g., coil 450c) that is parallel to the y-axis, and one coil (e.g., coil 450e) that is parallel to the z-axis. Also, in alternative embodiments, the radiation system 10 can include fewer or more than three sets of coils 450, which each set having one or more coils 450. In further embodiments, the orientation and position of the coils 450 can be different from that shown. For example, in other embodiments, the radiation system 10 can include coils 450 that are not orthogonal relative to each other. In the illustrated embodiments, the coils 450 are illustrated as being located within the structure 12. In other embodiments, instead of placing the coils 450 inside the structure 12, some or all of the coils 450 can be secured within the arm 30 of the radiation system 10, the patient support system 200, the device 166, or a separate structure (not shown) that is adjacent to the radiation system 10.

One or more generator, such as generator 452 is configured to selectively provide electrical energy to one or more of the coils 450 to create a desired electromagnetic field having a certain magnitude during an operation of the radiation system 10. In some embodiments, the device 166 may include an electron accelerator that may remain on while the radiation source 40 is used to deliver radiation to the patient 116. In such cases, the electromagnetic field created by the coil(s) 450 is used to compensate (e.g., reduce) interference associated with a magnetic field of the accelerator in the device 166. In other embodiments, a magnetic field of an accelerator in the radiation system 10 may interfere with an operation of the device 166 (especially if the device 166 includes a radiation source). In such cases, the electromagnetic field created by the coil(s) 450 is used to compensate (e.g., reduce) interference resulted from a magnetic field of the accelerator in the radiation system 10. In other embodiments, the magnetic field created by the coil(s) 450 can be used to compensate interference effects due to other components, such as a positioner of a patient support system.

In some embodiments, the generator 452 is coupled to a processor, such as the processor 84 of FIG. 1A, which controls an operation of the generator 452. In other embodiments, instead of using the processor 84, the generator 452 can be coupled to the processor 134, or a separate processor, which controls an operation of the generator 452. The processor 84/134 can be configured (e.g., programmed) to provide activation signals to the generator 452 to cause the generator 452 to activate certain coil(s) 450 during an operation of the radiation system 10. In other embodiments, instead of, or in addition to, providing activation signals, the processor 84/134 can be configured to determine an amount of current to be delivered to each of the coil(s) 450 to be activated. In some embodiments, the magnetic field resulted from the accelerator 31 can be calculated based on operational parameters of the accelerator 31 (such as a position of the accelerator 31, an orientation of the accelerator 31, an/or an amount of current to be delivered to the accelerator 31), and the processor then determines which of the coils 450 to activate to eliminate, or at least reduce the effect of, the magnetic field associated with the accelerator 31. In other embodiments, instead of calculating the magnetic field associated with the accelerator 31, one or more magnetic field sensors can be placed adjacent to the accelerator 31 (such as on or next to the device 166). In such cases, the processor receives signals from the magnetic field sensor(s), and determines which of the coils 450 to activate to eliminate, or at least reduce the effect of, the magnetic field associated with the accelerator 31.

In the above embodiments, the compensating magnetic field is described as being provided by one or more coils 450. Alternatively, instead of, or in addition to, using electromagnetic coils 450, the radiation system 10 can include one or more permanent magnets that provides a magnetic field for compensating (at least in part) magnetic interference.

In any of the embodiments described herein, instead of, or in addition to, including compensating coil(s) and/or magnet(s), the radiation system 10 can further include a shield to prevent, or at least minimize the effect of, interference due to the accelerator 31. For example, a shield (not shown) can be placed between the accelerator 31 and the device 166 to prevent, or at least minimize the effect of, interference due to the accelerator 31. The shield can be made from Mumetal, or other materials. In some embodiments, the shield can be placed around the accelerator 31. In other embodiments, the shield can be placed around the device 166 or a component (e.g., a component that may be affected by a magnetic field from the accelerator 31) of the device 166. In other embodiments, the shield can be secured to the structure 12, such as to the second side 16 of the structure 12. In any embodiment, the coils and/or shield may be used to shield other devices from the a magnetic field such as that generated by the accelerator, such as a MRI device, or a magnetic based sensing device.

Figure 16A:
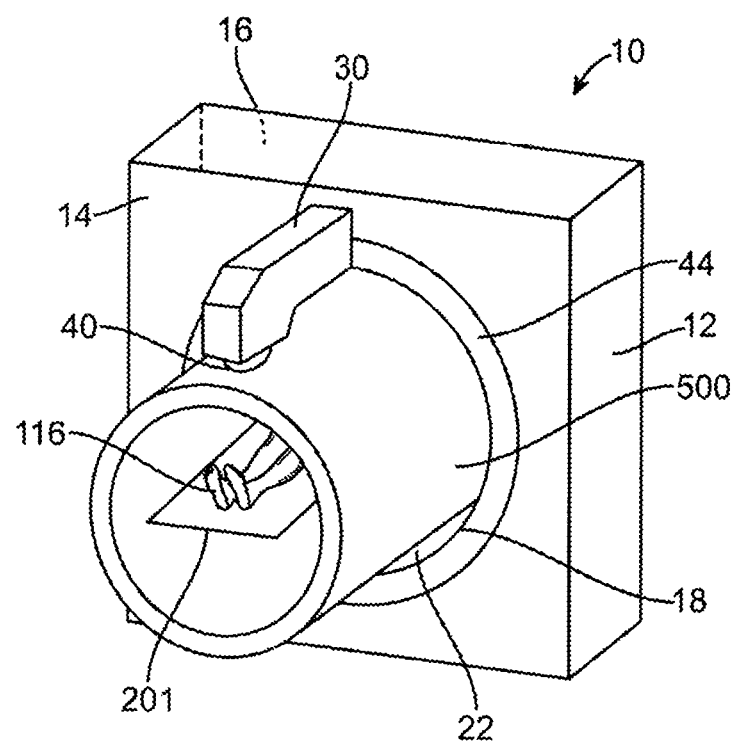
FIG. 16A illustrates an isometric view of a radiation system that includes a protective shield in accordance with some embodiments.
Figure 16B:
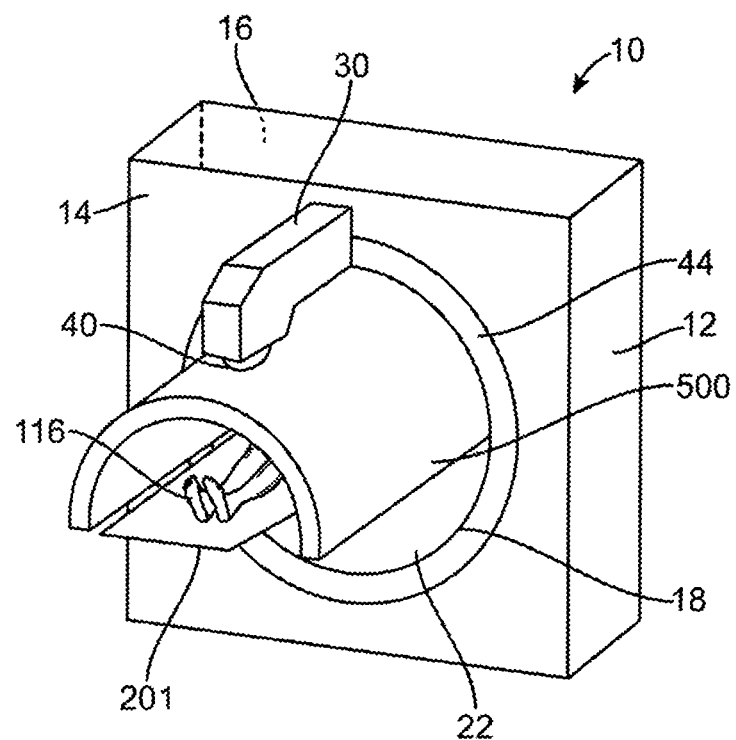
FIG. 16B illustrates a side cross-sectional view of the radiation system of FIG. 16A.

In any of the embodiments of the radiation system 10 described herein, the radiation system 10 can further include a protective guard 500 for protecting the patient 116 (FIG. 16A). The guard 500 can be made from any material, such as carbon fiber, as long as it allows at least some of the radiation from the radiation source 40 to be transmitted therethrough. In the illustrated embodiments, the guard 500 has a circular cylindrical shape, but can have other cylindrical shapes in other embodiments. Also, in other embodiments, the guard 500 can be a partial cylinder (e.g., have an arc shape cross section) (FIG. 16B).

Figure 16C:
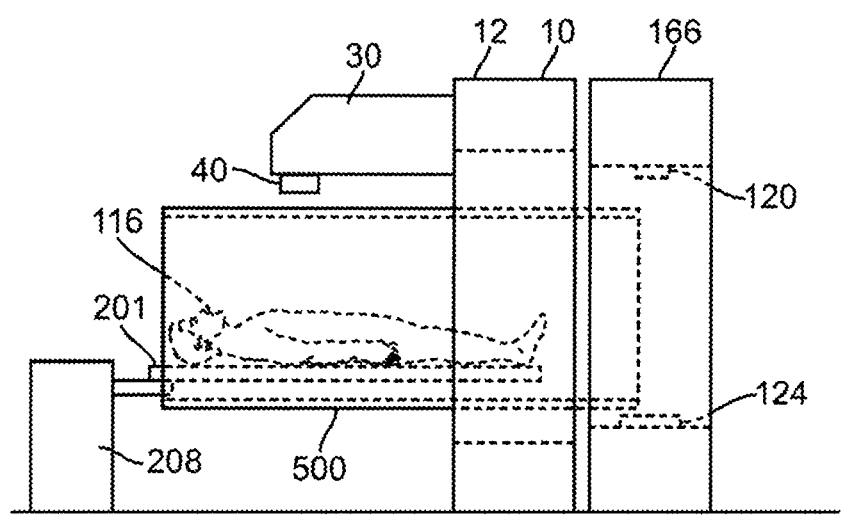
FIG. 16C illustrates an isometric view of a radiation system that includes a protective shield in accordance with other embodiments.

During use, the guard 500 is placed between the patient 116 and the radiation source 40 (FIG. 16C). The guard 500 protects the patient 116 from being collided with the radiation source 40 or the arm 30 of the radiation system 10 as the radiation source 40 is rotating about the patient 116. The guard 500 also allows the arm 30 (and therefore, the radiation source 40) to be rotated about the patient 116 at a faster speed without the risk of injuring the patient 116.

In some embodiments, the guard 500 is detachably coupled to the radiation system 10. In such cases, when the guard 500 is not used, the guard 500 can be detached from the radiation system 10. In other embodiments, the guard 500 is detachably coupled to the patient support system 200. In such cases, when the guard 500 is not used, the guard 500 can be detached from the patient support system 200. In other embodiments, the guard 500 is rotatably secured (e.g., via one or more hinges) to the radiation system 10, which allows the guard 500 to be opened or closed relative to the radiation system 10 between uses. In further embodiments, the guard 500 is slidably secured to the radiation system 10. For example, in some embodiments, the guard 500 can be slid along the axis 46 of the bore 22 to thereby exposed the patient support 201 such that a patient 116 can be placed on the patient support 201. After the patient 116 is placed on the patient support 201, the guard 500 can then be slid to a closed position, such as that shown in FIG. 16C. In further embodiments, the guard 500 can be coupled (e.g., slidably secured, rotatably secured, or detachably secured) to the patient support 201, which allows the guard 500 to be positioned in conjunction with the patient support 201. In such cases, if the patient support 201 is translated along the axis 46 of the bore 22, the guard 500 will move with the patient support 201. In some embodiments, if the patient support 201 is positioned between the first operative position associated with the radiation source 40, and the second operative position associated with the device 166, the guard 500 that is coupled to the patient support 201 will move with the patient support 201. In the case in which the device 166 includes a moving part, such as a rotating gantry, the guard 500 can also protect the patient 116 from being collided with the moving component of the device 166.

In some embodiments, if the guard 500 is coupled to the patient support 201, the guard 500 can be made sufficiently small such that it can fit within the bore 22 of the radiation system 10 in different orientations. Such allows the patient 116 to be treated in different non-coplanar manners. In other embodiments, if the guard 500 is coupled to the radiation system 10, the cross sectional size of the guard 500 (and the bore 22) can be made sufficiently large to allow the patient support 201 to be oriented in a non-coplanar manner within the guard 500. In further embodiments, when treating the patient 116 in a non-coplanar manner, the guard 500 is decoupled (or retracted) from the radiation system 10 and/or the patient support 201, and is not used.

It should be noted that the protective guard 500 is not limited to being used with the radiation system 10 (e.g., any of the radiation systems 10 in FIGS. 1A-1F). In other embodiments, the guard 500 can be used with other treatment devices or imaging devices. For examples, in other embodiments, the guard 500 can be included or used with a conventional CT machine.

In any of the embodiments of the radiation system 10 described herein, the radiation system 10 can further include a guard that covers at least a portion of the arm 30. For example, the guard can be a cylindrical structure, that is placed around the arm 30 and in a coaxial relationship with the bore 22. The guard prevents, or at least reduce the risk of, a collision by the arm against a person, such as an operator of the radiation system 10.

Figure 17A:
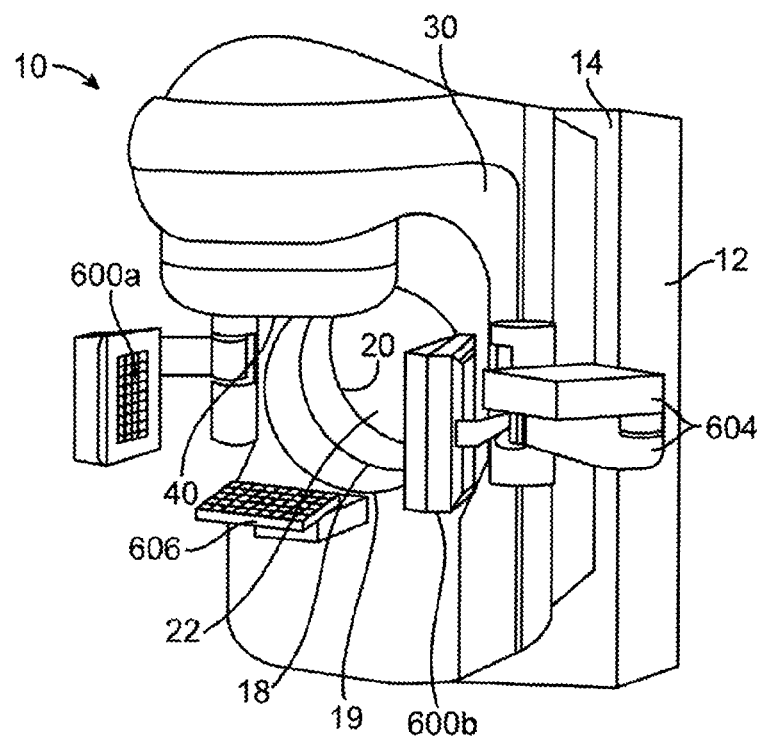
FIGS. 17A-17E illustrate radiation systems in accordance with other embodiments.

In any of the embodiments of the radiation system 10 described herein, the radiation system 10 can further include a PET device secured next to the radiation source 40. FIG. 17A illustrates a variation of the radiation system 10 that includes two PET imagers 600a, 600b. The PET imagers 600a, 600b are located next to the radiation source 40, and opposite from each other across the opening 19. The positions of the PET imagers 600a, 600b can be adjusted using the mechanical linkages 604. In the illustrated embodiments, the radiation system 10 also includes an imager 606, which is similar to the imager 50 discussed previously with reference to FIG. 1B. The imager 606 is located opposite from the radiation source 40 across the opening 19 (at an operative position in association with the radiation source 40). The configuration of the radiation system 10 should not be limited to the examples discussed previously, and that the radiation system 10 can have other configurations in other embodiments. For example, in other embodiments, instead of having the arm 30, the radiation system 10 can have a ring gantry with a slip-ring configuration (e.g., such as that described with reference to FIG. 1F). In such cases, the structure 12 of the radiation system 10 can further include a PET device secured next to the ring gantry. For example, the PET device may comprise imagers 600a and 600b attached to a ring. The radiation source 40 and the imager 606 may also be secured to the same ring. Alternatively, the PET device may include a PET imager having a ring configuration formed as part of the system 10, e.g, within the bore of system 10.

During use, the radiation source 40 can be used to deliver treatment radiation to treat a patient while the patient is positioned at the first operative position associated with the radiation source 40. The radiation source 40 can also be used to deliver low dose radiation to obtain an image (e.g., using the imager 606) of a portion of the patient while the patient is at the first operative position. In such cases, the collimator next to the radiation source 40 may be opened to provide an imaging window for allowing the imaging radiation to pass therethrough. The PET imagers 600a, 600b can be used to obtain PET image data of a portion of the patient while the patient is at the first operative position. Such feature is advantageous in that it allows PET image data from the PET imagers 600a, 600b, and image data from the imager 606, to be collected without moving the patient support. The imagers 600a and 600b can be rotated to obtain data at a plurality of angular positions, to provide more data for volumetric reconstruction.

In some embodiments, the radiation system 10 of FIG. 17A can be used with the device 166, as similarly discussed with reference to FIG. 2. During use, the patient can be placed at the operative position associated with the device 166, and the device 166 can be used to create a treatment plan for the patient. At least a portion of the patient is then transferred from the operative position associated with the device 166, through the bore 22 and the bore 56, to the operative position associated with the radiation source 40, where the patient can be treated and/or imaged by the radiation source 40 and/or the imagers 600a, 600b, or by the imaging devices 51 and 52 of FIG. 1D.

Figure 17B:
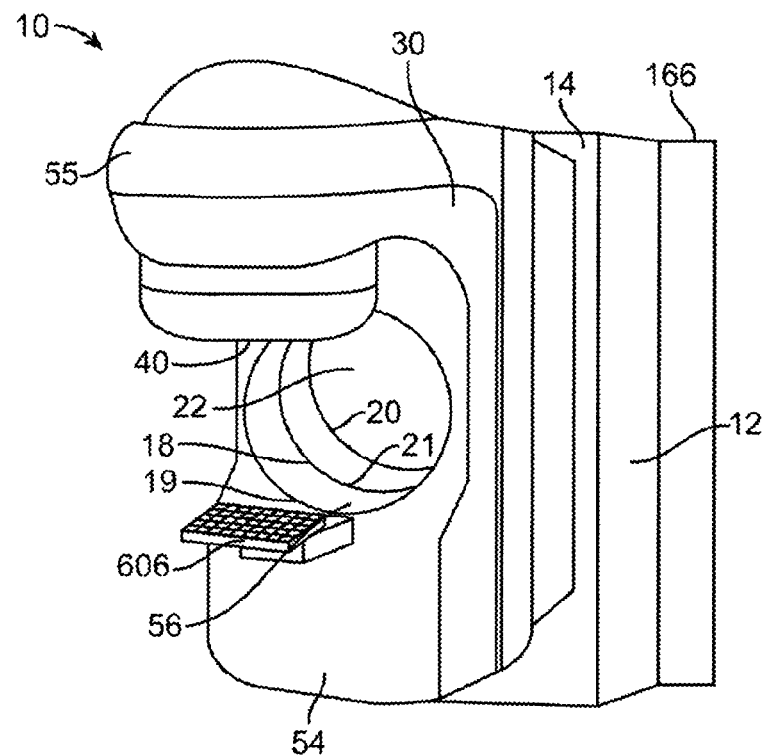

In other embodiments, instead of the configuration shown in FIG. 17A, the radiation system 10 does not include the PET imagers 600a, 600b (FIG. 17B). Instead, the radiation system 10 is used with, or includes, the device 166, which includes PET imager(s) (for example, the device 166 may include two PET imagers (or multiple sets of two imagers) secured to a ring and positioned opposite from each other, or alternatively, the device 166 may include a PET imager having a stationary ring configuration. In such cases, the patient is positioned at the second operative position associated with the device 166, and the PET imager(s) are used to obtain PET image data of a portion of the patient. The portion of the patient is then positioned through the bore 22 of the structure 12 and through the bore 56 of the arm 30 until it is at the first operative position associated with the radiation source 40. The radiation source 40 then delivers low dose radiation beam to obtain image data (e.g., using the imager 606) of the portion of the patient. In other embodiments, the image data can be obtained before the PET image data. The configuration of the radiation system 10 should not be limited to the examples discussed previously, and that the radiation system 10 can have other configurations in other embodiments. For example, in other embodiments, instead of having the arm 30, the radiation system 10 can have a ring gantry with a slip-ring configuration. Also, in other embodiments, instead of, or in addition to, PET imagers, the device 166 can include one or more SPECT imagers. Similarly, in other embodiments, imagers 600a, 600b and/or 606 may be SPECT imagers.

In any of the embodiments described herein, image data obtained using the imager 606 can be used to perform attenuation correction for the PET image data (to correct attenuation effect in PET). This is advantageous because PET photons, having an energy of approximately 511 keV, undergo significant Compton scattering, while attenuation of x-rays of typical diagnostic sources generally are dominated by the photoelectric effect. Photons from the treatment beam are typically in the MeV range, and like the PET photons, the attenuation is dominated by Compton scattering. Thus, the attenuation data from the treatment beam may provide a better measure of attenuation. In addition, since a PET image may not provide a desired image resolution, the image data obtained using the imager 606 can be used to correct certain features of the PET image data. In some embodiments, the image data (whether from imager 606 or other imaging device) and the PET image data are combined to form a composite image, which may be used for treatment planning and/or for treatment evaluation. The composite image may be used during a treatment process. For example, the composite image may be used to verify a location of a target tissue region and/or to show the areas where a tumor is actively growing. As a further exemplary alternative, the imaging devices 51 and 52 may be used to obtain data for attenuation correction, and/or for use in forming a composite image.

Various techniques may be employed for collecting the image data from the imager 606 and the PET image data from the PET imagers 600a, 600b. For example, in some embodiments, the radiation source 40 and the imager 606 may be rotated around the patient to collect a plurality of image data at a plurality of gantry angles. Afterwards, the PET imagers 600a, 600b are then used to collect PET image data. In some cases, the PET imagers 600a, 600b may be rotated around the patient to collect a desired set of PET image data. If a ring-shape PET imager is used (instead of the set of PET imagers 600a, 600b), then the ring-shape PET imager needs not be rotated. In other embodiments, instead of collecting the image data before the PET image data, the PET image data may be collected first, followed by the image data from the imager 606. In further embodiments, a set of image data from the imager 606 and PET image data from the PET imagers 600a, 600b may be collected at a first gantry angle. The gantry is then rotated to thereby collect another set of image data from the imager 606 and PET image data from the PET imagers 600a, 600b at a second gantry angle. The rotation of the gantry, and the collection of image and PET image data are continued, until a desired amount of image data and/or PET image data is collected. The collected image data and PET image data are transmitted to a processor, such as the processor 84, which processes the image data and the PET image data. In some embodiments, the processor uses the image data to perform attenuation correction for the PET image data, as discussed herein.

In other embodiments, the processor may use the image data and the PET image data to construct a composite image, as also discussed herein.

Figure 17C:
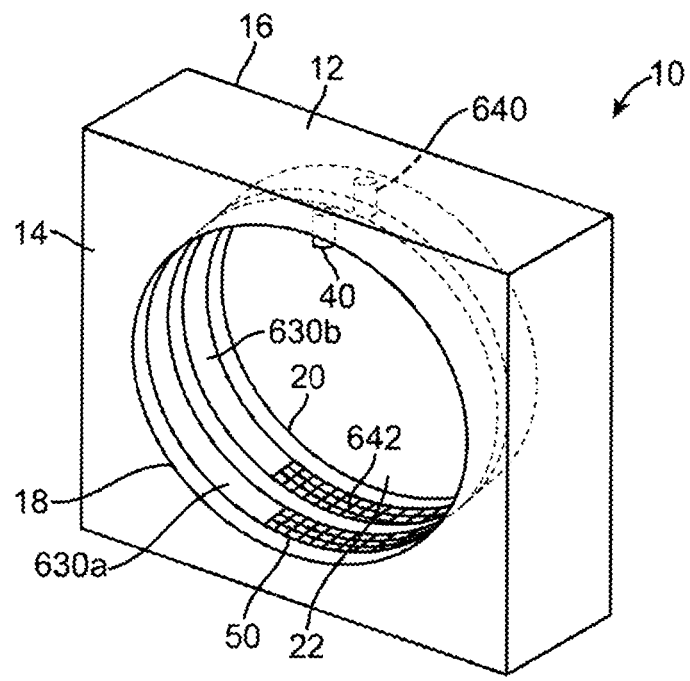

FIG. 17C illustrates a radiation system 10 in accordance with other embodiments. The radiation system 10 includes the structure 12, which has the first side 14, the second side, the first opening 18 located on the first side 14, the second opening 20 located on the second side, and the bore 22 extending between the openings 18, 20. In the illustrated embodiments, the radiation system 10 further includes a first ring 630a, and a second ring 630b. Each of the rings 630a, 630b may be a complete ring or a partial ring (e.g., an arc). The rings 630a, 630b are independently rotatable relative to the structure 12, thereby allowing the rings 630a, 630b to rotate at different speeds. Each of the rings 630 can be used to carry different devices. In the illustrated embodiments, the first ring 630a may be used to carry a treatment radiation source (such as an embodiment of the radiation source 40 described herein), and the second ring 630b may be used to carry an x-ray tube 640 and an imager 642 (which for example, may be components of a CT device). The first ring 630a is also used to carry the imager 50, such that image data can be obtained using the treatment radiation source 40 and the imager 50. In any embodiment, the first ring 630a can have one or more diagnostic sources, and one or more imagers. During use, the first ring 630a can rotate at a first speed to treat a patient and/or to generate image data using the radiation source and the imager, and the second ring 630b can rotate at a second speed to generate CT image data using the x-ray tube 640 and the imager 642, wherein the first and the second speeds are different. In some embodiments, the CT device on the second ring 630b can be used to obtain an image of a portion of a patient while the patient is being treated using the radiation source 40 on the first ring 630a.

It should be noted that the devices that can be attached to the rings 630a, 630b are not limited to the examples discussed previously. For example, in other embodiments, a diagnostic device, such as a PET device (e.g., PET imager(s)), can be secured to the second ring 630b. In such cases, the image data obtained from the imager on the first ring 630a may be used to perform attenuation correction for PET image obtained using the PET device on the second ring 630b, or may be used with the PET image data to form a composite image. The first and the second rings 630a, 630b can be configured to rotate at the same speed or different speeds to obtain a desired result. Also, in some embodiments, the first ring 630a can be configured to rotate by a first range of gantry angle to perform a first procedure, and the second ring 630b can be configured to rotate by a second range of gantry angle to perform a second procedure. The first and the second range may be the same or different, and may or may not overlap each other.

In further embodiments, the PET device may include a ring-shape PET imager. In such cases, the radiation system 10 of FIG. 17C includes one ring 630a, and does not include a second rotatable ring. For example, the second ring 630b may be fixedly secured to the structure 12 such that the second ring 630b is not rotatable relative to the structure 12, and may be used as a support to which the ring-shape PET imager is mounted. The ring-shape PET imager is secured within the bore 22 next to the first ring 630a. During use, image data are obtained using the radiation source 40 and the imager 50 mounted on the first ring 630a, and the image data may be used to correct attenuation effect in PET image data obtained using the ring-shape PET imager.

Figures 17D, 17E:
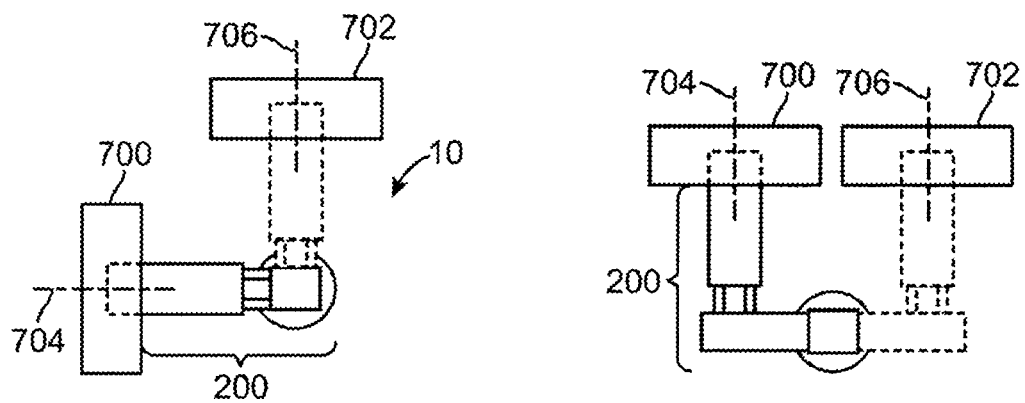

In further embodiments, the second ring 630b may carry a component, such as an imager, that is a part of an imaging device. By means of non-limiting examples, the imaging device may be a laminar tomography device, a MRI device, a fluoroscope, an angiography device, a SPECT device, or a tomosynthesis imaging device. Also, in further embodiments, instead of or in addition to having multiple rings such as rings 630a, 630b in the same structure 12, the radiation system 10 can have a first structure (e.g., structure 12) that carries the first ring 630a, and a second structure that carries the second ring 630b. The first and second structures may be dockable relative to one another, using for example, the embodiments described previously. In general, in any embodiment, each ring may carry one or more devices, each structure may carry one or more rings, and each structure may be dockable FIG. 17D illustrates a top view of a radiation system 10 in accordance with other embodiments. The radiation system 10 includes a first device 700 and a second device 702 that is oriented at 90° relative to the first device 700 (e.g., axis 704 associated with the first device 700 forms a 90° relative to axis 706 associated with the second device 702). In some embodiments, the first device 700 may be any of the embodiments of the radiation systems 10 (e.g., any of the devices of FIGS. 1A-1F) described herein. In other embodiments, the first device 700 may be a treatment machine or a diagnostic machine having other configurations. For example, the first device 700 may be a radiation treatment machine that does not have the through bore 22. Also, in some embodiments, the second device 702 may be any of the embodiments of the devices 166 (or device 100) described herein, or any treatment or diagnostic device not described herein. By means of non-limiting examples, the second device 702 may be a CT device (e.g., a CBCT device), a laminar tomography device, a MRI device, a fluoroscope, an angiography device, a PET device, a SPECT device, a PET-CT device, or a tomosynthesis imaging device. During use, the patient positioning system 200 places a patient in a first operative position associated with the first device 700 to allow a first procedure, such as a treatment procedure, be performed on at least a portion of the patient. The patient positioning system 200 then places the patient in a second operative position associated with the second device 702 to allow a second procedure, such as an imaging procedure, be performed on at least a portion of the patient. As illustrated in the embodiments, orienting the devices 700, 702 90° relative to each other is advantageous in that it allows a patient to be transported between two devices in a relatively short distance. Also, such placement of the first and second devices 700, 702 may allow them to be placed in a room having limited dimensions.

The radiation system 10 of FIG. 17D is not limited to the configuration shown. In further embodiments, the axis 704 of the first device 700 may form an angle with the axis 706 of the second device 702 that is less than 90°. For example, as shown in FIG. 17E, the first device 700 and the second device 702 may be positioned in a side-by-side configuration, wherein the axis 704 forms a 0° relative to the axis 706. During use, the patient positioning system 200 places a patient in a first operative position associated with the first device 700 to allow a first procedure, such as a treatment procedure, be performed on at least a portion of the patient. The patient positioning system 200 then places the patient in a second operative position associated with the second device 702 to allow a second procedure, such as an imaging procedure, be performed on at least a portion of the patient. In some embodiments, the patient positioning system 200 of FIG. 13A may be used with the radiation system 10 of FIG. 17E. As illustrated in the embodiments, orienting the devices 700, 702 90° or less relative to each other is advantageous in that it allows a patient to be transported between two devices in a relatively short distance. Also, such placement of the first and second devices 700, 702 may allow them to be placed in a room having limited dimensions.

In further embodiments, the axis 704 of the first device 700 may form an angle with the axis 706 of the second device 702 that is more than 90°, e.g., between 90° and 180°. Such configuration may be desirable to accommodate the devices 700, 702 in an operating room having certain size and shape.

Figure 18:
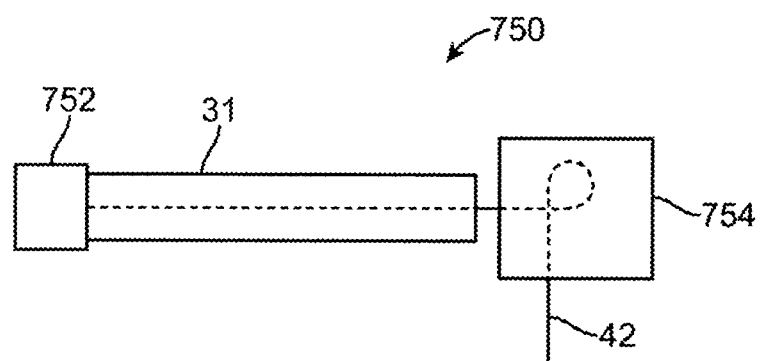
FIG. 18 illustrates a radiation beam generator having a permanent magnet for altering a trajectory of a beam in accordance with some embodiments.

FIG. 18 illustrates a schematic block diagram of a radiation beam generator 750 for providing the radiation beam 42 in accordance with some embodiments. The radiation beam generator 750 may be implemented in any of the embodiments of the radiation system 10 described herein. The radiation beam generator 750 includes a particle source 752 (e.g., an electron generator) for generating particles (e.g., electrons), the accelerator 31 for accelerating the particles, and a permanent magnet system 754 for altering a trajectory of the particles. The permanent magnet system 754 includes one or more permanent magnet(s). In the illustrated embodiments, the permanent magnet system 754 changes a direction of the beam by approximately 270°. Use of a permanent magnet system 754 to change the trajectory of the beam is advantageous because it allows the overall size of the radiation beam generator 750 be reduced (as compared to use of an electromagnetic system, which would increase the size of the generator 750).

In some embodiments, the radiation beam generator 750 may further include one or more electromagnet(s) to alter a characteristic of the magnetic field provided by the permanent magnet system 754. In such cases, the electromagnetic coils may magnetically couple with the permanent magnetic to make changes (e.g., 30% or less) in the magnetic field that is used to bend the beam. For example, the electromagnet(s) may be configured (e.g., sized, shaped, and positioned relative to the permanent magnet 754) to provide a magnetic field to change a magnitude and/or a direction of the magnetic field provided by the permanent magnet system 754, thereby allowing the generated beam to be "bent" in a desired manner. The electromagnet(s) may be positioned adjacent to the permanent magnet system 754, or connected to the permanent magnet system 754. In other embodiments, instead of using electromagnet(s), the radiation beam generator 750 may include one or more additional permanent magnet(s) for adjusting a magnetic field provided by the permanent magnet system 754. For example, the additional permanent magnet may be secured to a positioner that moves the additional permanent magnet relative to the permanent magnet system 754, thereby changing a magnitude and/or a direction of the magnetic field provided by the permanent magnet system 754. In other embodiments, other techniques known in the art may be used to vary the magnetic coupling of a magnetic material or magnet in the magnetic circuit to thereby provide the magnetic trimming functionality.

Computer System Architecture

Figure 19:
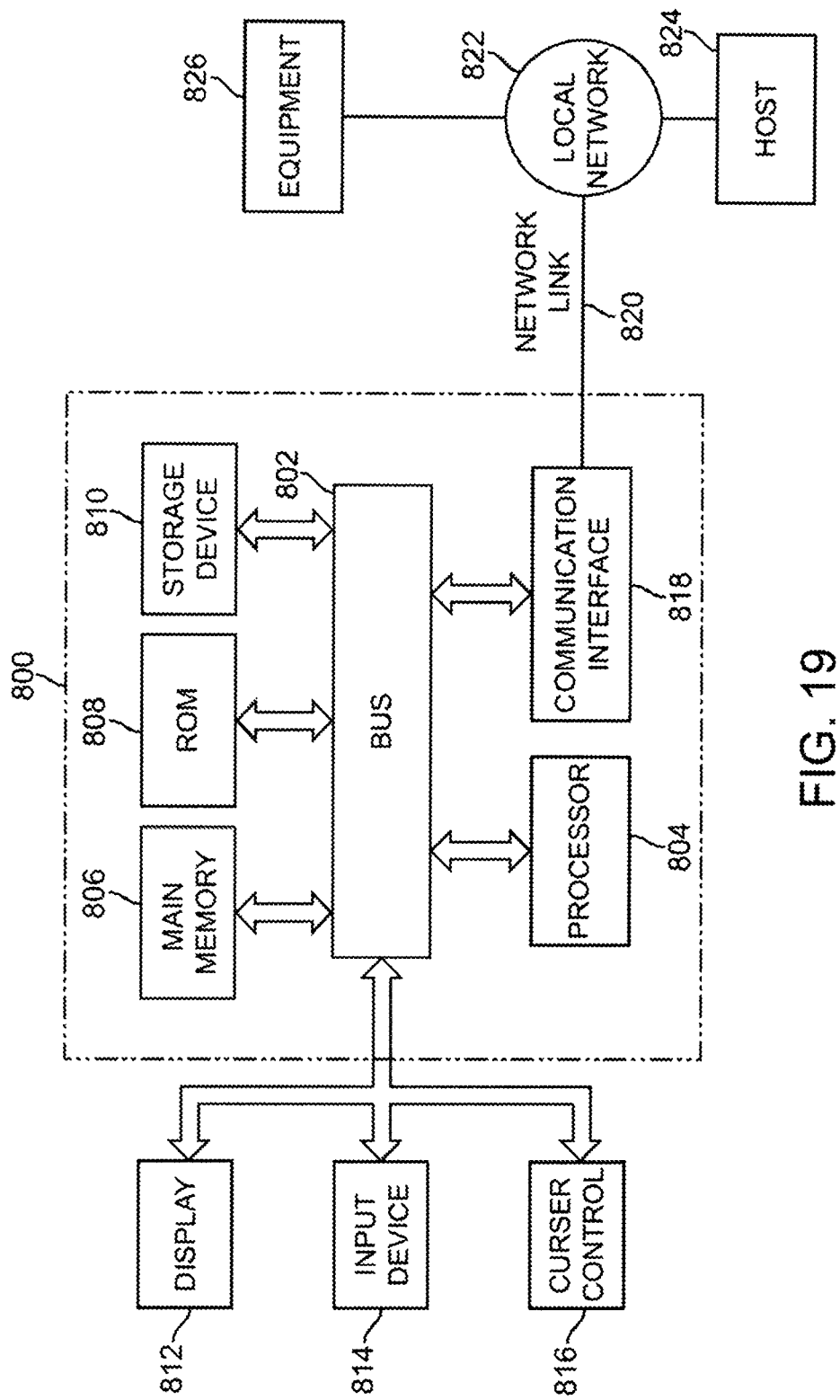
FIG. 19 illustrates a block diagram of a computer system that can be used to control an operation of a radiation system, a device, and/or a patient support system in accordance with some embodiments.

FIG. 19 is a block diagram illustrating an embodiment of a computer system 800 that can be used to implement various embodiments of the method described herein. Computer system 800 includes a bus 802 or other communication mechanism for communicating information, and a processor 804 coupled with the bus 802 for processing information. The processor 804 may be an example of the processor 84/134, or alternatively, an example of a component of the processor 84/134. The computer system 800 also includes a main memory 806, such as a random access memory (RAM) or other dynamic storage device, coupled to the bus 802 for storing information and instructions to be executed by the processor 804. The main memory 806 also may be used for storing temporary variables or other intermediate information during execution of instructions to be executed by the processor 804. The computer system 800 further includes a read only memory (ROM) 808 or other static storage device coupled to the bus 802 for storing static information and instructions for the processor 804. A data storage device 810, such as a magnetic disk or optical disk, is provided and coupled to the bus 802 for storing information and instructions.

The computer system 800 may be coupled via the bus 802 to a display 87, such as a cathode ray tube (CRT), or a flat panel display, for displaying information to a user. An input device 814, including alphanumeric and other keys, is coupled to the bus 802 for communicating information and command selections to processor 804. Another type of user input device is cursor control 816, such as a mouse, a trackball, or cursor direction keys for communicating direction information and command selections to processor 804 and for controlling cursor movement on display 87. This input device typically has two degrees of freedom in two axes, a first axis (e.g., x) and a second axis (e.g., y), that allows the device to specify positions in a plane.

In some embodiments, the computer system 800 can be used to perform various functions described herein. According to some embodiments of the invention, such use is provided by computer system 800 in response to processor 804 executing one or more sequences of one or more instructions contained in the main memory 806. Those skilled in the art will know how to prepare such instructions based on the functions and methods described herein. Such instructions may be read into the main memory 806 from another computer-readable medium, such as storage device 810. Execution of the sequences of instructions contained in the main memory 806 causes the processor 804 to perform the process steps described herein. One or more processors in a multi-processing arrangement may also be employed to execute the sequences of instructions contained in the main memory 806. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 804 for execution. Such a medium may take many forms, including but not limited to, non-volatile media, volatile media, and transmission media. Non-volatile media includes, for example, optical or magnetic disks, such as the storage device 810. Volatile media includes dynamic memory, such as the main memory 806. Transmission media includes coaxial cables, copper wire and fiber optics, including the wires that comprise the bus 802. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 804 for execution. For example, the instructions may initially be carried on a magnetic disk of a remote computer. The remote computer can load the instructions into its dynamic memory and send the instructions over a telephone line using a modem. A modem local to the computer system 800 can receive the data on the telephone line and use an infrared transmitter to convert the data to an infrared signal. An infrared detector coupled to the bus 802 can receive the data carried in the infrared signal and place the data on the bus 802. The bus 802 carries the data to the main memory 806, from which the processor 804 retrieves and executes the instructions. The instructions received by the main memory 806 may optionally be stored on the storage device 810 either before or after execution by the processor 804.

The computer system 800 also includes a communication interface 818 coupled to the bus 802. The communication interface 818 provides a two-way data communication coupling to a network link 820 that is connected to a local network 822. For example, the communication interface 818 may be an integrated services digital network (ISDN) card or a modem to provide a data communication connection to a corresponding type of telephone line. As another example, the communication interface 818 may be a local area network (LAN) card to provide a data communication connection to a compatible LAN. Wireless links may also be implemented. In any such implementation, the communication interface 818 sends and receives electrical, electromagnetic or optical signals that carry data streams representing various types of information.

The network link 820 typically provides data communication through one or more networks to other devices. For example, the network link 820 may provide a connection through local network 822 to a host computer 824 or to equipment 826, such as any of the devices herein (e.g., device 166, system 10, patient support system 200, etc.), or a switch operatively coupled to any of the devices described herein. The data streams transported over the network link 820 can comprise electrical, electromagnetic or optical signals. The signals through the various networks and the signals on the network link 820 and through the communication interface 818, which carry data to and from the computer system 800, are exemplary forms of carrier waves transporting the information. The computer system 800 can send messages and receive data, including program code, through the network(s), the network link 820, and the communication interface 818.

Although particular embodiments of the present inventions have been shown and described, it will be understood that it is not intended to limit the present inventions, and it will be obvious to those skilled in the art that various changes and modifications may be made without departing from the spirit and scope of the present inventions. For example, the term "image" or "image data" as used in this specification includes image data that may be stored in a circuitry or a computer-readable medium, and should not be limited to image data that is displayed visually. Also, it should be noted that in other embodiments, the radiation system 10 may not include one or more of the components described herein. Further, in other embodiments, the radiation system 10 may include any of the components described herein, even if the components are described as separate elements from the radiation system 10. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A radiation system, comprising:
   a structure having a first side, a second side, a first opening located on the first side, and a bore that extends from the first opening in a direction that is towards the second side;
   a radiation source coupled to the structure; and
   a patient support configured to position a part of a patient from a first operative position that is associated with the radiation source to a second operative position that is outside the bore, or vice versa, the first operative position being in the bore;
   wherein the first operative position comprises a treatment space aimed at by the radiation source, and wherein the second operative position comprises an imaging space.

2. The radiation system of claim 1, wherein the radiation source is a diagnostic radiation source.

3. The radiation system of claim 1, wherein the radiation source is a treatment radiation source.

4. The radiation system of claim 1, wherein the radiation source is capable of selectively delivering treatment radiation and diagnostic radiation.

5. The radiation system of claim 1, further comprising an arm coupled to the structure.

6. The radiation system of claim 1, further comprising a device located next to the structure, the device selected from the group consisting of a CT device, a laminar tomography device, a MRI device, a fluoroscope, an angiography device, a PET device, a PET-CT device, a SPECT device, and a tomosynthesis imaging device;
   wherein the second operative position is associated with the device located next to the structure.

7. The radiation system of claim 1, wherein the second operative position is associated with an imaging device.

8. The radiation system of claim 1, further comprising a patient position sensing device located next to the radiation source.

9. The system of claim 8, wherein the patient position sensing device is selected from the group consisting of one or more cameras, one or more infrared position sensors, one or more magnetic field sensors, one or more microwave energy sensors, one or more ultrasound energy sensors, and a strain gauge.

10. The radiation system of claim 8, wherein the position sensing device is secured to the patient support.

11. The radiation system of claim 8, wherein the patient position sensing device is mounted to a ceiling of a room in which the structure is placed.

12. The radiation system of claim 8, wherein the patient position sensing device is mounted within the bore.

13. The radiation system of claim 8, wherein the patient position sensing device includes a first camera located closer to the first side than the second side, and a second camera located closer to the second side than the first side.

14. The radiation system of claim 8, wherein the patient position sensing device includes a processor configured to identify a marker in an image.

15. The radiation system of claim 14, wherein the marker is on a marker block.

16. The radiation system of claim 14, wherein the marker is implanted inside a patient.

17. The radiation system of claim 14, wherein the processor is configured to identify a part of an anatomy of the patient as the marker.

18. The radiation system of claim 8, further comprising a processor coupled to the patient position sensing device and the radiation source, wherein the processor is configured to control an operation of the radiation source based on a signal transmitted from the patient position sensing device.

19. The radiation system of claim 18, wherein the processor is configured to determine an amplitude of a physiological movement based on the signal, and control the operation of the radiation source based at least in part on the physiological movement.

20. The radiation system of claim 18, wherein the processor is configured to determine a phase of a physiological cycle based on the signal, and control the operation of the radiation source based at least in part on the phase of the physiological cycle.

21. The radiation system of claim 8, wherein the patient position sensing device is configured to sense the part of the patient when the part of the patient is closer to the first side of the structure than the second side, and to sense the part of the patient when the part of the patient is closer to the second side of the structure than the first side.

22. The radiation system of claim 21, wherein the patient position sensing device comprises a first camera configured to aim at the part of the patient when the part of the patient is closer to the first side of the structure than the second side, and a second camera configured to aim at the part of the patient when the part of the patient is closer to the second side of the structure than the first side.

23. The radiation system of claim 21, wherein the patient position sensing device comprises a camera that is configured to couple to the patient support.

24. The radiation system of claim 1, wherein the bore and the radiation source are parts of a treatment system, and wherein the first operative position is for the radiation source of the treatment system.

25. A radiation method, comprising:
delivering radiation towards a patient, wherein the delivering of the radiation is performed using a radiation machine, wherein the radiation machine comprises a structure having a first side, a second side, a first opening located on the first side, and a bore that extends from the first opening in a direction that is towards the second side, and wherein the radiation machine further comprises a radiation source coupled to the structure; and
moving a portion of the patient from a first operative position that is associated with the radiation machine to a second operative position that is outside the bore, or vice versa, the first operative position being in the bore;
wherein the first operative position comprises a treatment space aimed at by the radiation source, and wherein the second operative position comprises an imaging space.

26. The radiation method of claim 25, wherein the second operative position is associated with a medical device facing the second side of the structure.

27. The radiation method of claim 25, further comprising using a patient position sensing device to obtain information regarding a position of the portion of the patient.

28. The radiation method of claim 27, wherein the device is used to view markers of a marker block placed on the patient.

29. The radiation method of claim 27, wherein the information is used to obtain an amplitude of a physiological movement.

30. The radiation method of claim 29, wherein the delivering of the radiation is gated based at least in part on the amplitude.

31. The radiation method of claim 27, further comprising determining a phase of a physiological cycle based on the information.

32. The radiation method of claim 31, wherein the delivering of the radiation is gated based at least in part on the phase.

33. The radiation method of claim 31, wherein the physiological cycle comprises a breathing cycle.

34. The radiation method of claim 27, wherein the patient position sensing device is configured for obtaining an image of the portion of the patient.

35. The radiation method of claim 34, wherein the image is obtained using an imaging device selected from the group consisting of a CT device, a laminar tomography device, a MRI device, a fluoroscope, an angiography device, a PET device, a PET-CT device, a SPECT device, and a tomosynthesis imaging device; and
wherein the second operative position is associated with the imaging device.

36. The radiation method of claim 27, wherein the device comprises an optical device.

37. The radiation method of claim 27, wherein the device is located within the bore.

38. The radiation method of claim 27, wherein the patient position sensing device is used to sense the portion of the patient when the portion of the patient is closer to the first side of the structure than the second side, and to sense the portion of the patient when the portion of the patient is closer to the second side of the structure than the first side.

39. The radiation method of claim 38, wherein the patient position sensing device comprises a first camera and a second camera, and wherein the act of sensing the portion of the patient comprises:
using the first camera to aim at the portion of the patient when the portion of the patient is closer to the first side of the structure than the second side; and
using the second camera to aim at the portion of the patient when the portion of the patient is closer to the second side of the structure than the first side.

40. The radiation method of claim 38, wherein the patient position sensing device comprises a camera that is configured to couple to a patient support, and wherein the method further comprises moving the camera along with the patient support.

41. The radiation method of claim 25, wherein the radiation comprises treatment radiation.

* * * * *